(12) United States Patent
Roof et al.

(10) Patent No.: US 9,987,349 B2
(45) Date of Patent: *Jun. 5, 2018

(54) USE OF A PCV2 IMMUNOGENIC COMPOSITION FOR LESSENING CLINICAL SYMPTOMS IN PIGS

(71) Applicant: Boehringer Ingelheim Vetmedica, Inc., St. Joseph, MO (US)

(72) Inventors: Michael B Roof, Ames, IA (US); Phillip Wayne Hayes, Maurice, IA (US); Marc Allan Eichmeyer, Bondurant, IA (US); Gregory Paul Nitzel, Mattawan, MI (US); Merrill Lynn Schaeffer, St. Joseph, MO (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/076,381

(22) Filed: Mar. 21, 2016

(65) Prior Publication Data

US 2016/0193320 A1    Jul. 7, 2016

Related U.S. Application Data

(60) Continuation of application No. 14/661,969, filed on Mar. 18, 2015, which is a continuation of application No. 13/106,606, filed on May 12, 2011, now Pat. No. 9,011,868, which is a continuation of application No. 12/136,923, filed on Jun. 11, 2008, now Pat. No. 7,968,285, which is a division of application No. 11/617,435, filed on Dec. 28, 2006, now abandoned.

(60) Provisional application No. 60/829,809, filed on Oct. 17, 2006, provisional application No. 60/755,016, filed on Dec. 29, 2005.

(51) Int. Cl.
  *A61K 39/12*   (2006.01)
  *C12N 7/00*    (2006.01)
  *A61K 39/00*   (2006.01)

(52) U.S. Cl.
  CPC .......... *A61K 39/12* (2013.01); *C12N 7/00* (2013.01); *A61K 2039/5252* (2013.01); *A61K 2039/5256* (2013.01); *A61K 2039/5258* (2013.01); *A61K 2039/545* (2013.01); *A61K 2039/552* (2013.01); *A61K 2039/55516* (2013.01); *A61K 2039/55555* (2013.01); *A61K 2039/55566* (2013.01); *C12N 2750/10022* (2013.01); *C12N 2750/10023* (2013.01); *C12N 2750/10034* (2013.01); *C12N 2750/10051* (2013.01); *C12N 2750/10071* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,026,543 A | 6/1991 | Rijke |
| 5,155,037 A | 10/1992 | Summers |
| 5,202,430 A | 4/1993 | Brian et al. |
| 5,322,774 A | 6/1994 | Peakman et al. |
| 5,436,001 A | 7/1995 | Kramer |
| 5,476,778 A | 12/1995 | Chladek et al. |
| 5,565,205 A | 10/1996 | Petersen et al. |
| 5,580,557 A | 12/1996 | Kramer |
| 5,733,555 A | 3/1998 | Chu |
| 5,885,823 A | 3/1999 | Knittel et al. |
| 5,925,359 A | 7/1999 | Van Woensel et al. |
| 5,968,525 A | 10/1999 | Fitzgerald et al. |
| 6,217,883 B1 | 4/2001 | Allan et al. |
| 6,287,856 B1 | 9/2001 | Poet et al. |
| 6,294,176 B1 | 9/2001 | Cochran et al. |
| 6,368,601 B1 | 4/2002 | Allan et al. |
| 6,391,314 B1 | 5/2002 | Allan et al. |
| 6,497,883 B1 | 12/2002 | Bublot et al. |
| 6,517,843 B1 | 2/2003 | Ellis et al. |
| 6,660,272 B2 | 12/2003 | Allan et al. |
| 6,703,023 B1 | 3/2004 | Jestin et al. |
| 6,794,163 B2 | 9/2004 | Liu et al. |

(Continued)

FOREIGN PATENT DOCUMENTS

| | | |
|---|---|---|
| CA | 2264953 A1 | 2/1998 |
| CA | 2305623 A1 | 4/1999 |

(Continued)

OTHER PUBLICATIONS

Fenaux et al. (Journal of Virology. 2003; 77 (20): 11232-11243).*
Mahe et al. (Journal of General Virology. 2000; 81: 1815-1824).*
"Calendar, Mar. 2007". 3rd Annual Pig Veterinary Society Congress, vol. 37, No. 2, 2007, p. 33. [Accessed at http://www.piginternational-digital.com/piginternational/2007013//Print . . . on Aug. 3, 2012].
"General Methods 6xHis and GST Purification Direct Cloning". Baculovirus Expression Vector System Manual, 6th Edition, May 1999, pp. 1-108.
"H-V11-Postweaning multisystemic wasting syndrome-Lymph node- Pig". Read-Only Case Details Reviews: Mar. 2009, pp. 1-4. [Accessed at http://www.askjpc.org/vspo/show_page.php?id=800 on Dec. 14, 2013].
9 C.F.R. § 11335 (2010).

(Continued)

*Primary Examiner* — Shanon A. Foley
(74) *Attorney, Agent, or Firm* — Judy Jarecki-Black

(57) ABSTRACT

The present invention relates to the use of an immunogenic composition that comprises a porcine circovirus type 2 (PCV2) antigen for treatment of several clinical manifestations (diseases). Preferably, the clinical manifestations are associated with a PCV2 infection. Preferably, they include lymphadenopathy, lymphoid depletion and/or multinucleated/giant histiocytes. Moreover, the clinical symptoms include lymphadenopathy in combination with one or a multiple of the following symptoms in pigs: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc. Furthermore the clinical symptoms include Pia like lesions, normally known to be associated with *Lawsonia intracellularis* infections.

50 Claims, 4 Drawing Sheets

(56) References Cited

U.S. PATENT DOCUMENTS

| | | | |
|---|---|---|---|
| 6,808,900 B2 | 10/2004 | Manitoba | |
| 6,841,364 B2 | 1/2005 | Yuan et al. | |
| 6,846,477 B2 | 1/2005 | Keich et al. | |
| 6,943,152 B1 | 9/2005 | Audonnet et al. | |
| 6,953,581 B2 | 10/2005 | Allan et al. | |
| 7,018,638 B2 | 3/2006 | Chu et al. | |
| 7,109,025 B1 | 9/2006 | Eloit et al. | |
| 7,122,192 B2 | 10/2006 | Allan et al. | |
| 7,144,698 B2 | 12/2006 | Wang et al. | |
| 7,148,015 B2 | 12/2006 | Jestin et al. | |
| 7,169,394 B2 | 1/2007 | Chu et al. | |
| 7,172,899 B2 | 2/2007 | Liu et al. | |
| 7,179,472 B2 | 2/2007 | Jestin et al. | |
| 7,192,594 B2 | 3/2007 | Haines et al. | |
| 7,211,379 B2 | 5/2007 | Ellis et al. | |
| 7,223,407 B2 | 5/2007 | Jestin et al. | |
| 7,223,594 B2 | 5/2007 | Jestin et al. | |
| 7,244,433 B2 | 7/2007 | Jestin et al. | |
| 7,258,865 B2 | 8/2007 | Jestin et al. | |
| 7,261,898 B2 | 8/2007 | Jestin et al. | |
| 7,273,617 B2 | 9/2007 | Yuan et al. | |
| 7,276,353 B2 | 10/2007 | Meng et al. | |
| 7,279,166 B2 | 10/2007 | Meng et al. | |
| 7,297,537 B2 | 11/2007 | Jestin et al. | |
| 7,300,785 B2 | 11/2007 | Meerts et al. | |
| 7,312,065 B2 | 12/2007 | Roof et al. | |
| 7,314,628 B2 | 1/2008 | Jestin et al. | |
| 7,323,330 B2 | 1/2008 | Jestin et al. | |
| 7,335,361 B2 | 2/2008 | Liao et al. | |
| 7,358,075 B2 | 4/2008 | Allibert et al. | |
| 7,368,117 B2 | 5/2008 | Fetzer et al. | |
| 7,371,395 B2 | 5/2008 | Parisot et al. | |
| 7,390,494 B2 | 6/2008 | Jestin et al. | |
| 7,405,075 B2 | 7/2008 | Jestin et al. | |
| 7,407,803 B2 | 8/2008 | Jestin et al. | |
| 7,425,444 B2 | 9/2008 | Jestin et al. | |
| 7,700,285 B1 | 4/2010 | Eichmeyer et al. | |
| 7,758,865 B2 | 7/2010 | Jestin et al. | |
| 7,829,101 B2 | 11/2010 | Eichmeyer et al. | |
| 7,829,273 B2 | 11/2010 | Roof et al. | |
| 7,829,274 B2 | 11/2010 | Fachinger et al. | |
| 7,833,707 B2 | 11/2010 | Eichmeyer et al. | |
| 7,838,213 B2 | 11/2010 | Roof et al. | |
| 7,838,214 B2 | 11/2010 | Roof et al. | |
| 7,910,306 B2 | 3/2011 | Eichmeyer et al. | |
| 7,914,992 B2 | 3/2011 | Fachinger et al. | |
| 7,943,298 B2 | 5/2011 | Fachinger et al. | |
| 7,951,907 B2 | 5/2011 | Jestin et al. | |
| 7,968,285 B2 | 6/2011 | Roof et al. | |
| 8,025,888 B2 | 9/2011 | Eichmeyer et al. | |
| 8,119,143 B2 | 2/2012 | Roof et al. | |
| 8,475,805 B2 | 7/2013 | Fachinger et al. | |
| 8,496,940 B2 | 7/2013 | Fachinger et al. | |
| 8,852,613 B2 | 10/2014 | Ohnesorge et al. | |
| 8,865,183 B2 | 10/2014 | Fachinger et al. | |
| 9,011,868 B2 | 4/2015 | Roof et al. | |
| 9,011,872 B2 | 4/2015 | Eichmeyer et al. | |
| 9,132,187 B2 | 9/2015 | Fachinger et al. | |
| 9,517,260 B2 | 12/2016 | Fachinger et al. | |
| 9,522,182 B2 | 12/2016 | Fachinger et al. | |
| 9,555,092 B2 | 1/2017 | Fachinger et al. | |
| 9,669,087 B2* | 6/2017 | Roof | A61K 39/12 |
| 2002/0146431 A1 | 10/2002 | Allan et al. | |
| 2003/0096377 A1 | 5/2003 | Meng et al. | |
| 2003/0170270 A1 | 9/2003 | Meng et al. | |
| 2003/0199581 A1 | 10/2003 | Seligson et al. | |
| 2003/0215455 A1 | 11/2003 | Reynolds et al. | |
| 2004/0062775 A1 | 4/2004 | Jestin et al. | |
| 2004/0076635 A1 | 4/2004 | Jestin et al. | |
| 2004/0091502 A1 | 5/2004 | Jestin et al. | |
| 2004/0132178 A1 | 7/2004 | Haines et al. | |
| 2004/0161410 A1 | 8/2004 | Jestin et al. | |
| 2004/0208901 A1 | 10/2004 | Ellsworth et al. | |
| 2004/0253270 A1 | 12/2004 | Meng et al. | |
| 2004/0258715 A1 | 12/2004 | Allan et al. | |
| 2004/0265848 A1 | 12/2004 | Jestin et al. | |
| 2005/0008651 A1 | 1/2005 | Jestin et al. | |
| 2005/0013823 A1 | 1/2005 | Keich et al. | |
| 2005/0031647 A1 | 2/2005 | Roof et al. | |
| 2005/0058653 A1 | 3/2005 | Ellis et al. | |
| 2005/0079185 A1 | 4/2005 | Parisot et al. | |
| 2005/0084497 A1 | 4/2005 | Jestin et al. | |
| 2005/0147966 A1 | 7/2005 | Meng et al. | |
| 2005/0238662 A1 | 10/2005 | Jestin et al. | |
| 2006/0002952 A1 | 1/2006 | Haines et al. | |
| 2006/0029617 A1 | 2/2006 | Charreyre et al. | |
| 2006/0083756 A1 | 4/2006 | Jestin et al. | |
| 2006/0115489 A1 | 6/2006 | Birkett et al. | |
| 2006/0204522 A1 | 9/2006 | Kroll et al. | |
| 2006/0222659 A1 | 10/2006 | Jestin et al. | |
| 2006/0228373 A1 | 10/2006 | Chu et al. | |
| 2006/0233831 A1 | 10/2006 | Parisot et al. | |
| 2006/0246425 A1 | 11/2006 | Allibert et al. | |
| 2006/0286123 A1 | 12/2006 | Fetzer et al. | |
| 2007/0196879 A1 | 8/2007 | Chabriere et al. | |
| 2008/0181910 A1 | 7/2008 | Roof et al. | |
| 2008/0226669 A1 | 9/2008 | Roof et al. | |
| 2008/0233147 A1 | 9/2008 | Jestin et al. | |
| 2008/0261887 A1 | 10/2008 | Roof et al. | |
| 2008/0267995 A1 | 10/2008 | Roof et al. | |
| 2008/0279875 A1 | 11/2008 | Roof et al. | |
| 2008/0279876 A1 | 11/2008 | Roof et al. | |
| 2008/0279889 A1 | 11/2008 | Roof et al. | |
| 2009/0010954 A1 | 1/2009 | Fachinger et al. | |
| 2009/0016992 A1 | 1/2009 | Eichmeyer et al. | |
| 2009/0017064 A1 | 1/2009 | Wu et al. | |
| 2009/0022751 A1 | 1/2009 | Eichmeyer et al. | |
| 2009/0042245 A1 | 2/2009 | Eichmeyer et al. | |
| 2009/0317423 A1 | 12/2009 | Roof et al. | |
| 2010/0136060 A1 | 6/2010 | Kolb | |
| 2010/0150959 A1 | 6/2010 | Sheppard et al. | |
| 2010/0184016 A1 | 7/2010 | Lefebvre et al. | |
| 2010/0189743 A1 | 7/2010 | Jestin et al. | |
| 2011/0033495 A1 | 2/2011 | Roof et al. | |
| 2011/0059126 A1 | 3/2011 | Kohler et al. | |
| 2011/0091499 A1 | 4/2011 | Fachinger et al. | |
| 2011/0150770 A1 | 6/2011 | Bautista et al. | |
| 2011/0217327 A1 | 9/2011 | Roof et al. | |
| 2011/0274710 A1 | 11/2011 | Eichmeyer et al. | |
| 2013/0115236 A1 | 5/2013 | Fachinger et al. | |
| 2013/0230558 A1 | 9/2013 | Ohnesorge et al. | |
| 2013/0273099 A1 | 10/2013 | Fachinger et al. | |
| 2013/0302370 A1 | 11/2013 | Fachinger et al. | |
| 2014/0322267 A1 | 10/2014 | Haiwick et al. | |
| 2014/0348874 A1 | 11/2014 | Segales et al. | |
| 2014/0377298 A1 | 12/2014 | Fachinger et al. | |
| 2015/0056248 A1 | 2/2015 | Haiwick et al. | |
| 2015/0093404 A1 | 4/2015 | Hernandez et al. | |
| 2015/0174233 A1 | 6/2015 | Roof et al. | |
| 2015/0190497 A1 | 7/2015 | Eichmeyer et al. | |
| 2015/0190498 A1 | 7/2015 | Roof et al. | |
| 2015/0297707 A1 | 10/2015 | Roof et al. | |
| 2015/0297708 A1 | 10/2015 | Roof et al. | |
| 2015/0320853 A1 | 11/2015 | Elbers et al. | |
| 2015/0343052 A1 | 12/2015 | Fachinger et al. | |
| 2016/0193320 A1* | 7/2016 | Roof | A61K 39/12 424/186.1 |
| 2017/0049875 A1 | 2/2017 | Roof et al. | |
| 2017/0049876 A1 | 2/2017 | Fachinger et al. | |
| 2017/0049878 A1 | 2/2017 | Fachinger et al. | |

FOREIGN PATENT DOCUMENTS

| | | |
|---|---|---|
| CN | 1579553 A | 7/1920 |
| CN | 1409765 A | 4/2003 |
| CN | 1458167 A | 11/2003 |
| CN | 103122352 A | 5/2013 |
| EP | 1050584 A1 | 11/2000 |
| EP | 1281760 A1 | 2/2003 |
| EP | 1386617 A1 | 2/2004 |
| JP | 2002247979 A | 9/2002 |
| JP | 2005511075 A | 4/2005 |
| KR | 100478845 B1 | 3/2005 |
| WO | 1989006972 A1 | 8/1989 |

(56) References Cited

FOREIGN PATENT DOCUMENTS

| | | |
|---|---|---|
| WO | 1990007935 A1 | 7/1990 |
| WO | 1991018627 A1 | 12/1991 |
| WO | 1992003157 A1 | 3/1992 |
| WO | 1993016726 A2 | 9/1993 |
| WO | 1996036356 A1 | 11/1996 |
| WO | 1999018214 A1 | 4/1999 |
| WO | 1999029717 A3 | 6/1999 |
| WO | 1999029871 A3 | 6/1999 |
| WO | 2000001409 A2 | 1/2000 |
| WO | 2000047756 A1 | 8/2000 |
| WO | 2000077188 A2 | 12/2000 |
| WO | 2000077216 A2 | 12/2000 |
| WO | 2001016330 A2 | 3/2001 |
| WO | 2001017556 A1 | 3/2001 |
| WO | 2001034191 A1 | 5/2001 |
| WO | 2001045735 A2 | 6/2001 |
| WO | 2001096377 A2 | 12/2001 |
| WO | 2002049666 A2 | 6/2002 |
| WO | 2002077210 A2 | 10/2002 |
| WO | 2003003941 A2 | 1/2003 |
| WO | 2003049703 A2 | 6/2003 |
| WO | 2003068993 A1 | 8/2003 |
| WO | 2004026336 A1 | 4/2004 |
| WO | 2004058142 A2 | 7/2004 |
| WO | 2004069184 A2 | 8/2004 |
| WO | 2005009462 A2 | 2/2005 |
| WO | 2005092069 A2 | 10/2005 |
| WO | 2005112995 A1 | 12/2005 |
| WO | 2006068663 A2 | 6/2006 |
| WO | 2006072065 A2 | 7/2006 |
| WO | 2006113372 A2 | 10/2006 |
| WO | 2006113373 A2 | 10/2006 |
| WO | 2007028823 A1 | 3/2007 |
| WO | 2007076520 A2 | 7/2007 |
| WO | 2007094893 A2 | 8/2007 |
| WO | 2008073464 A2 | 6/2008 |
| WO | 2008076915 A2 | 6/2008 |
| WO | 2008081015 A1 | 7/2008 |
| WO | 2008098909 A1 | 8/2008 |
| WO | 2009030684 A2 | 3/2009 |
| WO | 2009103037 A1 | 8/2009 |
| WO | 2009126356 A2 | 10/2009 |
| WO | 2011116094 A2 | 9/2011 |
| WO | 2012033911 A2 | 3/2012 |
| WO | 2014134561 A2 | 9/2014 |
| WO | 2014179200 A1 | 11/2014 |
| WO | 2015026912 A1 | 2/2015 |
| WO | 2015051099 A1 | 4/2015 |
| WO | 2015169732 A1 | 11/2015 |
| WO | 2016160761 A2 | 10/2016 |

OTHER PUBLICATIONS

Abstract in English of CN1458167, dated Nov. 26, 2003.
Albina et al., "An Experimental Model for Post-weaning Multisystenic Wasting Syndrome (PMWS) in Growing Piglets". 2001, Journal of Comparative Pathology, vol. 123, pp. 292-303.
Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.
Allan et al., "Letters, Immunostiulations, PCV-2 and PMWS", The Vet Records, Aug 5, 2000, pp. 170-171.
Allan et al., "Passive Transfer of Maternal Antibodies to PCV2 Protects Against Development of Post-weaning Multisystemic Wasting Syndrome (PMWS): Experiemental Infections and a Field Study". 2002, The Pig Journal, vol. 50, pp. 59-67.
Allan et al., "PCV2; ticking time bomb?" Pig Progress, vol. 18, No. 5, 2002, pp. 14-15.
Allan et al., "PMWS/PCVD: Diagnosis, Disease, and Control: What do we know?" 2006, Proceedings of the 19th IPVS Congress, Copenhagen, Denmark, vol. 1, pp. 1-9.
Allan et al., "Porcine Circoviruses; A Review", J. Vet., Diagn. Invest. 2000, 12, pp. 3-14.
Allan et al., "Reproduction of postweaning multisystemic wasting syndrome in pigs experimentally inoculated with a Swedish porcine circovirus 2 isolate". 2003, Journal of Veterinary Diagnostic Investigation, vol. 15, pp. 553-560.
Allan et al., Guest Editorial, "PCV-2 Infection in Swine; More Than Just Postweaning Multisystemic Wasting Syndrome", The Vet Journ., 2003, 166, pp. 222-223.
Bahnemann, Hans G., "Inactivation of Viruses in Serum with Binary Ethyleneimine". Journal of Clinical Microbiology, vol. 3, No. 2, Feb. 1976, pp. 209-210.
Banholzer, E . "A Follow-Up: PCV2, PRRS, Mycoplasma hyopneumoniae, Improvac". IPVS Congress, Jul. 16-19, 2006, pp. 1-20.
Bassaganya-Riera et al., "Conjugated Linoleic Acid Ameliorates Viral Infectivity in a Pig Model of Virally Induced Immunosuppression". 2003, American Society for Nutritional Sciences, pp. 3204-3214.
Beach et al., "Efficacy and future prospects of commercially available and experimental vaccines against porcine circovirus type 2 (PCV2)". Virus Research, vol. 164, 2012, pp. 33-42.
Begue et al. "Future Combined Vaccines". Journal of Infectious Diseases, vol. 173, Supp 3, 1996, pp. S295-S297.
Beseme et al., "Vaccination strategies for the control of circoviral diseases in pigs: PMWS and PCV2-associated PRDC". Proceedings of the Japanese Pig Veterinary Society, vol. 49, 2006, pp. 15-38.
Blanchard et al., "An ORF2 protein-based ELISA for porcine circovirus type 2 antibodies in post-weaning multisystemic wasting syndrome". Veterinary Microbiology, vol. 94, 2003, pp. 183-194.
Blanchard et al., "Protection of swine against post-weaning multisystemic wasting syndrome (PMWS) by porcine circovirus type 2 (PCV2) proteins". Vaccine, vol. 21, 2003, pp. 4565-4575.
Boehringer Ingelheim Vetmedica, Inc., "Data from studies consistent with maintaining safety and efficacy of Ingelvac CircoFLEXâ and Ingelvac MycoFLEXâ vaccines when mixed together and administered concurrently to pigs". Feb. 2008, Technical Bulletion, www.bi-vetmedica.com/swine-research/MycoFLEX-Mycoplasma-immunity_TB2.pdf; 14 pages.
Boehringer Ingelheim Vetmedica, Inc., Ingelvacâ Circoflexâ Material Safety Data Sheet, Online Oct. 2006, pp. 1-10 URL:http://bi-vetmedica.com/sites/default/files/ingelvac-circoflex-msds.pdf.
Boisseson et al., "Molecular characterization of Porcine circovirus type 2 isolates from post-weaning multisystemic wasting syndrome-affected and non-affected pigs". 2004, Journal of General Virology, vol. 85, pp. 293-304.
Bolin et al., "Postweaning multisystemic wasting syndrome induced after experimental inoculation of cesarean-derived, colostrum-deprived piglets with type 2 porcine circovirus". 2001, Journal of Veterinary Diagnostice Investigation, vol. 13, pp. 185-194.
Bowie, et al., "Deciphering the Message in Protein Sequences: Tolerance to Amino Acid Substitutions," Science, vol. 247, 1990, pp. 1306-1310.
Brogden, Kim A., "Polymicrobial Diseases of Animals and Humans". Polymicrobial Diseases, Chapter 1, 2002, 19 pages. [Accessed at http://www.ncbi.nlm.nih.gov/books/NBK2477/?report=printable on Jul. 8, 2014].
Caprioli et al., "PCR detection of porcine circovirus type 2 (PCV2) DNA in blood, tonsillar and faecal swabs from experimentally infected pigs". Research in Veterinary Sciences, vol. 81, No. 2, Oct. 2006, pp. 287-292.
Chae, C. "A review of porcine circovirus 2-associated syndromes and diseases". The Veterinary Journal, vol. 169, No. 3, 2005, pp. 326-336.
Chae, C., "Postweaning multisystemic wasting syndrome: a review of aetiology, diagnosis and pathology" 2004, The Veterinary Journal, vol. 168, pp. 41-49.
Charbonneau, G., "Canadian Experiences with Porcine Circovirus Associated Disease" 2007, Iowa Pork Congress; 30 pages.
Chen et al., "Serological survey of serum antibodies against porcine circovirus type 2 (PCV2) in swine, chicken, duck, goat and cattle fromZhejiang province, China". Revue de Médecine Vétérinaire, vol. 158, Nos. 8-9, 2007, pp. 458-462.

(56) References Cited

OTHER PUBLICATIONS

Cheung et al., "Kinetics of Porcine Circovirus Type 2 Replication". Archives of Virology, vol. 147, 2002, pp. 43-58.

Chevez et al., "Long-term analysis of PCV2 prevalence in a Mexican herd using Ingelvac CircoFLES®". 22nd International Pig Veterinary Society Congress, Virology and Viral Diseases—PCV2, 2012, p. 908.

Chiou, et al., "The Effect of Porcine Circovirus Infection on the Immune Response of Pigs After Vaccination Against Classical Swine Fever and Pseudorabies". 2006, Proceedings of the 19th IPVS Congress, Copenhagen, Denmark, p. 79.

Chung et al., "Real-time PCR for quantitation of porcine reproductive and respiratory syndrome virus and porcine circovirus type 2 in naturally-infected and challenged pigs". Journal of Virological Methods, vol. 124, 2005, pp. 11-19.

Czermak et al., "Membrane Filtration in Animal Cell Cutlure". 2007, Methods in Biotechnology, vol. 24, pp. 397-420 Humana Press, New Jersey, USA.

Darwich et al., "Cytokine profiles of peripheral blood mononuclear cells from pigs with postweaning multisystemic wasting syndrome in response to mitogen, superantigen or recall viral antigens". 2003, Journal of General Virology, vol. 84, pp. 3453-3457.

Dawson et al., "Studies of the field efficacy and safety of a single-dose Mycoplasma hyopneumoniae vaccine for pigs". Veterinary Record, vol. 151, 2002, pp. 535-538.

Duarte et al., "Concomitant Zearalenone Ingestion and Porcine Circovirus-2 Infection". Acta Scientiae Veterinariae vol. 41, Suppl. 1, Publication 37, 2013, pp. 1-6.

Dugdale et al., "Immune Response". Medline Plus Medicial Encyclopedia, Updated May 30, 2012, pp. 1-4. [Accessed at http://www.nlm.nih.gov/medlineplus/cncy/article/000821.htm on Mar. 19, 2014].

Ellis et al., "Lack of antibodies to porcine circovirus type 2 virus in beef and dairy cattle and horses in western Canada". Canadian Veterinary Journal, vol. 42, 2001, pp. 461-464.

Ellis et al., "Porcine circovirus-2 and concurrent infections in the field". Veterinary Microbiology, vol. 98, No. 2, Feb. 2004, pp. 159-163.

Ellis, John A., "Porcine circovirus: An old virus in a new guise causes an emerging disease thorugh a novel pathogenesis". Large Animal Veterinary Rounds, vol. 3, No. 4, Apr. 2003, pp. 1-6.

EMBL Acession No. ACA49861, Wang et al., "Porcine circovirus-2 capside protein"., Mar. 5, 2008, 1 page.

EMBL Acession No. ACA49867, Wang et al., "Porcine circovirus-2 capside protein"., Mar. 5, 2008, 1 page.

EMBL Acession No. ACV53224, Cortey et al., "Porcine circovirus-2 partial capsid protein"., Sep. 13, 2009, 1 page.

European Search Report (Supplementary) for EP07867723 dated May 20, 2010.

Fablet et al., "A Case Study of Neonatal Diarrhoea in a Farrow-to-Finish Pig Farm". International Society for Animal Hygiene, Saint Malo, 2004, p. 151.

Thacker et al. "Porcine Respiratory Disease Complex (PRDC)". Thai Journal of Veterinary Medicine, vol. 32, Supp., 2002, pp. 126-134.

Stoltenow, Charles L. "Getting the Most Out of a Vaccine Program". Proceedings, The Range Beef Cow Symposium XIX, Rapid City, SD, 2005, pp. 139-144.

Williams et al., "Combined vaccines and simultaneous administration: Current issues and perspectives". Annals of the New York Academy of Sciences, vol. 754, 1995, pp. xi-xv, 35-47.

Wu et al., "Replication, Integration, and Packaging of Plasmid DNA following Cotransfection with Baculovirus Viral DNA". Journal of Virology, vol. 73, No. 7, Jul. 1999, pp. 5473-5480.

Xia et al., "Preparation of and Immunity Tests with Canine Coronavirus BEI Inactivated Vaccine". Chinese Journal of Veterinary Medicine, vol. 37, No. 3, 2001, pp. 37-38.

Yamada et al., "Evaluation of the Efficacy of Inactivated Vaccine against *Salmonella enteritidis* Infection in Chicken". Journal of the Japanese Society on Poultry Diseases, vol. 35, No. 1, 1999, pp. 13-21. (English Summary at p. 21).

Yang, "A Survey on Porcine Circovirus Type 2 Infection and Phylogenetic Analysis of its ORF2 Gene in Hangzhou, Zhejiang Province, CN," J. Zhejiang Univ. Science B, vol. 9(2), 2008, pp. 148-153.

Yuan et al., "Immunology of the porcine respiratory disease complex". Animal Science Abroad in Pigs and Poultry, No. 5, 2002, pp. 36-38.

Zhang et al., "Cytokine and chemokine mRNA expression profiles in tracheobronchial lymph nodes from pigs singularly infected or coinfected with porcine circovirus type 2 (PCV2) and Mycoplasma hyopneumoniae (MHYO)". Veterinary Immunology and Immunopathology, vol. 140, 2011, pp. 152-158.

""PRRS Plus"—PRRS Virus Infection in Combination with Other Agents PG Halbur". 2003 PRRS Compendium Producer Edition, 2003, pp. 18-24. [Accessed at http://old.pork.org/filelibrary/prrs/2003compendium/prrschapter3.pdf on Jun. 2, 2015].

Fraile et al., "Effect of sow and piglet porcine circovirus type 2 (PCV2) vaccination on piglet mortality, viraemia, antibody titre and production parameters". Veterinary Microbiology, vol. 161, 2012, pp. 229-234.

Kekarainen et al., "Immune responses and vaccine-induced immunity against Porcine circovirus type 2". Veterinary Immunology and Immunopathology, vol. 136, 2010, pp. 185-193.

Opriessnig et al., "Comparison of the effectiveness of passive (dam) versive active (piglet) immunization against porcine circovirus type 2 (PCV2) and impact of passively derived PCV2 vaccine-induced immunity on vaccination". Veterinary Microbiology, vol. 142, 2010, pp. 177-183.

Pejsak et al., "Efficacy of different protocols of vaccination against porcine circovirus type 2 (PCV2) in a farm affected py postweaning multisystemic wasting syndrome (PMWS)". Comparative Immunology, Microbiology, and Infectious Disease, vol. 33, 2010, pp. e1-e5.

Pejsak et al., "Influence of long-term vaccination of a breeding herd of pigs against PCV2 on reproductive parameters". Polish Journal of Veterinary Sciences, vol. 15, No. 1, 2012, pp. 37-42.

"Reproduction in the Sow". The Reprodocution in Pig, Aug. 28, 2012, pp. 1-8 (www2.unipr.it/~fderensi/rip_pig/rip_pig.htm). [Accessed at https://web.archive.org/web/20120828155058/http://www2.unipr.it/~fderensi/rip_pig/rip_pig.htm on Feb. 25, 2014].

Desmettre et al., "Research and Development". Veterinary Vaccinology, Second Impression, Chapter 9, Elsevier, Amsterdam, 1999, pp. 175, 177, and 178.

Schinckel et al., "Analysis of Pig Growth from Birth to Sixty Days of Age". 2003 Swine Research Report, Purdue Jniversity, 2003, pp. 57, 61.

European Medical Agency, "Annex I: Summary of Product Characteristics: Ingelvac CircoFLEX suspensions for injections in pigs". EPAR Product Information, Feb. 13, 2008, pp. 1-5. [Accessed at: http://www.ema.europa.eu/docs/en_GB/document_library/EPAR_-_Product_Information/veterinary/000126/WC500062388.pdf on Jun. 3, 2015].

Thacker, Brad, "Update on Intervet's Porcine Circovirus Type 2 Vaccine". ISU Swine Disease Conference for Swine Practitioner, 2006, pp. 1-2.

Opriessnig et al., "Effect of porcine parvovirus vaccination on the development of PMWS in segregated early weaned pigs coinfected with type 2 porcine circovirus and porcine parvovirus". Veterinary Microbiology, vol. 98, 2004, pp. 209-220.

SEQ ID No. 2 Sequence Alignment with Geneseq Database Accession No. AWF75404 submitted Apr. 2, 2009 in US2009/0017064, 3 pages.

SEQ ID No. 1 Sequence Alignment with Geneseq Database Accession No. AWF75438 submitted Apr. 2, 2009 in US2009/0017064, 3 pages.

Belikov, V.G., "Connection between the molecular structure of substances and their action on organisms". Pharmaceutical Chemistry, vol. 1, Section 2.2, 1993, p. 43.

Mashkovski, M.D., "Interaction of Drugs". Medicaments, A Doctor's Manual, 14th Edition, vol. 1, Section 9, Moscow, 2001, p. 11.

(56) References Cited

OTHER PUBLICATIONS

Gupta et al., "Adjuvants for human vaccines-current status, problems and future prospects". Vaccine, vol. 13, No. 14, 1995, pp. 1263-1276.

Oh et al., "Evaluation of Two Different Vaccine Program Against M. Hyopneumniae on an 1100 Sow Farm in Korea". Asian Pig Veterinary Society Congress, Sep. 2013, 1 page.

Eichmeyer et al., "Efficacy evaluation of a Mycoplasma hyopneumoniae bacterin in a mixture with a porcine circovirus type 2 vaccine". Allen D. Leman Swine Conference-Recent Research Reports, 2008, pp. 28.

Beach et al., "Novel chimeric porcine circovirus (PCV) with the capsid gene of the emerging PCV2b subtype cloned in the genomic bacbone of the non-pathogenic PCV1 is attenuated in vivo and induces protective and cross-protective mmunity against PCV2b and PCV2a subtypes in pigs". Vaccine, vol. 29, 2011, pp. 221-232.

SEQ ID No. 2 Sequence Alignment with Geneseq Database Accession No. AWF75438 submitted Apr. 2, 2009 in US2009/0017064, pp. 1-3.

SEQ ID No. 1 Sequence Alignment with Geneseq Database Accession No. AWF75404 submitted Apr. 2, 2009 in US2009/0017064, 3 pages.

SEQ ID No. 1 Sequence Alignment with Geneseq Database Accession No. AZR61798 submitted Feb. 16, 2012 in CN102296089, 2 pages.

SEQ ID No. 2 Sequence Alignment with Geneseq Database Accession No. ARY99931 submitted Aug. 21, 2008 in WO2008/076915, 2 pages.

SEQ ID No. 1 Sequence Alignment with GenEmbl Database Accession No. JN006448 submitted Dec. 6, 2011 in Turcitu et al., "Genetic diversity of porcine circovirus type 2 (PCV2) in the Romanian wild board population". Res. Vet. Sci., vol. 91, No. 3, 2011, E103-106, 5 pages.

SEQ ID No. 1 Sequence Alignment with GenEmbl Database Accession No. GQ845027 submitted Mar. 31, 2010 in Li et al., "Genetic analysis of porcine circovirus type 2 (PCV2) strains isolated between 2001 and 2009: genotype PCV2b predominate in postweaning multisystemic wasting syndrome occurrences in eastern China". Virus Genes, vol. 40, No. 2, 2010, pp. 244-251, 5 pages.

Liu et al., "Efficient production of type 2 porcine circovirus-like particles by a recombinant baculovirus". Archives of Virology, vol. 153, 2008, pp. 2291-2295.

Guedes et al., "Onset and duration of fecal shedding, cell-mediated and humoral immune responses in pigs after challenge with a pathogenic isolate or attenuated vaccine strain of Lawsonia intracellularis". Veterinary Microbiology, vol. 91, 2003, pp. 135-145.

Genbank Accession# AAC35299, ORF2 [Porcine circovirus], Sep. 13, 1998.

Weibel et al., "A field efficacy study with Enterisol® Ileitis and Ingelvac CircoFLEX® in Switzerland". Poster Presentations, Porcine Circovirus Assoicated Diseases (PCVAD-Control) (P.113), Proceedings of the 21st IPVS Congress, Vancourver, Canada, Jul. 18-21, 2010, p. 419.

Pyle et al., "Secretion of biologically active human proapolipoprotein A-I in a baculovirus-insect cell system: protection from degradation by protease inhibitors". Journal of Lipid Research, vol. 36, 1995, pp. 2355-2361.

Boisgerault et al., "Virus-like particles: a new family of delivery systems". Expert Review of Vaccines, vol. 1, No. 1, Jun. 2002, pp. 101-109.

Weingartl et al., "Porcine circovirus structure and replication: a minireview". Agriculture, vol. 1, 2002, pp. 11-14.

Boga et al., "A single dose immunization with rabbit haemorrhagic disease virus major capsid protein produced in *Saccharomyces cerevisiae* induces protection". Journal of General Virology, vol. 78, 1997, pp. 2315-2318.

Bachmann et al., "The influence of virus structure on antibody responses and virus serotype formation". Immunology Today, vol. 17, No. 12, Dec. 1996, pp. 553-558.

Fan et al., "Baculovirus-Insect Expression and Immunological Studies of Porcin Circovirus Type 2 (PCV2) Capsid Protein". Proceedings of the 2nd Asian Pig Veterinary Society Congress, Sep. 19-21, 2005, Philippines, pp. 186-188.

Liljeqvist et al., "Production of recombinant subunit vaccines: protein immunogens, live delivery systems and nucleic acid vaccines". Journal of Biotechnology, vol. 73, 1999, pp. 1-33.

Invitrogen Life Technologies, "Guide to Baculovirus Express Vector Systems (BEVS) and Insect Cell Culture Techniques". Feb. 27, 2002, pp. 1-130. [Accessed at https://tools.thermofisher.com/content/sfs/manuals/bevtest.pdf].

Ragona et al., "The Transcriptional Factor Egr-1 Is Synthesized by Baculovirus-Infected Insect Cells in an Active, DNA-Binding Form". DNA and Cell Biology, vol. 10, No. 1, 1991, pp. 61-66.

Riggs et al., "Efficacy of Monoclonal Antibodies against Defined Antigens for Passive Immunotherapy of Chronic Gastrointestinal Cryptosporidiosis". Antimicrobial Agents and Chemotherapy, vol. 46, No. 2, Feb. 2002, pp. 275-282.

Riggs et al., "Protective Monoclonal Antibody Defines a Circumsporozoite-Like Glycoprotein Exoantigen of Cryptosporidium parvum Sporozoites and Merozoites". The Journal of Immunology, vol. 158, 1997, pp. 1787-1795.

Rodríguez-Arrioja et al., "Dynamics of procine circovirus type 2 infection in a herd of pigs with postweaning multisystemic wasting syndrome". American Journal of Veterinary Research, vol. 63, No. 3, Mar. 2002, pp. 354-357.

Roesler et al., "Oral vaccination of pigs with an invasive gyrA-cpxA-rpoB *Salmonella typhimurium* mutant". Vaccine, vol. 23, No. 5, Dec. 2004, pp. 595-603.

Rotto, Hans "Diagnosis, Vaccination and Field Experiences with PCV-AD". Iowa Pork Progress, 2007, pp. 1-10.

Rovira et al., "Experimental Inoculation of Conventional Pigs with Porcine Reproductive and Respiratory Syndrome virus and Porcine Circovirus 2", J. Viral, jApr. 2002, vol. 76, No. 7, pp. 3232-3239.

Royer et al., "Susceptibility of porcine circovirus type 2 to commercial and laboratory disinfectants". Journal of Swine Health and Production, vol. 9, No. 6, 2001, pp. 281-284.

Rueda et al., "Effect of Different Baculovirus Inactivation Procedures on the Integrity and Immunogenicity of Porcine Parvovirus-Like Particles", Vaccine, 2001, 19, pp. 726-734.

Schaefer et al., "Characterization and Formulation of Multiple Epitope-Specific Neutralizing Monoclonal Antibodies br Passive Immunization against Cryptosporidiosis". Infection and Immunity, vol. 68, No. 5, May 2000, pp. 2608-2616.

Sedlik et al., "Recombinanat parvovirus-like particles as an antigen carrier: A novel nonreplicative exogenous antigen to elicit protective antiviral cytotoxic T cells". Proceedings of the National Academy of Sciences, vol. 94, Jul. 1997, pp. 7503-7508.

Segales et al., "Changes in Peripheral Blood Leukocyte Populations in Pigs with Natural Postweaning Multisystemic Wasting Syndrome (PMWS)", Vet Immunology & Immunopathology, 2001, 81, pp. 37-44.

Segales et al., "Epidemiology of Porcine Circovirus Type 2 Infection: What do we Know?", Pig News & Information, 2003, vol. 24, No. 4, pp. 103N-110N.

Segales et al., "Granulomatous Enteritis and Lymphadenitis in Iberian Pigs Naturally Infected with Lawsonia intracellularis". Veterinary Pathology, vol. 38, No. 3, 2001, pp. 343-346.

Segales et al., "Pathological findings associated with naturally acquired porcine circovirus type 2 associated disease". Veterinary Microbiology, vol. 98, 2004, pp. 137-149.

Segales et al., "Postweaning Multisystemic Wasting Syndrome (PMWS) in Pigs, A Review", Vet. Quarterly, 2002, 24(3), pp. 109-124.

Segalés et al., "Immunosuppression in postweaning multisystemic wasting syndrome affected pigs". Veterinary Microbiology, vol. 98, 2004, pp. 151-158.

Segalés et al., "Porcine Circovirus Diseases". Diseases of Swine, 9th Edition, Chapter 14, Blackwell Publishing, Ames, Iowa, 2006, pp. 299-307.

Segalés et al., "Postweaning Multisystemic Wasting Syndrome and Porcine Circovirus Ty;e 2: The European Perspective". Trends in

(56) References Cited

OTHER PUBLICATIONS

Emerging Viral Infections of Swine, Ch. 9.3, PMWS and PCV2: European Perspective, 2002, pp. 297-303.
SEQ ID No. 11, Sequence Alignment with UniProt Database Accession No. O91862_PCV2 submitted Nov. 1998 by Meehan et al. (Journal of General Virology, 1998; 79: 2171-2179).
SEQ ID No. 11 Sequence Alignment with Geneseq Database Accession No. AAO23063 submitted Oct. 2003 in WO 2003049703, 2 pages.
SEQ ID No. 5 Sequence Alignment with Geneseq Database Accession No. ABB99415, submitted Jan. 2003 in WO2002/77210, 2 pages.
SEQ ID No. 5 Sequence Alignment with UniProt Database Accession No. Q9YTB6_PCV2 Submitted May 1999 by Fenaux et al. in Journal of Clinical Microbiology, 2000; 38: 2494-2503, 2 pages.
SEQ ID No. 6 Sequence Alignment with Geneseq Database Accession No. ADA9081 submitted Nov. 2003 in USPgPUB 2003/096377, 2 pages.
SEQ ID No. 6 Sequence Alignment with UniProt Database Accession No. Q9YTB6_PCV2 Submitted May 1999 by Fenaux et al. in Journal of Clinical Microbiology, 2000; 38: 2494-2503, 2 pages.
SEQ ID No. 3 Sequence Alignment with Geneseq Database Accession No. ABV72527 submitted Jan. 2003, in WO2002/077210, 3 pages.
SEQ ID No. 4 Sequence Alignment with Geneseq Database Accession No. ABV72527 submitted Jan. 2003, in WO2002/077210, 3 pages.
Shen et al., "Comparison of commercial and experimental porcine circovirus type 2 (PCV2) vaccines using a triple challenge with PCV2, porcine reproductive and respiratory syndrome virus (PRRSV), and porcine parvovirus (PPV)". Vaccine, vol. 28, 2010, pp. 5960-5966.
Sibila et al., "Use of a Polymerase Chain Reaction Assay and ELISA to Monitor Porcine Circovirus Type 2 Infection in Pigs From Farms with and without Postweaning Multisystemic Wasting jSyndrome", AJVR, Jan. 2004, vol. 65, No. 1, pp. 88-92.
Siebel, K. "PCV2 vaccination changing the pig industry Part 2. Global experiences from the field around one-shot vaccination". Pig Progress, vol. 26, No. 1, 2010, pp. 11-13.
Smith et al., "Observations on Experimental Oral Infection with *Salmonella dublin* in Calves and *Salmonella choleraesuis* in Pigs". Journal of Pathology and Bacteriology, vol. 93, No. 1, 1967, pp. 141-156.
Sorden et al., "Development of a Polyclonal-antibody-based Immunohystochemical Method for the Detection of Type 2 Porcine circovirus in Formalin-Fixed, Paraffin-Embedded Tissue", J. Vet Diagn. Inest, 1999, 11, pp. 528-530.
Spier, R.E., "Multivalent Vaccines: Prospects and Challenges". Folia Microbiologica, vol. 42, No. 2, 1997, pp. 105-112.
Suradhat et al., "The influence of maternal immunity on the efficacy of a classical swine fever vaccine against classical swine fever virus, genogroup 2.2, infection". Veterinary Microbiology, vol. 92, 2003, pp. 187-194.
Takada-Iwao et al., "Porcine circovirus type 2 (PCV2) vaccination reduces PCV2 in a PCV2 and *Salmonella enterica* serovar Choleraesuis coinfection model". Veterinary Microbiology, vol. 162, 2013, pp. 219-223.
Thacker et al., "Effect of vaccination on the potentiation of porcine reproductive and respiratory syndrom virus (PRRSV)-induced pneumonia by Mycoplama hyopneumoniae". Vaccine, vol. 18, 2000, pp. 1244-1252.
Thacker, Eileen L., "Diagnosis of Mycoplama hyopneumoniae". Journal of Swine Health Production, vol. 12, No. 5, 2004, pp. 252-254.
Thacker, Eileen L., "Mycoplasmal Diseases". Diseases of Swine, 9th Edition, Ch. 42, 2006, pp. 701-717.
Truong et al., "Identification of an immunorelevant ORF2 epitope from porcine circovirus type 2 as a serological marker for experimental and natural infection". Archives of Virology, vol. 146, 2001, pp. 1197-1211.

UniProt Database Accession No. O91862 submitted Nov. 1, 1998 by Meehan et al., Characterization of novel circovirus DNAs associated iwth wasting sydromes in pigs. Journal of General Virology, 1998; 79: 2171-2179, 1 page.
UniProt Database Accession No. Q9YTB6, Direct Submission, Wang et al., May 1, 1999 , 1 page.
Vansickle, J., "Circovirus Grips Industry". Jul. 15, 2006, National Hog Farmer.
Vasconcelos et al., "Swine and Poultry Pathogens: the Complete Genome Sequences of Two Strains of Mycoplasma hyopneumoniae and a Strain of Mycoplasma synoviae". Aug 2005, Journal of Bacteriology, vol. 187, No. 16, pp. 5568-5577.
VIDO Swine Technical Group—Linking Knowledge to practical solutions "Vaccination Guidelines for Swine". Jun. 2004, www.vido.org.
Vincent et al., "Dendritic Cells Harbor Infetious Porcine Circovirus Type 2 in the Abscence of Apparent Cell Modulation or Replication of the Virus". Dec. 2003, Journal of Virology, vol. 77, No. 24, pp. 13288-13300.
Walker, et al., "Development and application of a competitive enzyme-linked immunosorbent assay for the detection of serum antibodies to porcine circovirus type 2". 2000, Journal of Veterinary Diagnostic Investigation, vol. 12, pp. 400-405.
Wan et al., "Comprehensive Prevention and Control Techniques for Porcine Circovirus Type 2 Infection". Chinese Swine Industry, No. 3, 2006, pp. 42-45.
Wang et al. "Construction and immunogenicity of recombinant adenovirus expressing the capsid protein of porcine circovirus 2 (PCV2) in mice". Vaccine, vol. 24, 2006, pp. 3374-3380.
Web site: "Does stress-free livestock mean safer food?" http://www.foodnavigator.com/Financial-Industry/Does-stress-free-livestock-mean-safer-food Accessed on: Jun. 4, 2004.
Weibel, Helen, "A field efficacy study with Enterisol® Ileitis and Ingelvac CircoFLEX® in Switzerland". Universität Zurich, 2009, 1 page. [Accessed at: http://www.vet.uzh.ch/dissertationen/diss_anzeige.php?ID=724&sprache=e on Jun. 7, 2013].
Fachinger et al., "The effect of vaccination against porcine circovirus type 2 in pigs suffering from porcine respiratory disease complex". 2008, Vaccine, vol. 26, pp. 1488-1499.
Fan et al., "Immunogenicity of Empty Capsids of Porcine Circovirus Type 2 Produced in Insect Cells". 2007, Veterinary Research Communications, vol. 31, pp. 487-496.
Fan et al., "Preclinical study of influenza virus A M2 peptide conjugate vaccines in mice, ferrets, and rhesus monkeys". Vaccine, vol. 22, 2004, pp. 2993-3003.
Fan et al., "The Expression of Porcine Circovirus Type 2 ORF2 Gene in Insect Cells and its Character". Chinese Journal of Biotechnology, vol. 21, No. 6, Nov. 2005, pp. 975-978.
Fenaux et al., "A Chimeric Porcine Circovirus (PCV) with the Immunogenic Capsid Gene of the Pathogenic PCV Type 2 (PCV2) Clones into the Genomic Backbone of the Nonpathogenic PCV1 Induces Protective Imunity Against PCV2 Infection in Pigs", J. Viral, Jun. 2004, vol. 78, No. 12, pp. 6297-6303.
Fenaux et al., "Genetic Characterization of Type 2 Porcine Circovirus (PCV-2) from Pigs with Postweaning Multisystemic Wasting Syndrome in Different Geographic Regions of North America and Development of a Differential PCR-Restriction Fragment Length Polymorphism Assay to Detect and Differentiate between Infections with PCV-1 and PCV-2". Journal of Clinical Microbiology, vol. 38, No. 7, Jul. 2000, pp. 2494-2503.
Fenaux et al., "Immunogenicity and Pathogenicity of Chimeric Infectious DNA Clones of Pathogenic Porcine Circovirus Type 2 (PCV2) and Nonpathogenic PCV1 in Weanling Pigs". Journal of Virology, vol. 77, No. 20, Oct. 2003, pp. 11232-11243.
Fort et al., "Porcine circovirus type 2 (PCV2) vaccination of conventional pigs prevents viremia against PCV2 isolates of different genotypes and geographic origins". Vaccine, vol. 26, No. 8, 2008, pp. 1063-1071.
Gagrcin et al., "Complex of Swine Respiratory Diseases-Strategy of control in light of latest knowledge". Veterinarski Glasnik, vol. 58, No. 7-8, 2004, pp. 409-418. [English Abstract at p. 417.].
Genbank Accession No. AAC61738, Version AAC61738.1 GI:3661517, Sep. 29, 1998.

(56) References Cited

OTHER PUBLICATIONS

GenBank Accession No. AF201311, Direct Submission, submitted Feb. 23, 2000 in Mankertz et al., "Characterization of PCV-2 isolates from Spain, Germany and France", Virus Research, vol. 66, No. 1, 2000, pp. 65-77, 2 pages.
Genbank Accession# AAF87231.1, PCV2 ORF2 Protein, 2000.
Gizurarson, Sveinbjörn, "Clinically Relevant Vaccine-Vaccine Interactions". BioDrugs, vol. 9, No. 6, Jun. 1998, pp. 443-453.
Groner, et al., The Biology of Baculoviruses, vol. 1, Biological Properties and Moleculary Biology, 1986, Chapter 3, Specificity and Safety of Baculoviruses, pp. 177-202.
Gualandi et al., "The Ability by Different Preparations of Porcine Parvovirus to Enhance Humoral Immunity in Swine and Guinea Pigs". Microbiologica, vol. 11, No. 4, 1988, pp. 363-369.
Gualandi et al., "The Response of Pregnant Gilts Previously Given an Inactivated Preparation of Porcine Parvovirus (PPV) to Challenge Infection with a Fully Virulent PPV". Microbiologica, vol. 15, 1992, pp. 391-396.
Ha et al., "Outbreak of salmonellosis in pigs with postweaning multisystemic wasting syndrome". Veterinary Record, vol. 156, No. 18, Apr. 2005, pp. 583-584.
Haake et al., "Influence of age on the effectiveness of PCV2 vaccination in piglets with high levels of maternally lerived antibodies". Veterinary Microbiology, vol. 168, 2014, pp. 272-280.
Haiwick et al., "Trivalent vaccine mixture protects against simultaneous challenge with M. hyopneumoniae, PCV2, and PRRS virus". Allen D. Leman Swine Conference, 2010, p. 176.
Hamel et al., "Nucleotide Sequence of Porcine Circovirus Associated with Postweaning Multisystemic Wasting Syndrome in Pigs". Journal of Virology, vol. 72, No. 6, Jun. 1998, pp. 5262-5267.
Harding et al., "Recognizing and diagnosing postweaning multisystemic wasting syndrome (PMWS)". Swine Health and Production, vol. 5, No. 5, 1997, pp. 201-203.
Harms et al., "Three cases of porcine respiratory disease complex associated with porcine circovirus type 2 infection". Journal of Swine Health and Production, vol. 10, No. 1, 2002, pp. 27-30.
Haruna et al., "The role of immunostimulation in the development of postweaning multisystemic wasting syndrome in gigs under field conditions". Canadian Journal of Veterinary Research, vol. 70, Oct. 2006, pp. 269-276.
Hilgers et al., "Alkyl-esters of polyacrylic acid as vaccine adjuvants". Vaccine, vol. 16, No. 16, 1998, pp. 1575-1581.
Hirai et al., "Dual infection with PCV-2 and porcine epidemic diarrhoea virus in neonatal piglets". The Veterinary Record, vol. 148, 2001, pp. 482-484.
Hoogland et al., "Effects of adjuvants on porcine circovirus type 2-associated lesions". Journal of Swine Health and 'reduction, vol. 14, No. 3, 2006, pp. 133-139.
Huang et al., "Porcine circovirus type 2 (PCV2) infection decreases the efficacy of an attenuated classical swine fever virus (CSFV) vaccine". Veterinary Research, vol. 42, 115, 2011, pp. 1-9.
Hüser et al., "Baculovirus Vectors: Novel Mammalian Cell Gene-Delivery Vehicles and Their Applications". American Journal of Pharmacogenomics, vol. 3, No. 1, 2003, pp. 53-63.
International Search Report and Written Opinion for PCT/US2008/088678 dated Jun. 4, 2009.
Numaru et al., "Expression of biologically active recombinant porcinee GM-CSF by baculovirus gene expression system". 1998, Immunology and Cell Biology, vol. 76, pp. 195-201.
Invitrogen Life Technologies, "Growth and Maintenance of Insect Cell Lines". Insect Cell Lines Manual, Version K, Jul. 12, 2002, pp. 1-34. [Accessed at http://www.med.unc.edu/pharm/sondeklab/Lab%20Resources/manuals/insect_cell_manual.pdf on Nov. 25, 2013].
Iowa State University, "Lyphoid Depletion: PCV2-Associated Lymphoid Depletion"., 2013, pp. 1-2. [Accessed at: http://vetmed.iastate.edu/research/labs/pcv2/pcv2-associated-disease/lymphoid-depleti . . . on Dec. 14, 2013].

Jensen et al., "Distinction between Porcine Circovirus Type 2 Enteritis and Porcine Proliferative Enteropathy caused by Lawsonia intracellularis". Journal of Comparative Pathology, vol. 135, 2006, pp. 176-182.
Jiang et al., "Expression, Self-Assembly, and Antigenicity of the Norwalk Virus Capsid Protein". Journal of Virology, vol. 66, No. 11, Nov. 1992, pp. 6527-6532.
Jiang et al., "Synthesis of rotavirus-Like Particles in Insect Cells: Comparative and Quantitative Analysis". Biotechnology and Bioengineering, vol. 60, No. 3, 1998, pp. 369-374.
Ju et al., "Immunogenicity of a recombinant pseudorabies virus expressing ORF1-ORF2 fusion protein of porcine circovirus type 2". 2005, Veterinary Microbiology, vol. 109, pp. 179-190.
Kamstrup, et al., "Immunisation against PCV2 structural protein by DNA vaccination of mice". 2004, Vaccine, vol. 22, pp. 1358-1361.
Kapust et al., "*Escherichia coli* maltose-binding protein is uncommonly effective at promoting the solubility of polypeptides to which it is fused". Protein Science, vol. 8, 1999, pp. 1668-1674.
Kennedy et al., "Repdocution of Lesions of Postweaning Multisystemic Wasting Syndrome by Infection of Conventional Pigs with Porcine Circovirus Type 2 Alone or in a Combination with Porcine Parvovirus". Journal of Comparative Pathology, vol. 122, 2000, pp. 9-24.
Kim et al., "A comparison of the Lymphocyte Subpopulations of Pigs Experimentally Infected with Porcine Circovirus 2 and/or Parvovirus". 2003, The Veterinary Journal, vol. 165, pp. 325-329.
Kim et al., "Association of Porcine Circovirus 2 with Porcine Respiratory Disese Complex", The Vet. Jour., 2003, 166, pp. 251-256.
Kim et al., "Characterization of the Recombinant Proteins of Porcine Circovirus Type2 Field Isolate Expressed in the Baculovirus System". 2002, Journal of Veterinary Science, vol. 3, No. 1, pp. 19-23.
Kim et al., "Efficacy of different disinfectants in vitro against porcine circovirus type 2". The Veterinary Record, vol. 164, May 2009, pp. 599-600.
Kim et al., "Enteritis associated with prcine circovirus 2 in pigs". 2004, The Canadian Journal of Veterinary Research, vol. 68, pp. 218-221.
Kiupel, M. "Postweaning Multisystemic Wasting Syndrome (PMWS) in pigs". Production diseases in Farm Animals, 12th International Conference, Section D, Wageningen Academic Publishers, The Netherlands, 2006, pp. 74-89.
Kixmoller et al., "Reduction of PMWS-associated clinical signs and co-infections by vaccination against PCV2". 2008, Vaccine, vol. 26, pp. 3443-3451.
Kost, et al., "Recombinant baculoviruses as mammalian cell gene-delivery vectors". Apr. 2002, Trends in Biotechnology, vol. 20, No. 4, pp. 173-180.
Kovacs et al., "The live attenuated bovine viral diarrhea virus components of a multi-valent vaccine confer protection against fetal infection". Veterinary Microbiology, vol. 96, 2003, pp. 117-131.
Krakowka et al., "Features of porcine circovirus-2 disease: correlations between lesions, amount and distribution of virus, and clinical outcome". Journal of Veterinary Diagnostic Investigation, vol. 17, No. 3, May 2005, pp. 213-222.
Kyriakis et al., "The Effects of Immuno-modulation of the Clinical and Pathological Expression of Postweaning Multisystemic Wasting Syndrome". 2002, Journal of Comparative Pathology, vol. 126, pp. 38-46.
Kyriazakis et al., "The Maintenance of Health". Whittemore's Science and Practice of Pig Production, Third Edition, chapter 7, Blackwell Publishing Ltd., Oxford, UK, 2006, pp. 263-316.
Ladekjaer-Mikkelsen et al., "Reproduction of postweaning multisystemic wasting syndrome (PMWS) in immunostimulated and non-immunostimulated 3-week-old piglets experimentally infected with prcine circovirus type 2 (PCV2)". 2002, Veterinary Microbiology, vol. 89, pp. 97-114.
Lekcharoensuk et al., "Epitope Mapping of the Major Capsid Protein of Type 2 Porcine Circovirus (PCV2) by Using Chimeric PCV1 and PCV2". Journal of Virology, vol. 78, No. 15, Aug. 2004, pp. 8135-8145.

(56) References Cited

OTHER PUBLICATIONS

Li et al., "Expression and Self-Assembly of Empty Virus-Like Particle of Hepatitis E Virus". Journal of Virology, vol. 71, No. 10, Oct. 1997, pp. 7207-7213.
Lin et al., "Mycoplasma hyorhinis in Taiwan: Diagnosis and isolation of swine pneumonia pathogen". Veterinary Microbiology, vol. 115, 2006, pp. 111-116.
Liu et al., "Bacterial Expression of an Immunologically Reactive PCV2 ORF2 Fusion Protein". 2001, Protein Expression and Purification, vol. 21, pp. 115-120.
Liu et al., "Characterization of a Previously Unidentified Viral Protein in Porcine Circovirus Type 2-Infected Cells and Its Role in Virus-Induced Apoptosis". Jul. 2005, Journal of Virology, vol. 79, No. 13, pp. 8262-8274.
Liu et al., "Development of an ELISA Based on the Baculovirus-Expressed Capsid Protein of Porcine Circovirus Type 2 as Antigen". Journal of Veterinary Medical Science, vol. 66, No. 3, 2004, pp. 237-242.
Mackinnon, J.D., "Vaccination Ramification? An Objective Look at How Vaccination Might Affect Post-Weaning Multisystemic Wasting Syndrome (PMWS) and Porcine Dermatitis and Nephropathy Syndrome (PDNS)". 2003, The Pig Journal, vol. 51, pp. 36-63.
Maes et al., "Effect of vaccination against Mycoplasma hyopneumoniae in pig herds with an all-in/all-out production system". Vaccine, vol. 17, 1999, pp. 1024-1034.
Mahe et al., "Differential recognition of ORF2 protein from type 1 and type 2 porcine circoviruses and identification of immunorelevant epitopes". 2000, Journal of General virology, vol. 81, pp. 1815-1824.
Maranga et al., "Virus-Like Particle Production at Low Multiplicities of Infection With the Baculovirus Insect Cell System". Aug 2003, Biotechnology and Bioengineering, vol. 84, No. 2, pp. 246-253.
Martelli et al., "One dose of a porcine circovirus 2 subunit vaccine induces humoral and cell-mediated immunity and protects against porcine circovirus-associated disease under field conditions". Veterinary Microbiology, vol. 149, 2011, pp. 339-351.
Mateu et al., "A Single Amino Acid substitution Affects Multiple Overlapping Epitopes in the Major Antigenic Site of Foot-and-Mouth Disease Virus of Serotype C," Journal of General Virology, vol. 71, 1990, pp. 629-637.
McKeown et al., "Effects of Porcine Circovirus Type 2 (PCV2) Maternal Antibodies on Experimental Infection of Piglets with PCV2". Clinical and Diagnostic Laboratory Immunology, vol. 12, No. 11, Nov. 2005, pp. 1347-1351.
McNeilly et al., "Evaluation of a Porcine Circovirus Type 2-Specific Antigen-Captive Enzyme-Linked Immunosorbent Assay for the Diagnosis of Postweaning Multisystemic Wasting Syndrome in Pigs: Comparison with Virus Isolation, Immunohistochemistry, and the Polymerase Chain Reaction", J. Vet Diagn. Invest, 2002, 14, pp. 106-112.
Meehan et al., "Characterization of novel circovirus DNAs associated with wasting syndromes in pigs". Journal of General Virology, vol. 79, 1998, pp. 2171-2179.
Minion et al., "Then Genome Sequence of Mycoplasma hyopneumoniae Strain 232, the Agent of Swine Mycoplasmosis". Nov. 2004, Journal of Bacteriology, vol. 186, No. 21, pp. 7123-7133.
Morales et al., "Serendipitous Discovery and X-Ray Structure of a Human Phosphate Binding Apolipoprotein". Mar 2006, Structure, vol. 14, pp. 601-609.
Morris et al., "Characterization of Productive and Non-Productive ACMNPV Infection in Selected Insect Cell Lines", Viro. 197, 1993, pp. 339-348.
Morris et al., "Promoter Influence on Baculovirus-Mediated Gene jExpression in Permissive and Nonpermissive Insect Cell Lines", J. Virol., Dec. 1992, vol. 66, No. 12, pp. 7397-7405.
Mortola et al., "Efficient assembly and release of SARS coronavirus-like particles by a heterologous expression system". FEBS Letters, vol. 576, 2004, pp. 174-178.
Muirhead, Mike, "Sources of information on PMWS/PDNS". The Veterinary Record, vol. 150, No. 14, Apr. 6, 2002, p. 456.
Murakami et al., "Occurrence of Swine Salmonellosis in Postweaning Multisystemic Wasting Syndrome (PMWS) Affected Pigs Concurrently Infected with Porcine Reproduction and Respiratory Syndrome Virus (PRRSV)". Journal of Veterinary Medical Science, vol. 68, 2006, pp. 387-391.
Nawagitgul et al., "Open reading frame 2 of porcine circovirus type 2 encodes a major capsid protein". 2000, Journal of General Virology, vol. 81, pp. 2281-2287.
Nawagitgul et al., Modified Indirect Porcine Circovirus (PCV) Type 2-based and Recombinant Capsid Protein (ORF-2) Based Enzyme-Linked Immunosorbent Assays for Detection of Antibodies to PCV, Clinical and Diagnostic Laboratory Imunology, Ja. 2002, vol. 9, No. 1, pp. 33-40.
Neutra et al., "Optimization of protein-production by the baculovirus expression vector system in shake flasks". Applied Microbiology and Biotechnology Journal, vol. 37, No. 1, 1992, pp. 74-78.
Noad et al. "Virus-like particles as immunogens" Trends in Microbiology, vol. 11, No. 9, Sep. 2003, pp. 438-444.
O'Dea et al., "Porcine circovirus-associated disease in weaner pigs in Western Australia". Australian Veterinary Journal, vol. 89, No. 4, Apr. 2011, pp. 122-130.
Ohnesorge et al., "Efficacy Studies—Efficacy evaluation of a mixed Mycoplasma hyopneumoniae bacterin and a porcine circovirus type 2 vaccine". 2007, 1 page. [Accessed at http://www.ingelvacflex.co.uk/mycoflex/research/efficacy.php on Jul. 31, 2012].
Okuda, et al., "Experimental Reproduction of Post-Weaning Multisystemic Wasting Syndrome in Cesarean-Derived, Colostrum-Deprived Piglets Inoculated with Porcine Circovirus Type 2 (PCV2): Investigation of Quantitative PCV2 Distribution and Antibody Responses", J. Vet Diagn. Invest, 2003, 15, pp. 107-114.
Olvera et al., "Comparison of porcine circovirus type 2 load in serum quantified by a real time PCR in postweaning multisystemic wasting syndrome and porcine dermatitis and nephropathy syndrome naturally affected pigs". 2004, Journa of Virological Methods, vol. 117, pp. 75-80.
Opriessnig et al., "A commercial vaccine based on PCV2a and an experimental vaccine based on a variant mPCV2b are both effective in protecting pigs against challenge with a 2013 U.S. variant mPCV2b strain". Vaccine, vol. 32, No. 2, 2014, pp. 230-237.
Opriessnig et al., "A PCV2 vaccine based on genotype 2b is more effective than a 2a-based vaccine to protect against PCV2b or combined PCV2a/2b viremia in pigs with concurrent PCV2, PRRSV and PPV infection". Vaccine, vol. 31, 2013, pp. 487-494.
Opriessnig et al., "Comparison of Molecular and Biological Characteristics of a Modified Live Porcine Reproductive and Respiratory Syndrome Virus (PRRSV) Vaccine (Ingelvac PRRS MLV), The Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Derivation of porcine circovirus type 2-negative pigs from positive breeding herds". Journal of Swine Health and Production, vol. 12, No. 4, Jul. and Aug. 2004, pp. 186-191.
Opriessnig et al., "Differences in virulence among porcine circovirus type 2 isolates are unrelated to cluster type 2a pr 2b and prior infection provides heterologous protection". Journal of General Virology, vol. 89, No. 10, 2008, pp. 2482-2491.
Opriessnig et al., "Effect of porcine circovirus type 2 (PCV2) vaccination on porcine reproductive and respiratory syndrome virus (PRRSV) and PCV2 coinfection". Veterinary Microbiology, vol. 131, 2008, pp. 103-114.
Opriessnig et al., "Effect of Vaccination with Selective Bacterins on Conventional Pigs Infected with Type 2 Porcine Circovirus". Veterinary Pathology, vol. 40, 2003, pp. 521-529.
Opriessnig et al., "Effects of the timing of the administration of Mycoplasma hyopneumoniae bacterin on the development of lesions associated with porcine circovirus type 2". Veterinary Record, vol. 158, No. 5, Feb. 2006, pp. 149-154.
Opriessnig et al., "Experimental Co-Infection with Porcine Circovirus Type 2 and *Salmonella typhimurium* or *Lawsonia Intracellularis*". Pig Progress, Jun. 2008, 1 page. [Accessed at:

(56) References Cited

OTHER PUBLICATIONS http://www.pigprogress.net/public/file/IPVS-oral%20presentations/Viral%20diseases/Experimental%20co-infection%20with%20PCV2%20and%20salmonella%20Typhimurium%20or%20lawsonia%20intracellularis.pdf on Mar. 17, 2010].

Opriessnig et al., "Experimental Reproduction of Postweaning Multisystemic Wasting Syndrome in Pigs by Dual nfection with Mycoplasma hyopneumoniae and Porcine Circovirus Type 2". Veterinary Pathology, vol. 41, No. 6, Nov. 2004, pp. 624-640.

Opriessnig et al., "Porcine Circovirus Type 2 Infection Decreases the Efficacy of a Modified Live Porcine Reproductive and Respiratory Syndrome Virus Vaccine", Clinical and Vaccine Immunology, Aug. 2006, vol. 13, No. 8, pp. 923-929.

Ostanello et al., "Experimental infection of 3-week-old conventional colostrum-fed pigs with porcine circovirus type 2 and porcine parvovirus". Veterinary Microbiology, vol. 108, no. 3-4, Jul. 2008, pp. 179-186.

Paterson, J.E., "Health and antimicrobial resistance". Manipulating Pig Production X, Chapter 2, Proceedings of the Tenth Biennial Conference of the Australasian Pig Science Association (Inc.) (APSA) held in Christchurch, New Zealand on Nov. 27 to 30, 2005, Werribee, Victoria, Australia: Australasian Pig Association (Inc.), pp. 21-74.

Patterson et al., "Baculovirus and Insect Cell Gene Expression: Review of Baculovirus Biotechnology". Environmental Health Perspectives, vol. 103, Nos. 7-8, Jul.-Aug. 1995, pp. 756-759.

Patterson et al., "Interlaboratory Comparison of Porcine Circovirus-2 Indirect Immunofluorescent Antibody Test and Enzyme-Linked Immunosorbent Assay Results on Experimentally Infected Pigs". Journal of Veterinary Diagnostic Investigation, vol. 23, 2011, pp. 206-212.

Poljak et al., "Spread of porcine circovirus associated disease (PCVAD) in Ontario (Canada) swine herds: Part I. Exploratory spatial analysis". BMC Veterinary Research, vol. 6, No. 59, 2010, pp. 1-15.

Poppe et al., "*Salmonella typhimurium* DT104: A virulent and drug-resistant pathogen". Canadian Veterinary Journal, vol. 39, 1998, pp. 559-565.

Quintana et al., "Clinical and pathological observations on pigs with postweaning multisystemic wasting syndrome". 2001, The Veterinary Record, vol. 149, pp. 357-361.

Bandrick et al., "Colostral antibody-mediated and cell-mediated immunity contributes to innate and antigen-specific mmunity in piglets." Developmental and Comparative Immunology, vol. 43, 2014, pp. 114-120.

Hodgins et al., "Influence of age and maternal antibodies on antibody responses of neonatal piglets vaccinated against Mycoplasma hyopneumoniae." Journal of Swine Health and Production, vol. 12, No. 1, Jan.-Feb. 2004, pp. 10-16.

"Directive 2001/82/EC of the European Parliament and of the Council of Nov. 6, 2001 on the Community code relating to veterinary medicinal products." Official Journal of the European Communities, L 311, Nov. 2001, pp. 1-66.

Berinstein et al., "Mucosal and systemic immunization elicited by Newcastle disease virus (NDV) transgenic plants as antigens." Vaccine, vol. 23, 2005, pp. 5583-5589.

Rota et al., "Expression of influenza A and B virus nucleoprotein antigens in baculovirus." Journal of General Virology, vol. 71, 1990, pp. 1545-1554.

Hu et al., "Baculovirus as a highly efficient expression vector in insect and mammalian cells." Acta Pharmacologica Sinica, vol. 26, No. 4, Apr. 2005, pp. 405-416.

King et al., "Insect cell culture media and maintenance of insect cell lines." The Baculovirus Expression System: A laboratory guide, First Edition, Springer-Science + Business Media, B.V., 1992, pp. 75-79.

Yamaji et al., "Optimal Production of Recombinant Protein by the Baculovirus-Insect Cell System in Shake-Flask culture with Medium Replacement." Journal of Bioscience and Bioengineering, vol. 87, No. 5, 1999, pp. 636-641.

McCall et al., "Improvements to the throughput of recombinant protein expression in the baculovirus/insect cell system." Protein Expression and Purification, vol. 42, 2005, pp. 29-36.

Wikipedia "Specific-pathogen-free". Wikipedia, The Free Encyclopedia, May 28, 2016, at 04:21, pp. 1-3 [Accessed at https://en.wikipedia.org/w/index.php?title=Specific-pathogen-free&oldid=722441484 on Jun. 27, 2016.

Spear, Maynard L., "Specific Pathogen Free Swine." iowa State University Veterinarian, vol. 22, Iss. 3, Article 2, 1960, pp. 134, 136-137.

Safron et al., "The SPF Pig in Research." ILAR Journal, vol. 38, No. 1, 1997, pp. 28-31.

Midwest Research Swine, "High Health Heard Status." pp. 1-2. [Accessed at: http://midwestresearchswine.com/herd-health/high-health-herd-status/ on Jun. 27, 2016].

Cariolet et al., "Rappel Des Differentes Méthodes D'Obtention de Porcelets Assainis: Conditions de Maintien Du Statut Sanitaire et Valorisation de ces Animaux." Journees Rech. Porcine en France, vol. 26, 1994, pp. 1-12. (Abstract in English on p. 1).

Allan et al., "Neonatal Vaccination for Mycoplasma Hyopneumoniae and Post-Weaning Multisystemic Wasting Syndrome: A Field Trial." The Pig Journal, vol. 48, 2001, pp. 34-41.

Meerts et al., "Correlation Between Type of Adaptive Immune Response Against Porcine Circovirus Type 2 and Level of Virus Replication." Viral Immunology, vol. 18, No. 2, 2005, pp. 333-341.

Meerts et al., "Correlation between the prsence of neutralizing antibodies against porcine circovirus 2 (PCV2) and protection against replication of the virus and development of PCV2-associated disease." BMV Veterinary Research, vol. 2, No. 6, 2006, pp. 1-11.

Newiesk, Stefan, "Maternal antibodies: clinical significance, mechansim of interference with immune responses, and possible vaccination strategies." Frontiers in Immunology, vol. 5, Article 446, Sep. 2014, pp. 1-15.

Cutts et al., "Immunogenicity of high-titre AIK-C or Edmonston-Zagreb vaccines in 3.5-month-old infants, and of medium- or high-titre Edmonston-Zagreb vaccine in 6-month-old infants, in Kinshasa, Zaire." Vaccine, vol. 12, No. 14, 1994, pp. 1311-1316.

Knudsen et al., "Child Mortality Following Standard, Medium or High Titre Measles Immunization in West Africa." International Journal of Epidemiology, vol. 25, No. 3, 1996, pp. 665-673.

"5.2.9 Evaluation of Saftey of Each Batch of Veterinary Vaccines and Immunosera." European Pharmacopoeia, 5th Edition, Strasbourg: Council of Europe, 2005, pp. 2829-2830.

Boehringer Ingelheim, "Preventing disease: One billion pigs vaccinated with Ingelvac CircoFLEX®" Feb. 14, 2013, pp. 1-3. [Available at: https://www.boehringer-ingelheim.com/press-release/preventing-disease-one-billion-pigs-vaccinated-ingelvac-circoflex].

Boehringer Ingelheim Vetmedica, Inc., "Ingelvacâ Circoflexä Safety Data Sheet" Apr. 27, 2015, pp. 1-6.

McNair et al., "Interlaboratory testing of porcine sera for antibodies to porcine circovirus type 2." Journal of Veterinary Diagnositc Investigation, vol. 16, 2004, pp. 164-166.

Oraganoiu et al., "Carbomer." Feb. 2009, pp. 110-114. [Retrieved at: http://drugs-nutrition.com/download/Handbook_of_excipients_6/Carbober.pdf on Sep. 23, 2015.].

Cameo "Carbopol®". Wikipedia, The Free Encyclopedia, Jul. 24, 2013, at 06:59, pp. 1-2 [Accessed at https://http://cameo.mfa.org/index.php?title=Carbopol®&oldid=22637on Sep. 23, 2015].

Liesner et al., "Efficacy of Ingelvac CircoFLEX® in face of maternal antibodies in a field trial in France." 2008 Allen J. Leman Swine Conference—Recent Research Reports, p. 9.

"Reflection paper on the demonstration of a possible impact of maternally derived antibodies on vaccine efficacy in young animals." Europan Medicines Agency: Science Medicines Health, Mar. 15, 2010, pp. 1-5.

European Medical Agency, "Annex I: Summary of Product Characteristics: Suvaxyn PCV Suspension for injection for pigs". EPAR Product Information, Last Updated Jun. 4, 2017, pp. 1-22. [Accessed at: http://www.ema.europa.eu/docs/en_GB/document_library/EPAR_-_Product_Information/veterinary/000149/WC500069200.pdf].

(56) References Cited

OTHER PUBLICATIONS

Larochelle et al., "Comparative serologic and virologic study of commerical swine herds with and without postweaning multisystemic wasting syndrom." The Canadian Journal of Veterinary Research, vol. 67, 2003, pp. 114-120.
Eddicks et al., "Low prevalence of porcine circovirus type 2 infections in farrowing sows and corresponding pre-suckling piglets in southern German pig farms." Veterinary Microbiology, vol. 187, 2016, pp. 70-74.
Boehringer Ingelheim Vetmedica GmbH, "Our conviction regarding PRRS-only facts count!" Oct. 2003, pp. 1-3.
Jensen, Poul Moesgaard, "The Danish SPF-System Developments and challenges in the future.", 2013, 18 pages. [Accessed at: http://giqs.org/fileadmin/web_giqs/content/PDFs/PDFs_Quarisma/projektplatfform/PDF_neu2013/SPF-Sundhedsstyringen_2013_QUARISMA_Holland.pdf].
Eichmeyer, Marc, "Summary of Study No. 6131-0981-04P-047 (Overdose Study)" Boehringer Ingelheim Vetmedmica, Inc., Mar. 11, 2010, pp. 1-2.
Halbur et al., "Porcine Circovirus Associated Disease (PCVA) . . . a "Double Bogey"." Carthage Veterinary Service ltd. 16th Annual Swine Conference, Jan. 1, 2006, 3 pages. [Accessed at http://www.prairieswine.com/porcine-circovirus-associated-disease-pcva%E2%80%A6-a-%E2%80%9Cdouble-bogey%E2%80%9D/ on Sep. 1, 2015].
Eichmeyer, Marc, "Annex 1 of PCV-2 Study" Jan. 2012, pp. 1-2.
Eichmeyer, Marc, "Summary of Study No. 6127-0981-08P-044 (Efficacy Study)" Boehringer Ingelheim Vetmedica, Inc., Mar. 11, 2010, pp. 1-2.
9 C.F.R. Ch. 1 (Jan. 1, 2006 Edition) §112.7(f), Animal and Plant Health Inspection Service, USDA, 1 page.
Jensen, Poul Moesgaard, "The Danish SPF-Sytem Developments and challenges in the future." Quarisma-Workshop, May 16, 2013, pp. 1-18. [Accessed at: http://giqs.org/fileadmin/web_giqs/content/PDFs/PDFs_Quarisma/projektplattform/PDF_neu2013/SPF-Sundhedsstyringen_2013_QUARISMA_Holland.pdf].
European Medicines Agency, "Ingelvac CircoFLEX: Procedureal steps taken and scientific information after the authorisation." 2015, pp. 1-3. [http://www.ema.europa.eu/docs/en_GB/document_library/EPAR_-_Procedural_steps_taken_and_scientitic_ information_after_authorisation/veterinary/000126/WC500062387.pdf].
European Medicines Agency, "I. Background information on the Procedure." 2008, 2 pages. [Accessed at: http://www.ema.europa.eu/docs/en_GB/document_library/EPAR_-_Procedural_steps_taken_before_authorisation/veterinary/000126/WC500062386.pdf].
European Medicines Agency, "Scientific Discussion." 2008, pp. 1-18. [Accessed at: http://www.ema.europa.eu/docs/en_GB/document_library/EPAR_-_Scientific_Discussion/veterinary/000126/WC500062385.pdf].
Eichmeyer, Marc, "PCV-2 Study." Boehringer Ingelheim Vetmedica, Inc., Jan. 2012, pp. 1-4.
Boehringer Ingelheim Vetmedica, Inc., "ReproCyc® PRRS-PLE", 2011, p. 1 [Accessed at: http://bi-vetmedica.com/product/reprocyc-prrs-ple on Apr. 12, 2011].
Eichmeyer, Marc, "Efficacy of PPRS Antigen in a Combination Vaccne." Boehringer Ingelheim Vetmedica, Inc., Study No. 6131-0852-06P-072, Ingelvac® PRRS MLV Combination Vaccine Efficacy Study, Aug. 19, 2010, pp. 1-4.
Eichmeyer, Marc, "Efficacy of a PCV-2 Antigen in a Combination Vaccne." Boehringer Ingelheim Vetmedica, Inc., Study No. 6131-0981-05P-022, PCV2 Combination Efficacy Study, Aug. 19, 2010, pp. 1-3.
Eichmeyer et al., "Evaluation of Ingelvac® 3FLEX: Demonstration of efficacy for the mixture of Ingelvac® PRRS MLV when rehydrated with Ingelvac CircoFLEX® and Ingelvac MycoFLEX®". 2010 American Association of Swine Veterinarians Annual Conference, Mar. 6-9, 2010, pp. 1-5.
Charles River Laboratories International, Inc., "Indirect Fluorescent Antibody (IFA) Assay." Technical Sheet, V.2, 2011, pp. 1-2.
Robinson et al., "Immunofluorescence." IHC Staining Methods, Fifth Edition, Chapter 10, 2009, pp. 61-65.
Thomas et al., "Effect of PCV2 passive antibody levels on immunization with chimeric PCV1-2 vaccine and challenge with wild-type PCV2." American Association of Swine Veterinarians, 2005, pp. 23-25.
Vicente et al., "Epidemiological Study on Porcine Circovirus type 2 (PCV2) Infection in the European Wild Boar (Sus scrofa) in Spain." Proceedings of the 18th IPVS Congress, vol. 1, Hamburg, Germany, 2004, p. 9.
Opriessnig et al., "Influence of anti-PCV2 passively-acquired antibodies on efficacy of Suvaxyn® PCV2 vaccination in pigs experimentally-infected with PCV2." American Association of Swine Veterinarians, 2007, pp. 299-300.
Boehringer Ingelheim Vetmedica, Inc. "Ingelvace CircoFLEX™ Symposium." Sep. 15, 2007, St. Paul, Minnesota, pp. 1-8. [Accessed at http://animal-health-online.de/circovirus_01/docs/leman_circo.pdf].
Grau-Roma et al., "Recent advances in the epidemiology, diagnosis and control of diseases caused by porcine circovirus type 2." The Veterinary Journal, vol. 187, 2011, pp. 23-32.
Hallsworth et al., "Limits of life in MgCl2-containing environments: chaotropicity defines the window." Environmental Microbiology, vol. 9, No. 3, 2007, pp. 801-813.
Han et al., "Self-Assembly of the Recombinant Capsid Protein of a Bovine Norovirus (BoNV) into Virus-Like Particles and Evaluation of Cross-Reactivitiy of BoNV with Human Noroviruses." Journal of Clinical Microbiology, vol. 43, No. 2, Feb. 2005, pp. 778-785.
HiMedia Laboratories Pvt. Ltd., "TNM-FH Insect Medium With Lactalbumin hydrolysate, Yeast extract, L-Glutamine and Sodium bicarbonate 1X Liquid Insect Cell Culture Medium." Revision: Jan. 2013, pp. 1-2.
Warren et al., "Effect of Osmolality of the Cellular Microenvironment." Encyclopedia of Industrial Biotechnology: Bioprocess, Bioseparation, and Cell Technology: Animal Cells, Hybridomas, Human Antibody Production, John Wiley & Sons, Inc., 2010, pp. 1-16.
Li et al., "Essential Elements of the Capsid Protein for Self-Assembly into Empty Virus-Like Particles of Hepatitis E Virus". Journal of Virology, vol. 79, No. 20, Oct. 2005, pp. 12999-13006.
Moraes et al., "Drosophila melanogaster S2 cells for expression of heterologous genes: From gene cloning to bioprocess development." Biotechnology Advances, vol. 30, 2012, pp. 613-638.
Olejnik et al. "Effect of hyperosmolarity on recombinant protein productivity in baculovirus expression system." Journal of Biotechnology, vol. 102, 2003, pp. 291-300.
Sico et al., "Enhanced Kinetic Extraction of Parvovirus B19 Structural Proteins." Biotechnology and Bioengineering, vol. 80, No. 3, Nov. 5, 2002, pp. 250-256.
Pejawar-Gaddy et al., "Generation of a Tumor Vaccine Candidate Based on Conjugation of a MUC1 Peptide to Jolyionic Papillomavirus Virus-Like Particles (VLPs)." Cancer Immunogy, Immunotherapy, vol. 59, No. 11, Nov. 2010, pp. 1648-1696.
Yamaji et al., "Efficient production of Japanese encephalitis virus-like particles by recombinant lepidopteran insect cells." Applied Microbiology and Biotechnology, vol. 97, 2013, pp. 1071-1079.
Ng et al., "Extracellular self-assembly of virus-like particles from secreted recombinant polyoma virus major coat protein." Protein Engineering, Design & Selection, vol. 20, No. 12, 2007, pp. 591-598.
Viscidi et al., "Age-Specific Seroprevalence of Merkel Cell Polyomavirus, BK Virus, and JC Virus." Clinical and Vaccine Immunology, vol. 18, No. 10, Oct. 2011, pp. 1737-1743.
Sigma-Aldrich®, "Product Information for TNM-FH Insert Media", 2014, 1 page.
Diamantstein et al., "Stimulation of humoral antibody formation by polyanions: I. The effect of polyacrylic acid on the primary immune response in mice immunized with sheep red blood cells." European Journal of Immunology, vol. 1, 1971, pp. 335-340.
Desrosiers et al., "Preliminary results with Ingelvac® CircoFLEX™ to protect multiple ages of Quebec Pigs against PCVAD." American Association of Swine Veterinarians, 2007, pp. 143-145.

(56) References Cited

OTHER PUBLICATIONS

Dehaven, W. Ron, "Veterinary Services Memorandum No. 800. 202." CVB General Licensing Considerations: Efficacy Stupies, Jun. 14, 2002, pp. 1-8.
Krakowka et al., "Activation of the Immune System is the Pivotal Event in the Production of Wasting Disease in Pigs Infected with Porcine Circovirus-2 (PCV-2)" Veterinary Pathology, vol. 38, 2001, pp. 31-42.
Urniza et al., "Duration of Immunity Study in Pigs Vaccinated with an Inactivated/Adjuvanted Vaccine 'Chimeric Porcine Circovirus Type 1/Type 2' in Front of a Challenge with PCV2 European Strain." Proccedings of the 19th IPVS congress, Copenhagen, Denmark, vol. 2, Abstract No. P.07-09, 2006, p. 108.
Clark, Ted, "Pathology of the Postweaning Multisystemic Wastings Syndrome in Pigs." Proceedings of the Western Canadian Association of Swine Practitioners, 1996 Annual Meeting, Oct. 1996, pp. 22-25.
Harding, John C. "Post Weaning Multisystemic Wasting Syndrome (PMWS): Preliminary Epidemiology and Clinical Findings." Proceedings of the Western Canadian Association of Swine Practitioners, 1996 Annual Meeting, Oct. 1996, p. 21.
Harding et al., "Postweaning multisystemic wasting syndrome: Epidemiology and clincial presentation." Swine Health and Production, vol. 6, No. 6, 1998, pp. 249-254.
Onuki et al., "Detection of Porcine Circovirus from Lesions of a Pig with Wasting Disease in Japan." The Journal of Veterinary Medical Science, vol. 61, No. 10, Oct. 1999, pp. 1119-1123.
Larochelle et al., "PCR Detection and Evidence of Shedding of Porcine Circovirus Type 2 in Boar Semen." Journal of Clinical Microbiology, vol. 38, No. 12, Dec. 2000, pp. 4629-4632.
Magar et al., "Experimental Transmission of Porcine Circovirus Type 2 (PCV2) in Weaned Pigs: a Sequential Study." Journal of Comparative Pathology, vol. 123, 2000, pp. 258-269.
Krakowka et al., "Viral Wasting Sydrome of Swine: Experimental Reproduction of Postweaning Multisystemic Wasting Syndrome in Gnotobiotic Swine by Coinfection with Porcine Circovirus 2 and Porcine Parvovirus." Veterinary Jathology, vol. 37, 2000, pp. 254-263.
Brockmeier et al., "Porcine Respiratory Disease Complex." Polymicrobial Diseases, Washington (DC), ASM Press; 2002, Chapter 13, pp. 1-25. [Accessed at https://www.ncbi.nlm.nih.gov/books/NBK2481/].
Rossow et al., "Experimental porcine reproductive and respiratory syndrome virus infection in one-, four-, and 10-week-old pigs." Journal of Veterinary Diagnositc Investigations, vol. 6, 1994, pp. 3-12.
Bretey et al., "Performance benefits resulting from vaccination with Ingelvac CircoFLEX and/or Ingelvac PRRS MLV." Leman Swine Conference 2009, 1 page.
Vidor, E. "The Nature and Consequences of Intra- and Inter-Vaccine Interference." Journal of Comparative Pathology, vol. 137, 2007, pp. S62-S66.
Stokka et al., "Modified-Live Vs. Killed Vaccines—Which is Better?" BeefMagazine.com, Oct. 2000, pp. 1-6. [Accessed at: http://beefmagazine.com/mag/beef_modifiedlive_vs_killed on Nov. 4, 2014].
"Killed vs. Modified Live Vaccines." DVMvac.org, 2006, pp. 1-3. [Accessed at http://dvmvac.org/killvmodified.asp on Oct. 10, 2017].
Goldenthal et al., "Overview-Combination Vaccines and Simultaneous Administration: Past, Present, and Future." Annals of the New York Academy of Sciences, vol. 754, 1995, pp. xi-xiv.
Insel et al., "Potential Alterations in Immunogenicity by Combining or Simultaneously Administering Vaccine Components." Annals of the New York Academy of Sciences, vol. 754, 1995, pp. 35-47.

Merial Animal Health Ltd., "Progressis." 2011, pp. 1-2. [Accessed at http://www.noahcompendium.co.uk/Mierial_Animal_Health_ltd/documents/53834.html on Apr. 12, 2011].
Intervet Schering-Plough Animal Health, "Porcilis PRRS Data Sheet." 2011, pp. 1-3. [Accessed at http://www.intervet.co.uk/Products_Public/Porcilis_PRRS/Product_Datasheet.aspx on Apr. 12, 2011.].
Siegrist, Claire-Anne, "Mechanisms by which maternal antibodies influence infant vaccine responses: review of hypotheses and definition of main determinants." Vaccine, vol. 21, 2003, pp. 3406-3412.
Charreyre et al., "Vaccination Concepts in Controlling PCV2-Associated Diseases." Merial, 18th IPVS, Hamburg (Germany), Jun. 2004, pp. 95-107.
Siegrist et al., "Influence of maternal antibodies on vaccine responses: inhibition of antibody but not T cell responses allows successful early prime-boost strategies in mice." European Journal of Immunology, vol. 28, 1998, pp. 4138-4148.
Gerber et al., "Fetal infections and antibody profiles in pigs naturally infected with porcine circovirus type 2 (PCV2)." The Canadian Journal of Veterinary Research, vol. 76, 2012, pp. 38-44.
Polo et al., "Half-life of porcine antibodies absorbed from a colostrum supplement containing porcine mmunoglobulins." Journal of Animal Science, vol. 90, 2012, pp. 308-310.
Remington et al., "Active Immunizing Agents." Remington: The Science and Practice of Pharmacy, Twentieth Edition, 2000, p. 1569.
Eisele, Simon, "Determination of the efficacy of an inactivated one-shot vaccine in piglets during the first or third week of life with Porcilis® PCV." Inaugural Dissertation for the Obstetrics of Veterinary Medicine at the Faculty of Veterinary Medicine, Ludwig-Maximilians-Universitat Munchen, Jul. 17, 2009. (Summary in English beginning at p. 39), pp. 1-88.
Csank et al., "Dynamics of antibody response and viraemia following natural infection of porcine circovirus 2 (PCV-2) in a conentional pig herd." Acta Pathologica, Microbiologica and Immunologica Scandinavica, vol. 121, 2012, pp. 1207-1213.
O'Neill, Kevin Charles, "Efficacy and impact of current commercial porcine circovirus type 2 (PCV2) vaccines in dams and growing pigs." Graduate Theses and Dissertations, Graduate College, Iowa State University, Paper 12837, 2012, pp. 1-130.
Bunn, Thomas O., "Vaccine Adjuvants and Carriers." Vaccines for Veterinary Applications, Oxford, Boston, Butterworth-Heinemann, 1993, pp. 295-302.
Hulst et al., "Glycoprotein E1 of Hog Cholera Virus Expressed in Insect Cells Protects Swine from Hog Cholera." Journal of Virology, vol. 67, No. 9, Sep. 1993, pp. 5435-5442.
Halbur et al., "Update on Porcine Circovirus Type 2 (PCV2)-Associated Diseases." Veterinary Diagnostic and Production Animal Medicine, Iowa State University, Ames, IA, 12th Annual Swine Disease Conference for Swine Practitioners, Nov. 2004, pp. 12-23.
Harayama et al., "Maternal porcine circovirus type 2-memory T cells transfers to piglets through colostrums ingestion." Proceedings of the 5th Asian Pig Veterinary Society Congress Mar. 7-9, 2011, Pattaya, Thailand, pp. 82.
Reynaud et al., "Comparison of Clinical, Lesional and Virological Signs in Pigs With and Without Experimental PMWS" Proceedings of the 17th International Pig Veterinary Society Congress, Ames, Iowa, USA, Jun. 2002, vol. 1, p. 172.
Shi et al., "Protein N-Glycosylation in the Baculovirus-Insect Cell System." Current Drug Targets, vol. 8, No. 0, Oct. 2007, pp. 1116-1125.
Sequence Alignment of Seq ID No. 1 with UniProt database access No. A7YF28_PCV2 by Li et al 2007.
Sequence Alignment of Seq ID No. 1 with UniProt database access No. F8V1XO_PCV2 by Turcitu et al 2011.

* cited by examiner

FIG. 2(a)

```
┌─────────────────────────┐
│ 1. SF+ Master Cell Stock│
└───────────┬─────────────┘
            ▼
┌─────────────────────────┐
│ 2. SF+ Working Cell Stock│
└───────────┬─────────────┘
            ▼
┌──────────────────┐   ┌─────────────────────────┐
│ Ex-Cell 420 medium│──▶│ 3. Subculture Psg 20 -58│──┐
└──────────────────┘   └───────────┬─────────────┘  │
                                   ▼                 ▼
                                                ┌──────────────┐
┌──────────────────┐   ┌─────────────────────────┐│ Microscopic  │
│ Ex-Cell 420 medium│──▶│ 4. Bioreactor SF+ Culture│ Examination │
└──────────────────┘   └───────────┬─────────────┘└──────────────┘
┌──────────────────┐               │
│ Sterile Filtration│──────────────┤           ┌──────────────────────────┐
└──────────────────┘               │           │ Microscopic Examination  │
                                   │───────────│ Cell count, Cell viability│
┌──────────────────┐               ▼           └──────────────────────────┘
│ Ex-Cell 420 medium│──▶┌─────────────────────────┐
└──────────────────┘   │ 5. PCV-2 ORF2           │
                       │    Baculovirus Culture  │
                       └───────────┬─────────────┘
┌──────────────────┐               │           ┌──────────────────────────┐
│ Inoculation with WSV│────────────┤           │ Microscopic Examination  │
│ MSV+1 to max MSV+4  │            │───────────│ Cell count, Cell viability│
└──────────────────┘               ▼           └──────────────────────────┘
                       ┌─────────────────────────┐
                       │ 6. Harvest              │
                       └───────────┬─────────────┘
                                   ▼
                       ┌─────────────────────────┐
                       │ 7. Filtration           │
                       └─────────────────────────┘
```

USE OF A PCV2 IMMUNOGENIC COMPOSITION FOR LESSENING CLINICAL SYMPTOMS IN PIGS

SEQUENCE LISTING

This application contains a sequence listing in paper format and in computer readable format, the teachings and content of which are hereby incorporated by reference.

BACKGROUND OF THE INVENTION

Field of the Invention

The present invention relates to the use of an immunogenic composition comprising a porcine circovirus type 2 (PCV2) antigen for treatment of several clinical manifestations (diseases). Preferably, those clinical manifestations are associated with a PCV2 infection. More particularly, the present invention is concerned with an immunological composition effective for providing an immune response that reduces, or lessens the severity, of the clinical symptoms associated with PCV2 infection. Preferably, the immunological composition comprises a recombinantly produced antigen of PCV2. More preferably, the PCV2 antigen is a recombinantly produced protein encoded by one of the open reading frames (ORFs) in the PCV2 genome. Still more preferably, the antigen is PCV2 ORF2 protein. Most particularly, the present invention is concerned with an immunological composition effective for treatment of clinical symptoms associated with PCV2 infections in swine receiving the immunological composition, and wherein the composition comprises the protein expressed by ORF2 of PCV2. Another aspect of the present invention is the use of any of the compositions provided herewith as a medicament, preferably as a veterinary medicament, even more preferably as a vaccine. Moreover, the present invention also relates to the use of any of the compositions described herein, for the preparation of a medicament for reducing or lessening the severity of clinical symptoms associated with PCV2 infection. Preferably, the medicament is for the prevention of a PCV2 infection, even more preferably in swine. A further aspect of the present invention relates to a process for the production of a medicament, comprising an immunogenic composition of PCV2 for the treatment of several clinical manifestations.

Description of the Prior Art

Porcine circovirus type 2 (PCV2) is a small (17-22 nm in diameter), icosahedral, non-enveloped DNA virus, which contains a single-stranded circular genome. PCV2 shares approximately 80% sequence identity with porcine circovirus type 1 (PCV1). However, in contrast with PCV1, which is generally non-virulent, swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In some affected swine, a combination of all symptoms will be apparent while other affected swine will only have one or two of these symptoms. During necropsy, microscopic and macroscopic lesions also appear on multiple tissues and organs, with lymphoid organs being the most common site for lesions. A strong correlation has been observed between the amount of PCV2 nucleic acid or antigen and the severity of microscopic lymphoid lesions. Mortality rates for swine infected with PCV2 can approach 80%. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia. However, research thus far has not confirmed whether any of these clinical symptoms are in fact, the direct result of a PCV2 infection. Moreover, it is not yet known whether any of these clinical symptoms can be effectively reduced or cured by an active agent directed against PCV2.

Current approaches to treat PCV2 infections include DNA-based vaccines, such as those described in U.S. Pat. No. 6,703,023. However, such vaccines have been ineffective at conferring protective immunity against PCV2 infection or reducing, lessening the severity of, or curing any clinical symptoms associated therewith. Moreover, vaccines described in the prior art were focused solely on the prevention of PCV2 infections in swine, but did not consider any further medical use.

Accordingly, what is needed in the art is an immunogenic composition for the treatment of several clinical manifestations. Further, what is needed in the art is an immunological composition which confers protective immunity against PCV2 infection but which can also be used to treat existing clinical symptoms associated with PCV2 infection.

DISCLOSURE OF THE INVENTION

The present invention overcomes the problems inherent in the prior art and provides a distinct advance in the state of the art. The present invention provides a medicinal use(s) of immunogenic composition(s) comprising PCV2 antigen.

In general no adverse events or injection site reactions were noted for any of the PCV2 antigen immunogenic compositions as used herein. Thus, the immunogenic compositions used herein appear to be safe when administered to young pigs, preferably to pigs not older than 15 weeks of age, more preferably not older than 6 weeks of age, even more preferably not older than 3 weeks, most preferably not older than 2 weeks. Alternatively, it is preferred that the administration of the immunogenic compositions of the present invention occur within at least 2 and preferably within at least 3 weeks of exposure to virulent PCV. According to a further embodiment, the immunogenic compositions used herein for any medicinal use described herein, is administered to pigs of 3 weeks of age or older, preferably of 2 weeks of age or older, most preferably but not older than 15 weeks of age.

Unexpectedly, it was found that the therapeutic use of the immunogenic compositions described below, is effective for lessening the severity of various clinical symptoms in swine. In particular, it was discovered that the therapeutic use of the immunogenic compositions of the present invention, and specifically compositions comprising PCV2 ORF2 antigen, is effective for reducing or lessening lymphadenopathy, lymphoid depletion and/or multinucleated/giant histiocytes in swine infected with PCV2. Moreover, the therapeutic use of an antigenic composition, as provided herewith, and that comprises PCV2 antigen, preferably ORF2 antigen, reduces the overall circovirus load and its immunosuppressive impact, thereby resulting in a higher level of general disease resistance and a reduced incidence of PCV-2 associated diseases and symptoms.

Thus one aspect of the present invention relates to the use of an immunogenic composition comprising PCV2 antigen, preferably recombinant PCV2 antigen, and more preferably PCV2 ORF2 protein as provided herewith, for the preparation of a medicament for the prevention, lessening and/or reduction of lymphadenopathy, lymphoid depletion and/or multinucleated/giant histiocytes in swine. Preferably, said medicament is effective for the prevention, lessening and/or reduction of lymphadenopathy, lymphoid depletion and/or multinucleated/giant histiocytes associated with PCV2 infections in swine. Still more preferably, said medicament is effective for the prevention, lessening and/or reduction of lymphadenopathy, lymphoid depletion and/or multinucleated/giant histiocytes associated with PCV2 infections in pigs, when administered to pigs not older than 15 weeks of age, more preferably not older than 6 weeks of age, even more preferably not older than 3 weeks, and most preferably not older than 2 weeks. Alternatively, it is preferred that the administration of the immunogenic compositions of the present invention occur within at least 2 and preferably within at least 3 weeks of exposure to virulent PCV.

Another aspect of the present invention relates to a method for the treatment of lymphadenopathy, lymphoid depletion and/or multinucleated/giant histiocytes in swine, comprising the administration of an immunogenic composition as provided herewith, to a pig, said immunogenic composition comprising a PCV2 antigen, preferably a recombinant PCV2 antigen, and more preferably PCV2 ORF2 protein. In yet another aspect, the present invention provides a method for the treatment of lymphadenopathy, lymphoid depletion and/or multinucleated/giant histiocytes associated with a PCV2 infection in swine, comprising the administration of an immunogenic composition as provided herewith, to a pig, said immunogenic composition comprising a PCV2 antigen, preferably a recombinant PCV2 antigen and more preferably PCV2 ORF2 protein. Preferably, said treatment results in the lessening, reduction, prevention, and/or cure of the lymphadenopathy, lymphoid depletion and/or multinucleated/giant histiocytes in swine receiving said immunogenic composition. According to a further aspect, said methods for treatment further comprise the administration of said immunogenic composition to pigs not older than 15 weeks of age, more preferably not older than 6 weeks of age, even more preferably not older than 3 weeks, and most preferably not older than 2 weeks. Alternatively, it is preferred that the administration of the immunogenic compositions of the present invention occur within at least 2 and preferably within at least 3 weeks of exposure to virulent PCV.

It was further discovered that the therapeutic use of an immunogenic composition comprising PCV2 antigen, preferably a recominant PCV2 antigen, and most preferably PCV2 ORF2 protein, as provided herewith, can reduce or lessen lymphadenopathy in combination with one or a multiple of the following symptoms in affected swine: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc.

Thus one aspect of the present invention relates to the use of an immunogenic composition comprising PCV2 antigen, preferably a recombinant PCV2 antigen and more preferably, PCV2 ORF2 protein as provided herewith, for the preparation of a medicament for the prevention, lessening and/or reduction of lymphadenopathy in combination with one or a multiple of the following symptoms in pigs: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc., in pigs. Preferably, said medicament is effective for the prevention, lessening and/or reduction of lymphadenopathy in combination with one or a multiple of the following symptoms associated with PCV2 infection in pigs: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc. According to a further aspect, said medicament is effective for the prevention, lessening and/or reduction of lymphadenopathy in combination with one or a multiple of the following symptoms in pigs: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc., in pigs, when administered to pigs not older than 15 weeks of age, more preferably not older than 6 weeks of age, even more preferably not older than 3 weeks, and most preferably not older than 2 weeks. Alternatively, it is preferred that the administration of the immunogenic compositions of the present invention occur within at least 2 and preferably within at least 3 weeks of exposure to virulent PCV.

Moreover, the present invention also relates to a method for the treatment of lymphadenopathy in combination with one or a multiple of the following symptoms in pigs: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc., said method comprising the administration of an immunogenic composition comprising PCV2 antigen, preferably a recombinant PCV2 antigen, and more preferably PCV2 ORF2 protein as provided herewith. Preferably, the present invention also relates to a method for the treatment of lymphadenopathy in combination with one or a multiple of the following symptoms associated with PCV2 infection in pigs: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc., said method comprising the administration of an immunogenic composition comprising PCV2 antigen, preferably recombinant PCV2 antigen and more preferably PCV2 ORF2 protein, as provided herewith, to a pig. Preferably, said treatment results in the lessening or reduction of the lymphadenopathy, and one or multiple of the following symptoms associated with PCV2 infection in pigs: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc. According to a further aspect, said methods for treatment further comprise administration of the immunogenic composition comprising PCV2 antigen, preferably recombinant PCV2 antigen and more preferably PCV2 ORF2 protein, as provided herein, to pigs not older than 15 weeks of age, more preferably not older than 6 weeks of age, even more preferably not older than 3 weeks, and most preferably not older than 2 weeks. Alternatively, it is preferred that the administration of the immunogenic compositions of the present invention occur within at least 2 and preferably within at least 3 weeks of exposure to virulent PCV.

It was also unexpectedly found that the therapeutic use of an immunogenic composition comprising PCV antigen, preferably recombinant PCV2 antigen and more preferably PCV2 ORF2 protein as provided herewith, can also reduce or lessen Pia like lesions, normally known to be associated with *Lawsonia intracellularis* infections (Ileitis).

Thus one aspect of the present invention relates to the use of an immunogenic composition comprising PCV2 antigen, preferably recombinant PCV2 antigen and more preferably PCV2 ORF2 protein as provided herewith, for the preparation of a medicament for the prevention, lessening the severity of and/or reduction of Pia like lesions, normally known to be associated with *Lawsonia intracellularis* infections in swine. According to a further aspect, said medicament is effective for the prevention, lessening of the severity of and/or reduction of Pia like lesions, normally known to be associated with *Lawsonia intracellularis* infections, when administered to pigs not older than 15 weeks of age, more preferably not older than 6 weeks of age, even more preferably not older than 3 weeks, and most preferably not older than 2 weeks. Alternatively, it is preferred that the administration of the immunogenic compositions of the present invention occur within at least 2 and preferably within at least 3 weeks of exposure to virulent PCV.

Moreover, the present invention also relates to a method for the treatment of Pia like lesions, normally known to be associated with *Lawsonia intracellularis* infections, said method comprising the administration of an immunogenic composition comprising PCV2 antigen, preferably recombinant PCV2 antigen and more preferably PCV2 ORF2 protein as provided herein, to a pig. Preferably, said treatment results in the lessening or reduction of the Pia like lesions, normally known to be associated with *Lawsonia intracellularis* infections. According to a further aspect, the methods for treatment described above further comprise the administration of the immunogenic composition comprising PCV2 antigen, preferably recombinant PCV2 antigen, and more preferably PCV2 ORF2 protein as provided herein, to pigs not older than 15 weeks of age, more preferably not older than 6 weeks of age, even more preferably not older than 3 weeks, and most preferably not older than 2 weeks. Alternatively, it is preferred that the administration of the immunogenic compositions of the present invention occur within at least 2 and preferably within at least 3 weeks of exposure to virulent PCV.

The Immunogenic Composition

The immunogenic composition as used herein is effective for inducing an immune response against PCV2 and preventing, reducing and/or lessening the severity of the clinical symptoms associated with PCV2 infection. The composition generally comprises at least one PCV2 antigen.

Unless defined otherwise, all technical and scientific terms used herein have the same meanings as commonly understood by one of ordinary skill in the art to which this invention belongs. The term "immunogenic composition" as used herein refers to any pharmaceutical composition containing a PCV2 antigen, which composition can be used to prevent or treat a PCV2 infection-associated disease or condition in a subject. A preferred immunogenic composition can induce, stimulate or enhance the immune response against PCV2. The term thus encompasses both subunit immunogenic compositions, as described below, as well as compositions containing whole killed, or attenuated and/or inactivated PCV2.

The term "subunit immunogenic composition" as used herein refers to a composition containing at least one immunogenic polypeptide or antigen, but not all antigens, derived from or homologous to an antigen from PCV2. Such a composition is substantially free of intact PCV2. Thus, a "subunit immunogenic composition" is prepared from at least partially purified or fractionated (preferably substantially purified) immunogenic polypeptides from PCV2, or recombinant analogs thereof. A subunit immunogenic composition can comprise the subunit antigen or antigens of interest substantially free of other antigens or polypeptides from PCV2, or in fractionated from. A preferred immunogenic subunit composition comprises the PCV2 ORF2 protein as described below.

An "immunological or immune response" to a composition or vaccine is the development in the host of a cellular and/or antibody-mediated immune response to the composition or vaccine of interest. Usually, an "immune response" includes but is not limited to one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction in number or severity of, or lack of one or more of the symptoms associated with PCV2 infections as described above.

The terms "immunogenic" protein or polypeptide or "antigen" as used herein refer to an amino acid sequence which elicits an immunological response as described above. An "immunogenic" protein or polypeptide, as used herein, includes the full-length sequence of any PCV2 proteins, analogs thereof, or immunogenic fragments thereof. The term "immunogenic fragment" refers to a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, Jun. 28-Jul. 3, 1998.

In a preferred embodiment of the present invention, an immunogenic composition that induces an immune response and, more preferably, confers protective immunity against the clinical signs of PCV2 infection, is provided. The composition most preferably comprises the polypeptide, or a fragment thereof, expressed by ORF2 of PCV2, as the antigenic component of the composition. PCV2 ORF2 DNA and protein, used herein for the preparation of the compositions and within the processes provided herein is a highly conserved domain within PCV2 isolates and thereby, any PCV2 ORF2 would be effective as the source of the PCV ORF2 DNA and/or polypeptide as used herein. A preferred PCV2 ORF2 protein is that of SEQ ID NO. 11. A preferred PCV ORF2 polypeptide is provided herein as SEQ ID NO. 5, but it is understood by those of skill in the art that this sequence could vary by as much as 6-10% in sequence homology and still retain the antigenic characteristics that render it useful in immunogenic compositions. The antigenic characteristics of an immunological composition can be, for example, estimated by the challenge experiment as provided by Example 4. Moreover, the antigenic characteristic of a modified antigen is still retained, when the modified antigen confers at least 70%, preferably 80%, more preferably 90% of the protective immunity as compared to the PCV2 ORF 2 protein, encoded by the polynucleotide sequence of SEQ ID NO:3 or SEQ ID NO:4. An "immunogenic composition" as used herein, means a PCV2 ORF2 protein which elicits an "immunological response" in the host of a cellular and/or antibody-mediated immune response to PCV2 ORF2 protein. Preferably, this immunogenic composition is capable of eliciting or enhancing an immune response against PCV2 thereby conferring protective immunity against PCV2 infection and a reduction in the incidence of, severity of, or prevention of one or more, and preferably all of the clinical signs associated therewith.

In some forms, immunogenic portions of PCV2 ORF2 protein are used as the antigenic component in the composition. The term "immunogenic portion" as used herein refers to truncated and/or substituted forms, or fragments of PCV2 ORF2 protein and/or polynucleotide, respectively. Preferably, such truncated and/or substituted forms, or fragments will comprise at least 6 contiguous amino acids from the full-length ORF2 polypeptide. More preferably, the truncated or substituted forms, or fragments will have at least 10, more preferably at least 15, and still more preferably at least 19 contiguous amino acids from the full-length ORF2 polypeptide. Two preferred sequences in this respect are provided herein as SEQ ID NOs. 9 and 10. It is further understood that such sequences may be a part of larger fragments or truncated forms.

A further preferred PCV2 ORF2 polypeptide provided herein is encoded by the nucleotide sequences of SEQ ID NO: 3 or SEQ ID NO: 4. However, it is understood by those of skill in the art that this sequence could vary by as much as 6-20% in sequence homology and still retain the antigenic characteristics that render it useful in immunogenic compositions. In some forms, a truncated or substituted form, or fragment of this PVC2 ORF2 polypeptide is used as the antigenic component in the composition. Preferably, such truncated or substituted forms, or fragments will comprise at least 18 contiguous nucleotides from the full-length ORF2 nucleotide sequence, e.g. of SEQ ID NO: 3 or SEQ ID NO: 4. More preferably, the truncated or substituted forms, or fragments, will have at least 30, more preferably at least 45, and still more preferably at least 57 contiguous nucleotides of the full-length ORF2 nucleotide sequence, e.g. SEQ ID NO: 3 or SEQ ID NO: 4.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferably at least 100, even more preferably at least 250, and even more preferably at least 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Thus, the immunogenic composition as used herein also refers to a composition that comprises PCV2 ORF2 protein, wherein said PCV2 ORF2 protein is anyone of those, described above. Preferably, said PCV2 ORF2 protein is
  i) a polypeptide comprising the sequence of SEQ ID NO: 5, SEQ ID NO: 6, SEQ ID NO: 9, SEQ ID NO: 10 or SEQ ID NO: 11;
  ii) any polypeptide that is at least 80% homologous to the polypeptide of i),
  iii) any immunogenic portion of the polypeptides of i) and/or ii)
  iv) the immunogenic portion of comprising at least 10 contiguous amino acids included in the sequences of SEQ ID NO: 5, SEQ ID NO: 6, SEQ ID NO: 9, SEQ ID NO: 10 or SEQ ID NO: 11,
  v) a polypeptide that is encoded by a DNA comprising the sequence of SEQ ID NO: 3 or SEQ ID NO: 4.
  vi) any polypeptide that is encoded by a polynucleotide that is at least 80% homologous to the polynucleotide of v),
  vii) any immunogenic portion of the polypeptides encoded by the polynucleotide of v) and/or vi)
  viii) the immunogenic portion of vii), wherein polynucleotide coding for said immunogenic portion comprises at least 30 contiguous nucleotides included in the sequences of SEQ ID NO: 3, or SEQ ID NO: 4.

Preferably any of those immunogenic portions have the immunogenic characteristics of PCV2 ORF2 protein that is encoded by the sequence of SEQ ID NO: 3 or SEQ ID NO: 4.

According to a further aspect, PCV2 ORF2 protein is provided in the immunological composition at an antigen inclusion level effective for inducing the desired immune response, namely reducing the incidence of, lessening the severity of, or preventing one or more clinical signs resulting from PCV2 infection. Preferably, the PCV2 ORF2 protein inclusion level is at least 0.2 µg antigen/ml of the final immunogenic composition (µg/ml), more preferably from about 0.2 to about 400 µg/ml, still more preferably from about 0.3 to about 200 µg/ml, even more preferably from about 0.35 to about 100 µg/ml, still more preferably from about 0.4 to about 50 µg/ml, still more preferably from about 0.45 to about 30 µg/ml, still more preferably from about 0.6 to about 15 µg/ml, even more preferably from about 0.75 to about 8 µg/ml, even more preferably from about 1.0 to about 6 µg/ml, still more preferably from about 1.3 to about 3.0 µg/ml, even more preferably from about 1.4 to about 2.5 µg/ml, even more preferably from about 1.5 to about 2.0 µg/ml, and most preferably about 1.6 µg/ml.

According to a further aspect, the ORF2 antigen inclusion level is at least 0.2 µg/PCV2 ORF2 protein as described above per dose of the final antigenic composition (µg/dose), more preferably from about 0.2 to about 400 µg/dose, still more preferably from about 0.3 to about 200 µg/dose, even more preferably from about 0.35 to about 100 µg/dose, still more preferably from about 0.4 to about 50 µg/dose, still more preferably from about 0.45 to about 30 µg/dose, still more preferably from about 0.6 to about 15 µg/dose, even more preferably from about 0.75 to about 8 µg/dose, even more preferably from about 1.0 to about 6 µg/dose, still more preferably from about 1.3 to about 3.0 µg/dose, even more preferably from about 1.4 to about 2.5 µg/dose, even more preferably from about 1.5 to about 2.0 µg/dose, and most preferably about 1.6 µg/dose.

The PCV2 ORF2 polypeptide used in the immunogenic composition in accordance with the present invention can be derived in any fashion including isolation and purification of PCV2 ORF2, standard protein synthesis, and recombinant methodology. Preferred methods for obtaining PCV2 ORF2 polypeptide are provided in U.S. patent application Ser. No. 11/034,797, the teachings and content of which are hereby incorporated by reference. Briefly, susceptible cells are infected with a recombinant viral vector containing PCV2 ORF2 DNA coding sequences, PCV2 ORF2 polypeptide is expressed by the recombinant virus, and the expressed PCV2 ORF2 polypeptide is recovered from the supernate by filtration and inactivated by any conventional method, preferably using binary ethylenimine, which is then neutralized to stop the inactivation process.

The immunogenic composition as used herein also refers to a composition that comprises i) any of the PCV2 ORF2 protein described above, preferably in concentrations described above, and ii) at least a portion of the viral vector expressing said PCV2 ORF2 protein, preferably of a recombinant baculovirus. Moreover, the immunogenic composition can comprise i) any of the PCV2 ORF2 proteins described above, preferably in concentrations described above, ii) at least a portion of the viral vector expressing said PCV2 ORF2 protein, preferably of a recombinant baculovirus, and iii) a portion of the cell culture supernate.

The immunogenic composition as used herein also refers to a composition that comprises i) any of the PCV2 ORF2 proteins described above, preferably in concentrations described above, ii) at least a portion of the viral vector expressing said PCV2 ORF2 protein, preferably of a recombinant baculovirus, and iii) a portion of the cell culture; wherein about 90% of the components have a size smaller than 1 μm.

The immunogenic composition as used herein also refers to a composition that comprises i) any of the PCV2 ORF2 proteins described above, preferably in concentrations described above, ii) at least a portion of the viral vector expressing said PCV2 ORF2 protein, iii) a portion of the cell culture, iv) and inactivating agent to inactivate the recombinant viral vector preferably BEI, wherein about 90% of the components i) to have a size smaller than 1 μm. Preferably, BEI is present in concentrations effective to inactivate the baculovirus. Effective concentrations are described above.

The immunogenic composition as used herein also refers to a composition that comprises i) any of the PCV2 ORF2 proteins described above, preferably in concentrations described above, ii) at least a portion of the viral vector expressing said PCV2 ORF2 protein, iii) a portion of the cell culture, iv) an inactivating agent to inactivate the recombinant viral vector preferably BEI, and v) an neutralization agent to stop the inactivation mediated by the inactivating agent, wherein about 90% of the components i) to have a size smaller than 1 μm. Preferably, if the inactivating agent is BEI, said composition comprises sodium thiosulfate in equivalent amounts to BEI.

The polypeptide is incorporated into a composition that can be administered to an animal susceptible to PCV2 infection. In preferred forms, the composition may also include additional components known to those of skill in the art (see also Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In a preferred embodiment, the immunogenic composition comprises PCV2 ORF2 protein as provided herewith, preferably in concentrations described above, which is mixed with an adjuvant, preferably Carbopol, and physiological saline.

Those of skill in the art will understand that the composition used herein may incorporate known injectable, physiologically acceptable sterile solutions. For preparing a ready-to-use solution for parenteral injection or infusion, aqueous isotonic solutions, such as e.g. saline or corresponding plasma protein solutions, are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among them, there may be mentioned Carbopol 974P, 934P and 971P. Most preferred is the use of Carbopol, in particular the use of Carbopol 971P, preferably in amounts of about 500 μg to about 5 mg per dose, even more preferred in an amount of about 750 μg to about 2.5 mg per dose and most preferred in an amount of about 1 mg per dose.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314, or muramyl dipeptide among many others.

Preferably, the adjuvant is added in an amount of about 100 μg to about 10 mg per dose. Even more preferably, the adjuvant is added in an amount of about 100 μg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

Additionally, the composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like. Most preferably, the composition provided herewith, contains PCV2 ORF2 protein recovered from the supernate of in vitro cultured cells, wherein said cells were infected with a recombinant viral vector containing PCV2 ORF2 DNA and expressing PCV2 ORF2 protein, and wherein said cell culture was treated with about 2 to about 8 mM BEI, preferably with about 5 mM BEI to inactivate the viral vector, and an equivalent concentration of a neutralization agent, preferably sodium thiosulfate solution to a final concentration of about 2 to about 8 mM, preferably of about 5 mM.

The present invention also relates to an immunogenic composition that comprises i) any of the PCV2 ORF2 proteins described above, preferably in concentrations described above, ii) at least a portion of the viral vector expressing said PCV2 ORF2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; and vi) a suitable adjuvant, preferably Carbopol 971 in amounts described above; wherein about 90% of the components i) to have a size smaller than 1 µm. According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic composition as used herein also refers to a composition that comprises per one ml i) at least 1.6 µg of PCV2 ORF2 protein described above, ii) at least a portion of baculovirus expressing said PCV2 ORF2 protein iii) a portion of the cell culture, iv) about 2 to 8 mM BEI, v) sodium thiosulfate in equivalent amounts to BEI; and vi) about 1 mg Carbopol 971, and vii) phosphate salt in a physiologically acceptable concentration; wherein about 90% of the components i) to have a size smaller than 1 µm and the pH of said immunogenic composition is adjusted to about 6.5 to 7.5.

The immunogenic compositions can further include one or more other immunomodulatory agents such as, e. g., interleukins, interferons, or other cytokines. The immunogenic compositions can also include Gentamicin and Merthiolate. While the amounts and concentrations of adjuvants and additives useful in the context of the present invention can readily be determined by the skilled artisan, the present invention contemplates compositions comprising from about 50 µg to about 2000 µg of adjuvant and preferably about 250 µg/ml dose of the vaccine composition. Thus, the immunogenic composition as used herein also refers to a composition that comprises from about 1 µg/ml to about 60 µg/ml of antibiotics, and more preferably less than about 30 µg/ml of antibiotics.

The immunogenic composition as used herein also refers to a composition that comprises i) any of the PCV2 ORF2 proteins described above, preferably in concentrations described above, ii) at least a portion of the viral vector expressing said PCV2 ORF2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; vi) a suitable adjuvant, preferably Carbopol 971 in amounts described above; vii) a pharmaceutical acceptable concentration of a saline buffer, preferably of a phosphate salt, and viii) an anti-microbiological active agent; wherein about 90% of the components i) to have a size smaller than 1 µm.

It has been surprisingly found, that the immunogenic composition comprising the PCV2 ORF2 protein was highly stable over a period of 24 months. It has also been found the immunogenic compositions are very effective in reducing the clinical symptoms associated with PCV2 infections. It was also discovered, that the immunogenic compositions comprising the recombinant baculovirus expressed PCV2 ORF2 protein as described above, are surprisingly more effective than an immunogenic composition comprising the whole PCV2 virus in an inactivated form, or isolated viral PCV2 ORF2 antigen. In particular, it has been surprisingly found, that the recombinant baculovirus expressed PCV2 ORF2 protein is effective in very low concentrations, which means in concentrations up to 0.25 µg/dose. This unexpected high immunogenic potential of the PCV2 ORF2 protein is increased by Carbopol. Examples 1 to 3 disclose in detail the production of PCV2 ORF2 comprising immunogenic compositions.

The immunogenic composition as used herein also refers to Ingelvac® CircoFLEX™ (Boehringer Ingelheim Vetmedica, Inc., St Joseph, Mo., USA), CircoVac® (Merial SAS, Lyon, France), CircoVent (Intervet Inc., Millsboro, Del., USA), or Suvaxyn PCV-2 One Dose® (Fort Dodge Animal Health, Kansas City, Kans., USA).

Administration of the Immunogenic Composition

The composition according to the invention may be applied intradermally, intratracheally, or intravaginally. The composition preferably may be applied intramuscularly or intranasally, most preferably intramuscularlly. In an animal body, it can prove advantageous to apply the pharmaceutical compositions as described above via an intravenous or by direct injection into target tissues. For systemic application, the intravenous, intravascular, intramuscular, intranasal, intraarterial, intraperitoneal, oral, or intrathecal routes are preferred. A more local application can be effected subcutaneously, intradermally, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, the compositions according to the invention may be administered once or several times, also intermittently, for instance on a daily basis for several days, weeks or months and in different dosages.

Preferably, at least one dose of the immunogenic compositions as described above is intramuscularly administered to the subject in need thereof. According to a further aspect, the PCV-2 antigen or the immunogenic composition comprising any such PCV-2 antigen as described above is formulated and administered in one (1) mL per dose. Thus, according to a further aspect, the present invention also relates to a 1 ml immunogenic composition, comprising PCV-2 antigen as described herein, for reducing or lessening lymphadenopathy, lymphoid depletion and/or multinucleated/giant histiocytes in pigs infected with PCV2.

According to a further aspect, according to a further aspect, the present invention also relates to a 1 ml immunogenic composition, comprising PCV-2 antigen as described herein, for reducing or lessening lymphadenopathy in combination with one or a multiple of the following symptoms in pigs: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies.

According to a further aspect, at least one further administration of at least one dose of the immunogenic composition as described above is given to a subject in need thereof, wherein the second or any further administration is given at least 14 days beyond the initial or any former administrations. Preferably, the immunogenic composition is administered with an immune stimulant. Preferably, said immune stimulant is given at least twice. Preferably, at least 3 days, more preferably at least 5 days, even more preferably at least 7 days are in between the first and the second or any further administration of the immune stimulant. Preferably, the immune stimulant is given at least 10 days, preferably 15 days, even more preferably 20, even more preferably at least 22 days beyond the initial administration of the immunogenic composition provided herein. A preferred immune stimulant is, for example, keyhole limpet hemocyanin (KLH), preferably emulsified with incomplete Freund's adjuvant (KLH/ICFA). However, it is herewith understood, that any other immune stimulant known to a person skilled in the art can also be used. The term "immune stimulant" as used herein, means any agent or composition that can trigger the immune response, preferably without initiating or increasing a specific immune response, for example the immune response against a specific pathogen. It is further instructed to administer the immune stimulant in a suitable dose.

Moreover, it has also been surprisingly found that the immunogenic potential of the immunogenic compositions used herein, preferably those that comprise recombinant baculovirus expressed PCV2 ORF2 protein, even more preferably in combination with Carbopol, can be further confirmed by the administration of the IngelVac PRRS MLV vaccine (see Example 5). PCV2 clinical signs and disease manifestations are greatly magnified when PRRS infection is present. However, the immunogenic compositions and vaccination strategies as provided herewith lessened this effect greatly, and more than expected. In other words, an unexpected synergistic effect was observed when animals, preferably piglets were treated with any of the PCV2 ORF2 immunogenic compositions, as provided herewith, and the Ingelvac PRRS MLV vaccine (Boehringer Ingelheim).

BRIEF DESCRIPTION OF THE DRAWINGS

FIGS. 2a and 2b are each schematic flow diagrams of how to produce one of the compositions used in accordance with the present invention.

DETAILED DESCRIPTION OF THE PREFERRED EMBODIMENTS

The following examples set forth preferred materials and procedures in accordance with the present invention. Although any methods and materials similar or equivalent to those described herein can be used in the practice or testing of the present invention, the preferred methods, devices, and materials are now described. It is to be understood, however, that these examples are provided by way of illustration only, and nothing therein should be deemed a limitation upon the overall scope of the invention.

Example 1

This example compares the relative yields of ORF2 using methods of the present invention with methods that are known in the prior art. Four 1000 mL spinner flasks were each seeded with approximately $1.0 \times 10^6$ Sf+ cells/ml in 300 mL of insect serum free media, Excell 420 (JRH Biosciences, Inc., Lenexa, Kans.). The master cell culture is identified as SF+(*Spodoptera frugiperda*) Master Cell Stock, passage 19, Lot#N112-095W. The cells used to generate the SF+ Master Cell Stock were obtained from Protein Sciences Corporation, Inc., Meriden, Conn. The SF+ cell line for this example was confined between passages 19 and 59. Other passages will work for purposes of the present invention, but in order to scale the process up for large scale production, at least 19 passages will probably be necessary and passages beyond 59 may have an effect on expression, although this was not investigated. In more detail, the initial SF+ cell cultures from liquid nitrogen storage were grown in Excell 420 media in suspension in sterile spinner flasks with constant agitation. The cultures were grown in 100 mL to 250 mL spinner flasks with 25 to 150 mL of Excell 420 serum-free media. When the cells had multiplied to a cell density of $1.0$-$8.0 \times 10^6$ cells/mL, they were split to new vessels with a planting density of $0.5$-$1.5 \times 10^6$ cells/mL. Subsequent expansion cultures were grown in spinner flasks up to 36 liters in size or in stainless steel bioreactors of up to 300 liters for a period of 2-7 days at 25-29° C.

Figure 1:
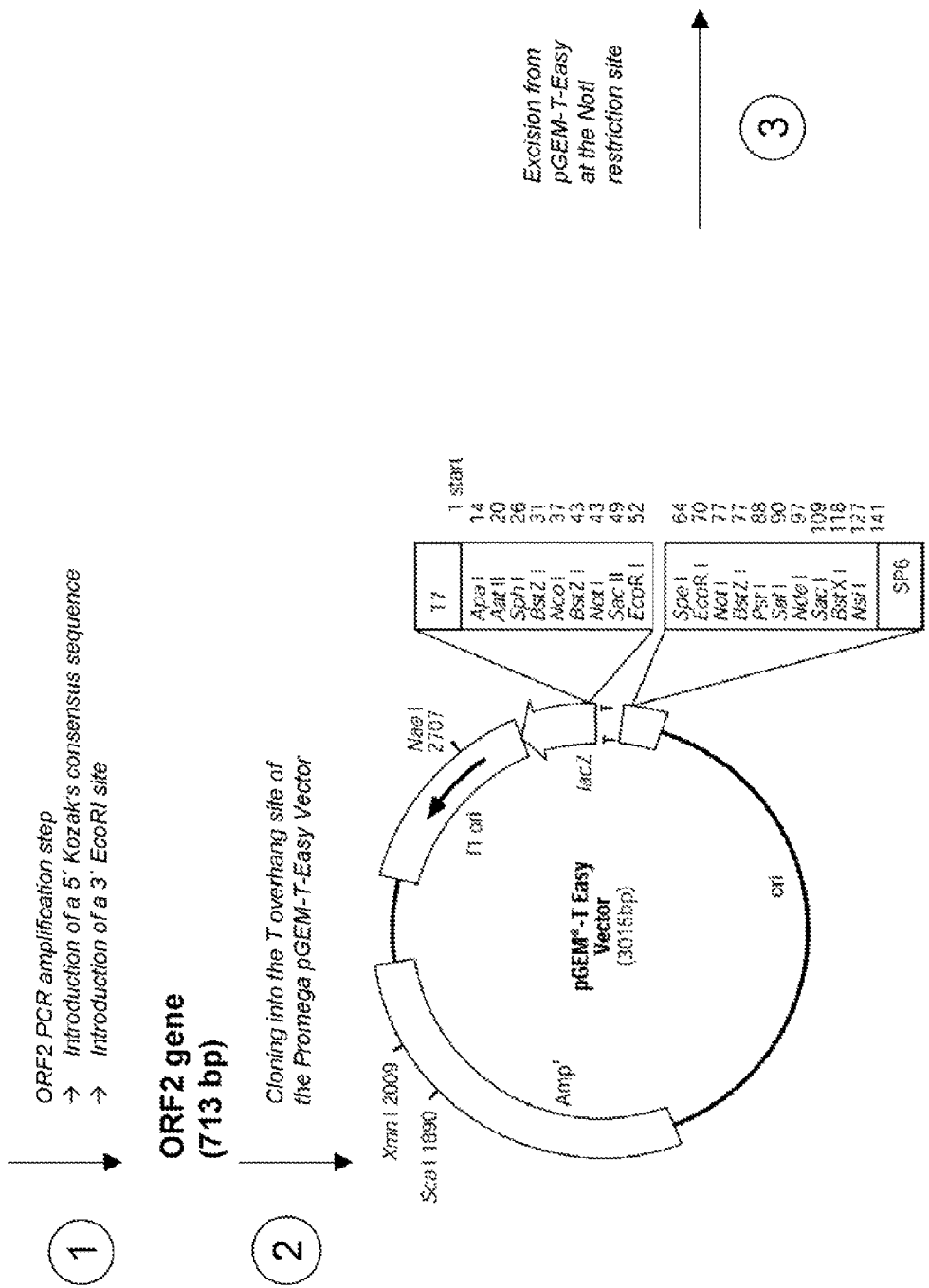
FIG. 1 is a schematic flow diagram of a preferred construction of PCV2 ORF2 recombinant baculovirus.
Figure 1:
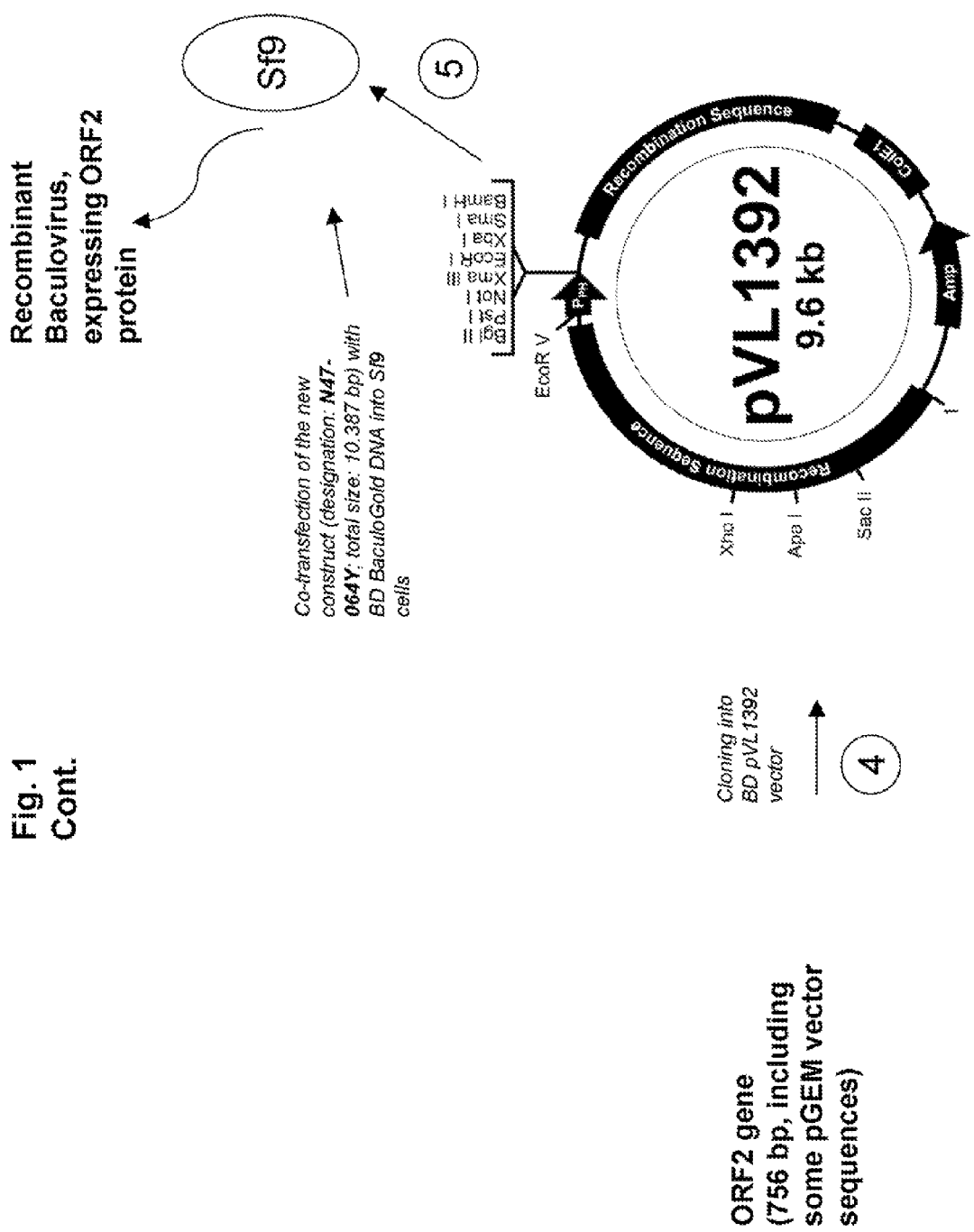
Figure 2B:
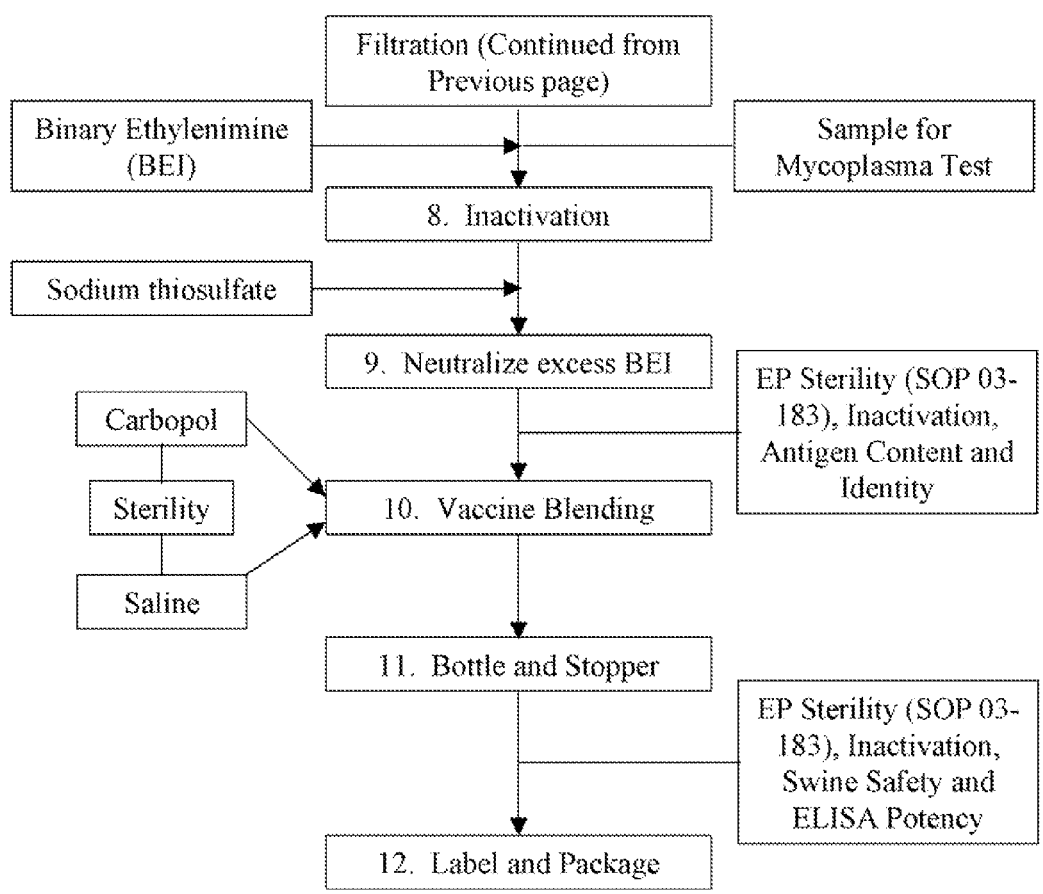

After seeding, the flasks were incubated at 27° C. for four hours. Subsequently, each flask was seeded with a recombinant baculovirus containing the PCV2 ORF2 gene (SEQ ID NO: 4). The recombinant baculovirus containing the PCV2 ORF2 gene was generated as follows: the PCV2 ORF2 gene from a North American strain of PCV2 was PCR amplified to contain a 5' Kozak's sequence (SEQ ID NO: 1) and a 3' EcoR1 site (SEQ ID NO: 2), and cloned into the pGEM-T-Easy vector (Promega, Madison, Wis.). Then, it was subsequently excised and subcloned into the transfer vector pVL1392 (BD Biosciences Pharmingen, San Diego, Calif.). The subcloned portion is represented herein as SEQ ID NO: 7. The pVL1392 plasmid containing the PCV2 ORF2 gene was designated N47-064Y and then co-transfected with BaculoGold® (BD Biosciences Pharmingen) baculovirus DNA into Sf+ insect cells (Protein Sciences, Meriden, Conn.) to generate the recombinant baculovirus containing the PCV2 ORF2 gene. The new construct is provided herein as SEQ ID NO: 8. The recombinant baculovirus containing the PCV2 ORF2 gene was plaque-purified and Master Seed Virus (MSV) was propagated on the SF+ cell line, aliquotted, and stored at −70° C. The MSV was positively identified as PCV2 ORF2 baculovirus by PCR-RFLP using baculovirus specific primers. Insect cells infected with PCV2 ORF2 baculovirus to generate MSV or Working Seed Virus express PCV2 ORF2 antigen as detected by polyclonal serum or monoclonal antibodies in an indirect fluorescent antibody assay. Additionally, the identity of the PCV2 ORF2 baculovirus was confirmed by N-terminal amino acid sequencing. The PCV2 ORF2 baculovirus MSV was also tested for purity in accordance with 9 C.F.R. 113.27 (c), 113.28, and 113.55. Each recombinant baculovirus seeded into the spinner flasks had varying multiplicities of infection (MOIs). Flask 1 was seeded with 7.52 mL of 0.088 MOI seed; flask 2 was seeded with 3.01 mL of 0.36MOI seed; flask 3 was seeded with 1.5 mL of 0.18MOI seed; and flask 4 was seeded with 0.75 mL of 0.09MOI seed. A schematic flow diagram illustrating the basic steps used to construct a PCV2 ORF2 recombinant baculovirus is provided herein as FIG. 1.

After being seeded with the baculovirus, the flasks were then incubated at 27±2° C. for 7 days and were also agitated at 100 rpm during that time. The flasks used ventilated caps to allow for air flow. Samples from each flask were taken every 24 hours for the next 7 days. After extraction, each sample was centrifuged, and both the pellet and the supernatant were separated and then microfiltered through a 0.45-1.0 μm pore size membrane.

The resulting samples then had the amount of ORF2 present within them quantified via an ELISA assay. The ELISA assay was conducted with capture antibody Swine anti-PCV2 Pab IgG Prot. G purified (diluted 1:250 in PBS) diluted to 1:6000 in 0.05M Carbonate buffer (pH 9.6). 100 μL of the antibody was then placed in the wells of the mictrotiter plate, sealed, and incubated overnight at 37° C. The plate was then washed three times with a wash solution which comprised 0.5 mL of Tween 20 (Sigma, St. Louis, Mo.), 100 mL of 10×D-PBS (Gibco Invitrogen, Carlsbad, Calif.) and 899.5 mL of distilled water. Subsequently, 250 μL of a blocking solution (5 g Carnation Non-fat dry milk (Nestle, Glendale, Calif.) in 10 mL of D-PBS QS to 100 mL with distilled water) was added to each of the wells. The next step was to wash the test plate and then add pre-diluted antigen. The pre-diluted antigen was produced by adding 200 μL of diluent solution (0.5 mL Tween 20 in 999.5 mL D-PBS) to each of the wells on a dilution plate. The sample was then diluted at a 1:240 ratio and a 1:480 ratio, and 100 μL of each of these diluted samples was then added to one of the top wells on the dilution plate (i.e. one top well received 100 μL of the 1:240 dilution and the other received 100 μL of the 1:480 dilution). Serial dilutions were then done for the remainder of the plate by removing 100 μL form each successive well and transferring it to the next well on the plate. Each well was mixed prior to doing the next transfer. The test plate washing included washing the plate three times with the wash buffer. The plate was then sealed and incubated for an hour at 37° C. before being washed three more times with the wash buffer. The detection antibody used was monoclonal antibody to PCV ORF2. It was diluted to 1:300 in diluent solution, and 100 μL of the diluted detection antibody was then added to the wells. The plate was then sealed and incubated for an hour at 37° C. before being washed three times with the wash buffer. Conjugate diluent was then prepared by adding normal rabbit serum (Jackson Immunoresearch, West Grove, Pa.) to the diluent solution to 1% concentration. Conjugate antibody Goat anti-mouse (H+1)-HRP (Jackson Immunoresearch) was diluted in the conjugate diluent to 1:10,000. 100 μL of the diluted conjugate antibody was then added to each of the wells. The plate was then sealed and incubated for 45 minutes at 37° C. before being washed three times with the wash buffer. 100 μL of substrate (TMB Peroxidase Substrate, Kirkgaard and Perry Laboratories (KPL), Gaithersberg, Md.), mixed with an equal volume of Peroxidase Substrate B (KPL) was added to each of the wells. The plate was incubated at room temperature for 15 minutes. 100 μL of 1N HCL solution was then added to all of the wells to stop the reaction. The plate was then run through an ELISA reader. The results of this assay are provided in Table 1 below:

TABLE 1

| Day | Flask | ORF2 in pellet (μg) | ORF2 in supernatant (μg) |
|---|---|---|---|
| 3 | 1 | 47.53 | 12 |
| 3 | 2 | 57.46 | 22 |
| 3 | 3 | 53.44 | 14 |
| 3 | 4 | 58.64 | 12 |
| 4 | 1 | 43.01 | 44 |
| 4 | 2 | 65.61 | 62 |
| 4 | 3 | 70.56 | 32 |
| 4 | 4 | 64.97 | 24 |
| 5 | 1 | 31.74 | 100 |
| 5 | 2 | 34.93 | 142 |
| 5 | 3 | 47.84 | 90 |
| 5 | 4 | 55.14 | 86 |
| 6 | 1 | 14.7 | 158 |
| 6 | 2 | 18.13 | 182 |
| 6 | 3 | 34.78 | 140 |
| 6 | 4 | 36.88 | 146 |
| 7 | 1 | 6.54 | 176 |
| 7 | 2 | 12.09 | 190 |
| 7 | 3 | 15.84 | 158 |
| 7 | 4 | 15.19 | 152 |

These results indicate that when the incubation time is extended, expression of ORF2 into the supernatant of the centrifuged cells and media is greater than expression in the pellet of the centrifuged cells and media. Accordingly, allowing the ORF2 expression to proceed for at least 5 days and recovering it in the supernate rather than allowing expression to proceed for less than 5 days and recovering ORF2 from the cells, provides a great increase in ORF2 yields, and a significant improvement over prior methods.

Example 2

This example provides data as to the efficacy of the invention claimed herein. A 1000 mL spinner flask was seeded with approximately $1.0\times10^6$Sf+ cells/ml in 300 mL of Excell 420 media. The flask was then incubated at 27° C. and agitated at 100 rpm. Subsequently, the flask was seeded with 10 mL of PCV2 ORF2/Bac p+6 (the recombinant baculovirus containing the PCV2 ORF2 gene passaged 6 additional times in the Sf9 insect cells) virus seed with a 0.1 MOI after 24 hours of incubation.

The flask was then incubated at 27° C. for a total of 6 days. After incubation, the flask was then centrifuged and three samples of the resulting supernatant were harvested and inactivated. The supernatant was inactivated by bringing its temperature to 37±2° C. To the first sample, a 0.4M solution of 2-bromoethyleneamine hydrobromide which had been cyclized to 0.2M binary ethlylenimine (BEI) in 0.3N NaOH was added to the supernatant to give a final concentration of BEI of 5 mM. To the second sample, 10 mM BEI was added to the supernatant. To the third sample, no BEI was added to the supernatant. The samples were then stirred continuously for 48 hrs. A 1.0 M sodium thiosulfate solution to give a final minimum concentration of 5 mM was added to neutralize any residual BEI. The quantity of ORF2 in each sample was then quantified using the same ELISA assay procedure as described in Example 1. The results of this may be seen in Table 2 below:

TABLE 2

| Sample | ORF2 in supernatant (μg) |
|---|---|
| 1 | 78.71 |
| 2 | 68.75 |
| 3 | 83.33 |

This example demonstrates that neutralization with BEI does not remove or degrade significant amounts of the recombinant PCV2 ORF2 protein product. This is evidenced by the fact that there is no large loss of ORF2 in the supernatant from the BEI or elevated temperatures. Those of skill in the art will recognize that the recovered ORF2 is a stable protein product.

Example 3

This example demonstrates that the present invention is scalable from small scale production of recombinant PCV2 ORF2 to large scale production of recombinant PCV2 ORF2. $5.0 \times 10^5$ cells/ml of SF+ cells/ml in 7000 mL of ExCell 420 media was planted in a 20000 mL Applikon Bioreactor. The media and cells were then incubated at 27° C. and agitated at 100 RPM for the next 68 hours. At the $68^{th}$ hour, 41.3 mL of PCV2 ORF2 Baculovirus MSV+3 was added to 7000 mL of ExCell 420 medium. The resultant mixture was then added to the bioreactor. For the next seven days, the mixture was incubated at 27° C. and agitated at 100 RPM. Samples from the bioreactor were extracted every 24 hours beginning at day 4, post-infection, and each sample was centrifuged. The supernatant of the samples were preserved and the amount of ORF2 was then quantified using SDS-PAGE densitometry. The results of this can be seen in Table 3 below:

TABLE 3

| Day after infection: | ORF2 in supernatant (µg/mL) |
|---|---|
| 4 | 29.33 |
| 5 | 41.33 |
| 6 | 31.33 |
| 7 | 60.67 |

Example 4

This example tests the efficacy of seven PCV2 candidate vaccines and further defines efficacy parameters following exposure to a virulent strain of PCV2. One hundred and eight (108) cesarean derived colostrum deprived (CDCD) piglets, 9-14 days of age, were randomly divided into 9 groups of equal size. Table 4 sets forth the General Study Design for this Example.

TABLE 4

General Study Design

| Group | No. Of Pigs | Treatment | Day of Treatment | KLH/ICFA on Day 21 and Day 27 | Challenged with Virulent PCV2 on Day 24 | Necropsy on Day 49 |
|---|---|---|---|---|---|---|
| 1 | 12 | PCV2 Vaccine No. 1- (vORF2 16 µg) | 0 | + | + | + |
| 2 | 12 | PCV2 Vaccine No. 2- (vORF2 8 µg) | 0 | + | + | + |
| 3 | 12 | PCV2 Vaccine No. 3- (vORF2 4 µg) | 0 | + | + | + |
| 4 | 12 | PCV2 Vaccine No. 4- (rORF2 16 µg) | 0 | + | + | + |
| 5 | 12 | PCV2 Vaccine No. 5- (rORF2 8 µg) | 0 | + | + | + |
| 6 | 12 | PCV2 Vaccine No. 6- (rORF2 4 µg) | 0 | + | + | + |
| 7 | 12 | PCV2 Vaccine No. 7- (Killed whole cell virus) | 0 | + | + | + |
| 8 | 12 | None-Challenge Controls | N/A | + | + | + |
| 9 | 12 | None-Strict Negative Control Group | N/A | + | − | + | vORF2 = isolated viral ORF2;
rORF2 = recombinant baculovirus expressed ORF2;
killed whole cell virus = PCV2 virus grown in suitable cell culture Seven of the groups (Groups 1-7) received doses of PCV2 ORF2 polypeptide, one of the groups acted as a challenge control and received no PCV2 ORF2, and another group acted as the strict negative control group and also received no PCV2 ORF2. On Day 0, Groups 1 through 7 were treated with assigned vaccines. Piglets in Group 7 were given a booster treatment on Day 14. Piglets were observed for adverse events and injection site reactions following vaccination and on Day 19, piglets were moved to the second study site. At the second study site, Groups 1-8 were group housed in one building while Group 9 was housed in a separate building. All pigs received keyhole limpet hemocyanin (KLH)/incomplete Freund's adjuvant (ICFA) on Days 21 and 27 and on Day 24, Groups 1-8 were challenged with a virulent PCV2.

Pre- and post-challenge, blood samples were collected for PCV2 serology. Post-challenge, body weight data for determination of average daily weight gain (ADWG), and clinical symptoms, as well as nasal swab samples to determine nasal shedding of PCV2, were collected. On Day 49, all surviving pigs were necropsied, lungs were scored for lesions, and selected tissues were preserved in formalin for Immunohistochemistry (IHC) testing at a later date.

Materials and Methods

This was a partially blinded vaccination-challenge feasibility study conducted in CDCD pigs, 9 to 14 days of age on Day 0. To be included in the study, PCV2 IFA titers of sows were ≤1:1000. Additionally, the serologic status of sows were from a known PRRS-negative herd. Twenty-eight (28) sows were tested for PCV2 serological status. Fourteen (14) sows had a PCV2 titer of ≤1000 and were transferred to the first study site. One hundred ten (110) piglets were delivered by cesarean section surgeries and were available for this study on Day −4. On Day −3, 108 CDCD pigs at the first study site were weighed, identified with ear tags, blocked by weight and randomly assigned to 1 of 9 groups, as set forth above in table 4. If any test animal meeting the inclusion criteria was enrolled in the study and was later excluded for any reason, the Investigator and Monitor consulted in order to determine the use of data collected from the animal in the final analysis. The date of which enrolled piglets were excluded and the reason for exclusion was documented. Initially, no sows were excluded. A total of 108 of an available 110 pigs were randomly assigned to one of 9 groups on Day −3. The two smallest pigs (Nos. 17 and 19) were not assigned to a group and were available as extras, if needed. During the course of the study, several animals were removed. Pig 82 (Group 9) on Day −1, Pig No. 56 (Group 6) on Day 3, Pig No. 53 (Group 9) on Day 4, Pig No. 28 (Group 8) on Day 8, Pig No. 69 (Group 8) on Day 7, and Pig No. 93 (Group 4) on Day 9, were each found dead prior to challenge. These six pigs were not included in the final study results. Pig no 17 (one of the extra pigs) was assigned to Group 9. The remaining extra pig, No. 19, was excluded from the study.

The formulations given to each of the groups were as follows: Group 1 was designed to administer 1 ml of viral ORF2 (vORF2) containing 16 μg ORF2/ml. This was done by mixing 10.24 ml of viral ORF2 (256 μg/25 μg/ml=10.24 ml vORF2) with 3.2 ml of 0.5% Carbopol and 2.56 ml of phosphate buffered saline at a pH of 7.4. This produced 16 ml of formulation for group 1. Group 2 was designed to administer 1 ml of vORF2 containing 8 μg vORF2/ml. This was done by mixing 5.12 ml of vORF2 (128 μg/25 μg/ml=5.12 ml vORF2) with 3.2 ml of 0.5% Carbopol and 7.68 ml of phosphate buffered saline at a pH of 7.4. This produced 16 ml of formulation for group 2. Group 3 was designed to administer 1 ml of vORF2 containing 4 μg vORF2/ml. This was done by mixing 2.56 ml of vORF2 (64 μg/25 μg/ml=2.56 ml vORF2) with 3.2 ml of 0.5% Carbopol and 10.24 ml of phosphate buffered saline at a pH of 7.4. This produced 16 ml of formulation for group 3. Group 4 was designed to administer 1 ml of recombinant ORF2 (rORF2) containing 16 μg rORF2/ml. This was done by mixing 2.23 ml of rORF2 (512 μg/230 μg/ml=2.23 ml rORF2) with 6.4 ml of 0.5% Carbopol and 23.37 ml of phosphate buffered saline at a pH of 7.4. This produced 32 ml of formulation for group 4. Group 5 was designed to administer 1 ml of rORF2 containing 8 μg rORF2/ml. This was done by mixing 1.11 ml of rORF2 (256 μg/230 μg/ml=1.11 ml rORF2) with 6.4 ml of 0.5% Carbopol and 24.49 ml of phosphate-buffered saline at a pH of 7.4. This produced 32 ml of formulation for group 5. Group 6 was designed to administer 1 ml of rORF2 containing 8 μg rORF2/ml. This was done by mixing 0.56 ml of rORF2 (128 μg/230 μg/ml=0.56 ml rORF2) with 6.4 ml of 0.5% Carbopol and 25.04 ml of phosphate buffered saline at a pH of 7.4. This produced 32 ml of formulation for group 6. Group 7 was designed to administer 2 ml of PCV2 whole killed cell vaccine (PCV2 KV) containing the MAX PCV2 KV. This was done by mixing 56 ml of PCV2 KV with 14 ml of 0.5% Carbopol. This produced 70 ml of formulation for group 7. Finally group 8 was designed to administer KLH at 0.5 μg/ml or 1.0 μg/ml per 2 ml dose. This was done by mixing 40.71 ml KLH (7.0 μg protein/ml at 0.5 μg/ml=570 ml (7.0 μg/ml)(x)=(0.5)(570 ml)), 244.29 ml phosphate buffered saline at a pH of 7.4, and 285 ml Freunds adjuvant. Table 5 describes the time frames for the key activities of this Example.

TABLE 5

Study Activities

| Study Day | Study Activity |
|---|---|
| −4, 0 to 49 | General observations for overall health and clinical symptoms |
| −3 | Weighed; Randomized to groups; Collected blood samples from all pigs |
| 0 | Health examination; Administered IVP Nos. 1-7 to Groups 1-7, respectively |
| 0-7 | Observed pigs for injection site reactions |
| 14 | Boostered Group 7 with PCV2 Vaccine No. 7; Blood samples from all pigs |
| 14-21 | Observed Group 7 for injection site reactions |
| 16-19 | Treated all pigs with antibiotics (data missing) |
| 19 | Pigs transported from the first test site to a second test site |
| 21 | Treated Groups 1-9 with KLH/ICFA |
| 24 | Collected blood and nasal swab samples from all pigs; Weighed all pigs; Challenged Groups 1-8 with PCV2 challenge material |
| 25, 27, 29, 31, 33, 35, 37, 39, 41, 43, 45, 47 | Collected nasal swab samples from all pigs |
| 27 | Treated Groups 1-9 with KLH/ICFA |
| 31 | Collected blood samples from all pigs |
| 49 | Collected blood and nasal swab samples from all pigs; Weighed all pigs; Necropsy all pigs; Gross lesions noted with emphasis placed on icterus and gastric ulcers; Lungs evaluated for lesions; Fresh and formalin fixed tissue samples saved; In-life phase of the study completed |

Following completion of the in-life phase of the study, formalin fixed tissues were examined by Immunohistochemistry (IHC) for detection of PCV2 antigen by a pathologist, blood samples were evaluated for PCV2 serology, nasal swab samples were evaluated for PCV2 shedding, and average daily weight gain (ADWG) was determined from Day 24 to Day 49.

Animals were housed at the first study site in individual cages in five rooms from birth to approximately 11 days of age (approximately Day 0 of the study). Each room was identical in layout and consisted of stacked individual stainless steel cages with heated and filtered air supplied separately to each isolation unit. Each room had separate heat and ventilation, thereby preventing cross-contamination of air between rooms. Animals were housed in two different buildings at the second study site. Group 9 (The Strict negative control group) was housed separately in a converted finisher building and Groups 1-8 were housed in converted nursery building. Each group was housed in a separate pen (11-12 pigs per pen) and each pen provided approximately 3.0 square feet per pig. Each pen was on an elevated deck with plastic slatted floors. A pit below the pens served as a holding tank for excrement and waste. Each building had its own separate heating and ventilation systems, with little likelihood of cross-contamination of air between buildings.

At the first study site, piglets were fed a specially formulated milk ration from birth to approximately 3 weeks of age. All piglets were consuming solid, special mixed ration by Day 19 (approximately 4½ weeks of age). At the second study site, all piglets were fed a custom non-medicated commercial mix ration appropriate for their age and weight, ad libitum. Water at both study sites was also available ad libitum.

All test pigs were treated with Vitamin E on Day −2, with iron injections on Day −1 and with NAXCEL® (1.0 mL, IM, in alternating hams) on Days 16, 17, 18 and 19. In addition, Pig No. 52 (Group 9) was treated with an iron injection on Day 3, Pig 45 (Group 6) was treated with an iron injection on Day 11, Pig No. 69 (Group 8) was treated with NAXCEL® on Day 6, Pig No. 74 (Group 3) was treated with dexamethazone and penicillin on Day 14, and Pig No. 51 (Group 1) was treated with dexamethazone and penicillin on Day 13 and with NAXCEL® on Day 14 for various health reasons.

While at both study sites, pigs were under veterinary care Animal health examinations were conducted on Day 0 and were recorded on the Health Examination Record Form. All animals were in good health and nutritional status before vaccination as determined by observation on Day 0. All test animals were observed to be in good health and nutritional status prior to challenge. Carcasses and tissues were disposed of by rendering. Final disposition of study animals was records on the Animal Disposition Record.

On Day 0, pigs assigned to Groups 1-6 received 1.0 mL of PCV2 Vaccines 1-6, respectively, IM in the left neck region using a sterile 3.0 mL Luer-lock syringe and a sterile 20 g×½" needle. Pigs assigned to Group 7 received 2.0 mL of PCV2 Vaccine No. 7 IM in the left neck region using a sterile 3.0 mL Luer-lock syringe and a sterile 20 g×½" needle. On Day 14, pigs assigned to Group 7 received 2.0 mL of PCV2 Vaccine No. 7 IM in the right neck region using a sterile 3.0 mL Luer-lock syringe and a sterile 20 g×½" needle.

On Day 21 all test pigs received 2.0 mL of KLH/ICFA IM in the right ham region using a sterile 3.0 mL Luer-lock syringe and a sterile 20 g×1" needle. On Day 27 all test pigs received 2.0 mL of KLH/ICFA in the left ham region using a sterile 3.0 mL Luer-lock syringe and a sterile 20 g×1" needle.

On Day 24, pigs assigned to Groups 1-8 received 1.0 mL of PCV2 ISUVDL challenge material (5.11 $\log_{10}$ TCID$_{50}$/mL) IM in the left neck region using a sterile 3.0 mL Luer-lock syringe and a sterile 20 g×1" needle. An additional 1.0 mL of the same material was administered IN to each pig (0.5 mL per nostril) using a sterile 3.0 mL Luer-lock syringe and nasal canula.

Test pigs were observed daily for overall health and adverse events on Day −4 and from Day 0 to Day 19. Observations were recorded on the Clinical Observation Record. All test pigs were observed from Day 0 to Day 7, and Group 7 was further observed from Day 14 to 21, for injection site reactions. Average daily weight gain was determined by weighing each pig on a calibrated scale on Days −3, 24 and 49, or on the day that a pig was found dead after challenge. Body weights were recorded on the Body Weight Form. Day −3 body weights were utilized to block pigs prior to randomization. Day 24 and Day 49 weight data was utilized to determine the average daily weight gain (ADWG) for each pig during these time points. For pigs that died after challenge and before Day 49, the ADWG was adjusted to represent the ADWG from Day 24 to the day of death.

In order to determine PCV2 serology, venous whole blood was collected from each piglet from the orbital venous sinus on Days −3 and 14. For each piglet, blood was collected from the orbital venous sinus by inserting a sterile capillary tube into the medial canthus of one of the eyes and draining approximately 3.0 mL of whole blood into a 4.0 mL Serum Separator Tube (SST). On Days 24, 31, and 49, venous whole blood from each pig was collected from the anterior vena cava using a sterile 18 g×1½" Vacutainer needle (Becton Dickinson and Company, Franklin Lakes, N.J.), a Vacutainer needle holder and a 13 mL SST. Blood collections at each time point were recorded on the Sample Collection Record. Blood in each SST was allowed to clot, each SST was then spun down and the serum harvested. Harvested serum was transferred to a sterile snap tube and stored at −70±10° C. until tested at a later date. Serum samples were tested for the presence of PCV2 antibodies by BIVI-R&D personnel.

Pigs were observed once daily from Day 20 to Day 49 for clinical symptoms and clinical observations were recorded on the Clinical Observation Record.

To test for PCV2 nasal shedding, on Days 24, 25, and then every other odd numbered study day up to and including Day 49, a sterile dacron swab was inserted intra nasally into either the left or right nostril of each pig (one swab per pig) as aseptically as possible, swished around for a few seconds and then removed. Each swab was then placed into a single sterile snap-cap tube containing 1.0 mL of EMEM media with 2% II-BS, 500 units/mL of Penicillin, 500 μg/mL of Streptomycin and 2.5 μg/mL of Fungizone. The swab was broken off in the tube, and the snap tube was sealed and appropriately labeled with animal number, study number, date of collection, study day and "nasal swab." Sealed snap tubes were stored at −40±10° C. until transported overnight on ice to BIVI-St. Joseph. Nasal swab collections were recorded on the Nasal Swab Sample Collection Form. BIVI-R&D conducted quantitative virus isolation (VI) testing for PCV2 on nasal swab samples. The results were expressed in $\log_{10}$ values. A value of 1.3 logs or less was considered negative and any value greater than 1.3 logs was considered positive.

Pigs that died (Nos. 28, 52, 56, 69, 82, and 93) at the first study site were necropsied to the level necessary to determine a diagnosis. Gross lesions were recorded and no tissues were retained from these pigs. At the second study site, pigs that died prior to Day 49 (Nos. 45, 23, 58, 35), pigs found dead on Day 49 prior to euthanasia (Nos. 2, 43), and pigs euthanized on Day 49 were necropsied. Any gross lesions were noted and the percentages of lung lobes with lesions were recorded on the Necropsy Report Form.

From each of the 103 pigs necropsied at the second study site, a tissue sample of tonsil, lung, heart, liver, mesenteric lymph node, kidney and inguinal lymph node was placed into a single container with buffered 10% formalin; while another tissue sample from the same aforementioned organs was placed into a Whirl-pak (M-Tech Diagnostics Ltd., Thelwall, UK) and each Whirl-pak was placed on ice. Each container was properly labeled. Sample collections were recorded on the Necropsy Report Form. Afterwards, formalin-fixed tissue samples and a Diagnostic Request Form were submitted for IHC testing. IHC testing was conducted in accordance with standard ISU laboratory procedures for receiving samples, sample and slide preparation, and staining techniques. Fresh tissues in Whirl-paks were shipped with ice packs to the Study Monitor for storage (−70°±10° C.) and possible future use. Formalin-fixed tissues were examined by a pathologist for detection of PCV2 by IHC and scored using the following scoring system: 0=None; 1=Scant positive staining, few sites; 2=Moderate positive staining, multiple sites; and 3=Abundant positive staining, diffuse throughout the tissue. Due to the fact that the pathologist could not positively differentiate inguinal LN from mesenteric LN, results for these tissues were simply labeled as Lymph Node and the score given the highest score for each of the two tissues per animal.

Results

Results for this example are given below. It is noted that one pig from Group 9 died before Day 0, and 5 more pigs died post-vaccination (1 pig from Group 4; 1 pig from Group 6; 2 pigs from Group 8; and 1 pig from Group 9). Post-mortem examination indicated all six died due to underlying infections that were not associated with vaccination or PMWS. Additionally, no adverse events or injection site reactions were noted with any groups.

Average daily weight gain (ADWG) results are presented below in Table 6. Group 9, the strict negative control group, had the highest ADWG (1.06±0.17 lbs/day), followed by Group 5 (0.94±0.22 lbs/day), which received one dose of 8 µg of rORF2. Group 3, which received one dose of 4 µg of vORF2, had the lowest ADWG (0.49±0.21 lbs/day), followed by Group 7 (0.50±0.15 lbs/day), which received 2 doses of killed vaccine.

TABLE 6

Summary of Group Average Daily Weight Gain (ADWG)

| Group | Treatment | N | ADWG - lbs/day (Day 24 to Day 49) or adjusted for pigs dead before Day 29 |
|---|---|---|---|
| 1 | vORF2 - 16 µg (1 dose) | 12 | 0.87 ± 0.29 lbs/day |
| 2 | vORF2 - 8 µg (1 dose) | 12 | 0.70 ± 0.32 lbs/day |
| 3 | vORF2 - 4 µg (1 dose) | 12 | 0.49 ± 0.21 lbs/day |
| 4 | rORF2 - 16 µg (1 dose) | 11 | 0.84 ± 0.30 lbs/day |
| 5 | rORF2 - 8 µg (1 dose) | 12 | 0.94 ± 0.22 lbs/day |
| 6 | rORF2 - 4 µg (1 dose) | 11 | 0.72 ± 0.25 lbs/day |
| 7 | KV (2 doses) | 12 | 0.50 ± 0.15 lbs/day |
| 8 | Challenge Controls | 10 | 0.76 ± 0.19 lbs/day |
| 9 | Strict Negative Controls | 11 | 1.06 ± 0.17 lbs/day | vORF2 = isolated viral ORF2;
rORF2 = recombinant baculovirus expressed ORF2;
killed whole cell virus = PCV2 virus grown in suitable cell culture PCV2 serology results are presented below in Table 7. All nine groups were seronegative for PCV2 on Day −3. On Day 14, Groups receiving vORF2 vaccines had the highest titers, which ranged from 187.5 to 529.2. Pigs receiving killed viral vaccine had the next highest titers, followed by the groups receiving rORF2 vaccines. Groups 8 and 9 remained seronegative at this time. On Day 24 and Day 31, pigs receiving vORF2 vaccines continued to demonstrate a strong serological response, followed closely by the group that received two doses of a killed viral vaccine. Pigs receiving rORF2 vaccines were slower to respond serologically and Groups 8 and 9 continued to remain seronegative. On Day 49, pigs receiving vORF2 vaccine, 2 doses of the killed viral vaccine and the lowest dose of rORF2 demonstrated the strongest serological responses. Pigs receiving 16 µg and 8 µg of rORF2 vaccines had slightly higher IFA titers than challenge controls. Group 9 on Day 49 demonstrated a strong serological response.

TABLE 7

Summary of Group PCV2 IFA Titers
AVERAGE IFA TITER

| Group | Treatment | Day-3 | Day 14 | Day 24 | Day 31** | Day 49*** |
|---|---|---|---|---|---|---|
| 1 | vORF2-16 µg (1 dose) | 50.0 | 529.2 | 4400.0 | 7866.7 | 11054.5 |
| 2 | vORF2-8 µg (1 dose) | 50.0 | 500.0 | 3466.7 | 6800.0 | 10181.8 |
| 3 | vORF2-4 µg (1 dose) | 50.0 | 187.5 | 1133.3 | 5733.3 | 9333.3 |
| 4 | rORF2-16 µg (1 dose) | 50.0 | 95.5 | 1550.0 | 3090.9 | 8000.0 |
| 5 | rORF2-8 µg (1 dose) | 50.0 | 75.0 | 887.5 | 2266.7 | 7416.7 |
| 6 | rORF2-4 µg (1 dose) | 50.0 | 50.0 | 550.0 | 3118.2 | 10570.0 |
| 7 | KV (2 doses) | 50.0 | 204.2 | 3087.5 | 4620.8 | 8680.0 |
| 8 | Challenge Controls | 50.0 | 55.0 | 50.0 | 50.0 | 5433.3 |
| 9 | Strict Negative Controls | 50.0 | 59.1 | 59.1 | 54.5 | 6136.4 | vORF2 = isolated viral ORF2;
rORF2 = recombinant baculovirus expressed ORF2;
killed whole cell virus = PCV2 virus grown in suitable cell culture
*For calculation purposes, a ≤100 IFA titer was designated as a titer of "50"; a ≥6400 IFA titer was designated as a titer of "12,800".
**Day of Challenge
***Day of Necropsy The results from the post-challenge clinical observations are presented below in Table 8. This summary of results includes observations for Abnormal Behavior, Abnormal Respiration, Cough and Diarrhea. Table 9 includes the results from the Summary of Group Overall Incidence of Clinical Symptoms and Table 10 includes results from the Summary of Group Mortality Rates Post-challenge. The most common clinical symptom noted in this study was abnormal behavior, which was scored as mild to severe lethargy. Pigs receiving the 2 lower doses of vORF2, pigs receiving 16 µg of rORF2 and pigs receiving 2 doses of KV vaccine had incidence rates of ≥27.3%. Pigs receiving 8 µg of rORF2 and the strict negative control group had no abnormal behavior. None of the pigs in this study demonstrated any abnormal respiration. Coughing was noted frequently in all groups (0 to 25%), as was diarrhea (0-20%). None of the clinical symptoms noted were pathognomic for PMWS.

The overall incidence of clinical symptoms varied between groups. Groups receiving any of the vORF2 vaccines, the group receiving 16 µg of rORF2, the group receiving 2 doses of KV vaccine, and the challenge control group had the highest incidence of overall clinical symptoms (≥36.4%). The strict negative control group, the group receiving 8 µg of rORF2 and the group receiving 4 µg of rORF2 had overall incidence rates of clinical symptoms of 0%, 8.3% and 9.1%, respectively.

Overall mortality rates between groups varied as well. The group receiving 2 doses of KV vaccine had the highest mortality rate (16.7%); while groups that received 4 µg of vORF2, 16 µg of rORF2, or 8 µg of rORF2 and the strict negative control group all had 0% mortality rates.

TABLE 8

Summary of Group Observations for Abnormal Behavior, Abnormal Respiration, Cough, and Diarrhea

| Group | Treatment | N | Abnormal Behavior[1] | Abnormal Behavior[2] | Cough[3] | Diarrhea[4] |
|---|---|---|---|---|---|---|
| 1 | vORF2-16 µg (1 dose) | 12 | 2/12 (16.7%) | 0/12 (0%) | 3/12 (25%) | 2/12 (16/7%) |

TABLE 8-continued

Summary of Group Observations for Abnormal Behavior, Abnormal Respiration, Cough, and Diarrhea

| Group | Treatment | N | Abnormal Behavior[1] | Abnormal Behavior[2] | Cough[3] | Diarrhea[4] |
|---|---|---|---|---|---|---|
| 2 | vORF2-8 μg (1 dose) | 12 | 4/12 (33.3%) | 0/12 (0%) | 1/12 (8.3%) | 1/12 (8.3%) |
| 3 | vORF2-4 μg (1 dose) | 12 | 8/12 (66.7%) | 0/12 (0%) | 2/12 (16.7%) | 1/12 (8.3%) |
| 4 | rORF2-16 μg (1 dose) | 11 | 3/11 (27.3%) | 0/11 (0%) | 0/11 (0%) | 2/11 (18.2%) |
| 5 | rORF2-8 μg (1 dose) | 12 | 0/12 (0%) | 0/12 (0%) | 1/12 (8.3%) | 0/12 (0%) |
| 6 | rORF2-4 μg (1 dose) | 11 | 1/11 (9.1%) | 0/11 (0%) | 0/11 (0%) | 0/12 (0%) |
| 7 | KV (2 doses) | 12 | 7/12 (58.3) | 0/12 (0%) | 0/12 (0%) | 1/12 (8.3%) |
| 8 | Challenge Controls | 10 | 1/10 (10%) | 0/10 (0%) | 2/10 (20%) | 2/10 (20%) |
| 9 | Strict Negative Controls | 11 | 0/11 (0%) | 0/11 (0%) | 0/11 (0%) | 0/11 (0%) | vORF2 = isolated viral ORF2;
rORF2 = recombinant baculovirus expressed ORF2;
killed whole cell virus = PCV2 virus grown in suitable cell culture
[1]Total number of pigs in each group that demonstrated any abnormal behavior for at least one day
[2]Total number of pigs in each group that demonstrated any abnormal respiration for at least one day
[3]Total number of pigs in each group that demonstrated a cough for at least one day
[4]Total number of pigs in each group that demonstrated diarrhea for at least one day

TABLE 9

Summary of Group Overall Incidence of Clinical Symptoms

| Group | Treatment | N | Incidence of pigs with Clinical Symptoms[1] | Incidence Rate |
|---|---|---|---|---|
| 1 | vORF2 - 16 μg (1 dose) | 12 | 5 | 41.7% |
| 2 | vORF2 - 8 μg (1 dose) | 12 | 5 | 41.7% |
| 3 | vORF2 - 4 μg (1 dose) | 12 | 8 | 66.7% |
| 4 | rORF2 - 16 μg (1 dose) | 11 | 4 | 36.4% |
| 5 | rORF2 - 8 μg (1 dose) | 12 | 1 | 8.3% |
| 6 | rORF2 - 4 μg (1 dose) | 11 | 1 | 9.1% |
| 7 | KV (2 doses) | 12 | 7 | 58.3% |
| 8 | Challenge Controls | 10 | 4 | 40% |
| 9 | Strict Negative Controls | 11 | 0 | 0% | vORF2 = isolated viral ORF2;
rORF2 = recombinant baculovirus expressed ORF2;
killed whole cell virus = PCV2 virus grown in suitable cell culture
[1]Total number of pigs in each group that demonstrated any clinical symptom for at least one day

TABLE 10

Summary of Group Mortality Rates Post-challenge

| Group | Treatment | N | Dead Post-challenge | Mortality Rate |
|---|---|---|---|---|
| 1 | vORF2 - 16 μg (1 dose) | 12 | 1 | 8.3% |
| 2 | vORF2 - 8 μg (1 dose) | 12 | 1 | 8.3% |
| 3 | vORF2 - 4 μg (1 dose) | 12 | 0 | 0% |
| 4 | rORF2 - 16 μg (1 dose) | 11 | 0 | 0% |
| 5 | rORF2 - 8 μg (1 dose) | 12 | 0 | 0% |
| 6 | rORF2 - 4 μg (1 dose) | 11 | 1 | 9.1% |
| 7 | KV (2 doses) | 12 | 2 | 16.7% |
| 8 | Challenge Controls | 10 | 1 | 10% |
| 9 | Strict Negative Controls | 11 | 0 | 0% | vORF2 = isolated viral ORF2;
rORF2 = recombinant baculovirus expressed ORF2;
killed whole cell virus = PCV2 virus grown in suitable cell culture PCV2 nasal shedding results are presented below in Table 11. Following challenge on Day 24, 1 pig in Group 7 began shedding PCV2 on Day 27. None of the other groups experienced shedding until Day 33. The bulk of nasal shedding was noted from Day 35 to Day 45. Groups receiving any of the three vORF2 vaccines and groups receiving either 4 or 8 μg of rORF2 had the lowest incidence of nasal shedding of PCV2 (≤9.1%). The challenge control group (Group 8) had the highest shedding rate (80%), followed by the strict negative control group (Group 9), which had an incidence rate of 63.6%.

TABLE 11

Summary of Group Incidence of Nasal Shedding of PCV2

| Group | Treatment | N | No. Of pigs that shed for at least one day | Incidence Rate |
|---|---|---|---|---|
| 1 | vORF2 - 16 μg (1 dose) | 12 | 1 | 8.3% |
| 2 | vORF2 - 8 μg (1 dose) | 12 | 1 | 8.3% |
| 3 | vORF2 - 4 μg (1 dose) | 12 | 1 | 8.3% |
| 4 | rORF2 - 16 μg (1 dose) | 11 | 2 | 18.2% |
| 5 | rORF2 - 8 μg (1 dose) | 12 | 1 | 8.3% |
| 6 | rORF2 - 4 μg (1 dose) | 11 | 1 | 9.1% |
| 7 | KV (2 doses) | 12 | 5 | 41.7% |
| 8 | Challenge Controls | 10 | 8 | 80% |
| 9 | Strict Negative Controls | 11 | 7 | 63.6% | vORF2 = isolated viral ORF2;
rORF2 = recombinant baculovirus expressed ORF2;
killed whole cell virus = PCV2 virus grown in suitable cell culture The Summary of Group Incidence of Icterus, Group Incidence of Gastric Ulcers, Group Mean Lung Lesion Scores, and Group Incidence of Lung Lesions are shown below in Table 12. Six pigs died at the first test site during the post-vaccination phase of the study (Group 4, N=1; Group 6, N=1; Group 8, N=2; Group 9, N=2). Four out of six pigs had fibrinous lesions in one or more body cavities, one pig (Group 6) had lesions consistent with clostridial disease, and one pig (Group 9) had no gross lesions. None of the pigs that died during the post-vaccination phased of the study had lesions consistent with PMWS.

Pigs that died post-challenge and pigs euthanized on Day 49 were necropsied. At necropsy, icterus and gastric ulcers were not present in any group. With regard to mean % lung lesions, Group 9 had lowest mean % lung lesions (0%), followed by Group 1 with 0.40±0.50% and Group 5 with 0.68±1.15%. Groups 2, 3, 7 and 8 had the highest mean % lung lesions (≥7.27%). Each of these four groups contained one pig with % lung lesions ≥71.5%, which skewed the results higher for these four groups. With the exception of Group 9 with 0% lung lesions noted, the remaining 8 groups had ≤36% lung lesions. Almost all lung lesions noted were described as red/purple and consolidated.

TABLE 12

Summary of Group Incidence of Icterus, Group Incidence of Gastric Ulcers, Group Mean % Lung Lesion Scores, and Group Incidence of Lung Lesions Noted

| Group | Treatment | Icterus | Gastric Ulcers | Mean % Lung Lesions | Incidence of Lung Lesions Noted |
|---|---|---|---|---|---|
| 1 | vORF2 - 16 μg (1 dose) | 0/12 (0%) | 0/12 (0%) | 0.40 ± 0.50% | 10/12 (83%) |
| 2 | vORF2 - 8 μg (1 dose) | 0/12 (0%) | 0/12 (0%) | 7.41 ± 20.2% | 10/12 (83%) |
| 3 | vORF2 - 4 μg (1 dose) | 0/12 (0%) | 0/12 (0%) | 9.20 ± 20.9% | 10/12 (83%) |
| 4 | rORF2 - 16 μg (1 dose) | 0/11 (0%) | 0/11 (0%) | 1.5 ± 4.74% | 4/11 (36%) |
| 5 | rORF2 - 8 μg (1 dose) | 0/12 (0%) | 0/12 (0%) | 0.68 ± 1.15% | 9/12 (75%) |

TABLE 12-continued

Summary of Group Incidence of Icterus, Group Incidence of Gastric Ulcers, Group Mean % Lung Lesion Scores, and Group Incidence of Lung Lesions Noted

| Group | Treatment | Icterus | Gastric Ulcers | Mean % Lung Lesions | Incidence of Lung Lesions Noted |
|---|---|---|---|---|---|
| 6 | rORF2 - 4 µg (1 dose) | 0/11 (0%) | 0/11 (0%) | 2.95 ± 5.12% | 7/11 (64%) |
| 7 | KV (2 doses) | 0/12 (0%) | 0/12 (0%) | 7.27 ± 22.9% | 9/12 (75%) |
| 8 | Challenge Controls | 0/10 (0%) | 0/10 (0%) | 9.88 ± 29.2% | 8/10 (80%) |
| 9 | Strict Negative Controls | 0/11 (0%) | 0/11 (0%) | 0/11 (0%) | 0/11 (0%) | vORF2 = isolated viral ORF2;
rORF2 = recombinant baculovirus expressed ORF2;
KV or killed whole cell virus = PCV2 virus grown in suitable cell culture The Summary of Group IHC Positive Incidence Results is shown in Table 13. Group 1 (vORF2—16 µg) and Group 5 (rORF2—8 µg) had the lowest rate of IHC positive results (16.7%). Group 8 (Challenge Controls) and Group 9 (Strict Negative Controls) had the highest rate of IHC positive results, 90% and 90.9%, respectively.

TABLE 13

Summary of Group IHC Positive Incidence Rate

| Group | Treatment | N | No. Of pigs that had at least one tissue positive for PCV2 | Incidence Rate |
|---|---|---|---|---|
| 1 | vORF2 - 16 µg (1 dose) | 12 | 2 | 16.7% |
| 2 | vORF2 - 8 µg (1 dose) | 12 | 3 | 25.0% |
| 3 | vORF2 - 4 µg (1 dose) | 12 | 8 | 66.7% |
| 4 | rORF2 - 16 µg (1 dose) | 11 | 4 | 36.3% |
| 5 | rORF2 - 8 µg (1 dose) | 12 | 2 | 16.7% |
| 6 | rORF2 - 4 µg (1 dose) | 11 | 4 | 36.4% |
| 7 | KV (2 doses) | 12 | 5 | 41.7% |
| 8 | Challenge Controls | 10 | 9 | 90.0% |
| 9 | Strict Negative Controls | 11 | 10 | 90.9% | vORF2 = isolated viral ORF2;
rORF2 = recombinant baculovirus expressed ORF2;
KV or killed whole cell virus = PCV2 virus grown in suitable cell culture Post-challenge, Group 5, which received one dose of 8 µg of rORF2 antigen, outperformed the other 6 vaccine groups. Group 5 had the highest ADWG (0.94±0.22 lbs/day), the lowest incidence of abnormal behavior (0%), the second lowest incidence of cough (8.3%), the lowest incidence of overall clinical symptoms (8.3%), the lowest mortality rate (0%), the lowest rate of nasal shedding of PCV2 (8.3%), the second lowest rate for mean % lung lesions (0.68±1.15%) and the lowest incidence rate for positive tissues (16.7%). Groups receiving various levels of rORF2 antigen overall outperformed groups receiving various levels of vORF2 and the group receiving 2 doses of killed whole cell PCV2 vaccine performed the worst. Tables 14 and 15 contain summaries of group post-challenge data.

TABLE 14

Summary of Group Post-Challenge Data-Part 1

| Group | N | Treatment | ADWG (lbs/day) | Abnormal Behavior | Cough | Overall Incidence of Clinical Symptoms |
|---|---|---|---|---|---|---|
| 1 | 12 | vORF2-16 µg (1 dose) | 0.87 ± 0.29 | 2/12 (16.7%) | 3/12 (25%) | 41.7% |
| 2 | 12 | vORF2-8 µg (1 dose) | 0.70 ± 0.32 | 4/12 (33.3%) | 1/12 (8.3%) | 41.7% |
| 3 | 12 | vORF2-4 µg (1 dose) | 0.49 ± 0.21 | 8/12 (66.7%) | 2/12 (16.7%) | 66.7% |
| 4 | 11 | rORF2-16 µg (1 dose) | 0.84 ± 0.30 | 3/11 (27.3%) | 0/11 (0%) | 36.4% |
| 5 | 12 | rORF2-8 µg (1 dose) | 0.94 ± 0.22 | 0/12 (0%) | 1/12 (8.3%) | 8.3% |
| 6 | 11 | rORF2-4 µg (1 dose) | 0.72 ± 0.25 | 1/11 (9.1%) | 0/11 (0%) | 9.1% |
| 7 | 12 | KV (2 doses) | 0.50 ± 0.15 | 7/12 (58.3) | 0/12 (0%) | 58.3% |
| 8 | 10 | Challenge Controls | 0.76 ± 0.19 | 1/10 (10%) | 2/10 (20%) | 40% |
| 9 | 11 | Strict Negative Controls | 1.06 ± 0.17 | 0/11 (0%) | 0/11 (0%) | 0% | vORF2 = isolated viral ORF2;
rORF2 = recombinant baculovirus expressed ORF2;
KV or killed whole cell virus = PCV2 virus grown in suitable cell culture

TABLE 15

Summary of Group Post-Challenge Data-Part 2

| Group | N | Treatment | Mortality Rate | Nasal Shedding | Mean % Lung Lesions | Incidence Rate of at least one tissue IHC positive for PCV2 |
|---|---|---|---|---|---|---|
| 1 | 12 | vORF2-16 µg (1 dose) | 8.3% | 8.3% | 0.40 ± 0.50% | 16.7% |
| 2 | 12 | vORF2-8 µg (1 dose) | 8.3% | 8.3% | 7.41 ± 20.2% | 25.0% |
| 3 | 12 | vORF2-4 µg (1 dose) | 0% | 8.3% | 9.20 ± 20.9% | 66.7% |
| 4 | 11 | rORF2-16 µg (1 dose) | 0% | 18.2% | 1.50 ± 4.74% | 36.3% |
| 5 | 12 | rORF2-8 µg (1 dose) | 0% | 8.3% | 0.68 ± 1.15% | 16.7% |
| 6 | 11 | rORF2-4 µg (1 dose) | 9.1% | 9.1% | 2.95 ± 5.12% | 36.4% |
| 7 | 12 | KV (2 doses) | 16.7% | 41.7% | 7.27 ± 22.9% | 41.7% |
| 8 | 10 | Challenge Controls | 10% | 80% | 9.88 ± 29.2% | 90.0% |
| 9 | 11 | Strict Negative Controls | 0% | 63.6% | 0/11 (0%) | 90.9% | vORF2 = isolated viral ORF2;
rORF2 = recombinant baculovirus expressed ORF2;
KV or killed whole cell virus = PCV2 virus grown in suitable cell culture Results of this study indicate that all further vaccine efforts should focus on a rORF2 vaccine. Overall, nasal shedding of PCV2 was detected post-challenge and vaccination with a PCV2 vaccine resulted in a reduction of shedding. Immunohistochemistry of selected lymphoid tissues also served as a good parameter for vaccine efficacy, whereas large differences in ADWG, clinical symptoms, and gross lesions were not detected between groups. This study was complicated by the fact that extraneous PCV2 was introduced at some point during the study, as evidenced by nasal shedding of PCV2, PCV2 seroconversion and positive IHC tissues in Group 9, the strict negative control group.

Discussion

Seven PCV2 vaccines were evaluated in this study, which included three different dose levels of vORF2 antigen administered once on Day 0, three different dose levels of rORF2 antigen administered once on Day 0 and one dose level of killed whole cell PCV2 vaccine administered on Day 0 and Day 14. Overall, Group 5, which received 1 dose of vaccine containing 8 μg of rORF2 antigen, had the best results. Group 5 had the highest ADWG, the lowest incidence of abnormal behavior, the lowest incidence of abnormal respiration, the second lowest incidence of cough, the lowest incidence of overall clinical symptoms, the lowest mortality rate, the lowest rate of nasal shedding of PCV2, the second lowest rate for mean % lung lesions and the lowest incidence rate for positive IHC tissues.

Interestingly, Group 4, which received a higher dose of rORF2 antigen than Group 5, did not perform as well or better than Group 5. Group 4 had a slightly lower ADWG, a higher incidence of abnormal behavior, a higher incidence of overall clinical symptoms, a higher rate of nasal shedding of PCV2, a higher mean % lung lesions, and a higher rate for positive IHC tissues than Group 5. Statistical analysis, which may have indicated that the differences between these two groups were not statistically significant, was not conducted on these data, but there was an observed trend that Group 4 did not perform as well as Group 5.

Post-vaccination, 6 pigs died at the first study site. Four of the six pigs were from Group 8 or Group 9, which received no vaccine. None of the six pigs demonstrated lesions consistent with PMWS, no adverse events were reported and overall, all seven vaccines appeared to be safe when administered to pigs approximately 11 days of age. During the post-vaccination phase of the study, pigs receiving either of three dose levels of vORF2 vaccine or killed whole cell vaccine had the highest IFAT levels, while Group 5 had the lowest IFAT levels just prior to challenge, of the vaccine groups.

Although not formally proven, the predominant route of transmission of PCV2 to young swine shortly after weaning is believed to be by oronasal direct contact and an efficacious vaccine that reduces nasal shedding of PCV2 in a production setting would help control the spread of infection. Groups receiving one of three vORF2 antigen levels and the group receiving 8 μg of rORF2 had the lowest incidence rate of nasal shedding of PCV2 (8.3%). Expectedly, the challenge control group had the highest incidence rate of nasal shedding (80%).

Gross lesions in pigs with PMWS secondary to PCV2 infection typically consist of generalized lymphadenopathy in combination with one or a multiple of the following: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc. At necropsy, icterus, hepatitis, nephritis, and gastric ulcers were not noted in any groups and lymphadenopathy was not specifically examined for. The mean % lung lesion scores varied between groups. The group receiving 16 μg of vORF2 antigen had the lowest mean % lung lesion score (0.40±0.50%), followed by the group that received 8 μg of rORF2 (0.68±1.15%). As expected, the challenge control group had the highest mean % lung lesion score (9.88±29.2%). In all four groups, the mean % lung lesion scores were elevated due to one pig in each of these groups that had very high lung lesion scores. Most of the lung lesions were described as red/purple and consolidated. Typically, lung lesions associated with PMWS are described as tan and non-collapsible with interlobular edema. The lung lesions noted in this study were either not associated with PCV2 infection or a second pulmonary infectious agent may have been present. Within the context of this study, the % lung lesion scores probably do not reflect a true measure of the amount of lung infection due to PCV2.

Other researchers have demonstrated a direct correlation between the presence of PCV2 antigen by IHC and histopathology. Histopathology on select tissues was not conducted with this study. Group 1 (16 μg of vORF2) and Group 5 (8 μg of rORF2) had the lowest incidence rate of pigs positive for PCV2 antigen (8.3%), while Group 9 (the strict negative control group—90.9%) and Group 8 (the challenge control group—90.0%) had the highest incidence rates for pigs positive for PCV2 antigen. Due to the non-subjective nature of this test, IHC results are probably one of the best parameters to judge vaccine efficacy on.

Thus, in one aspect of the present invention, the Minimum Protective Dosage (MPD) of a 1 ml/1 dose recombinant product with extracted PCV2 ORF2 (rORF2) antigen in the CDCD pig model in the face of a PCV2 challenge was determined Of the three groups that received varying levels of rORF2 antigen, Group 5 (8 μg of rORF2 antigen) clearly had the highest level of protection. Group 5 either had the best results or was tied for the most favorable results with regard to all of the parameters examined. When Group 5 was compared with the other six vaccine groups post-challenge, Group 5 had the highest ADWG (0.94±0.22 lbs/day), the lowest incidence of abnormal behavior (0%), the second lowest incidence of cough (8.3%), the lowest incidence of overall clinical symptoms (8.3%), the lowest mortality rate (0%), the lowest rate of nasal shedding of PCV2 (8.3%), the second lowest rate for mean % lung lesions (0.68±1.15%) and the lowest incidence rate for positive IHC tissues (16.7%).

In another aspect of the present invention, the MPD of a 1 ml/1 dose conventional product that is partially purified PCV2 ORF2 (vORF2) antigen in the CDCD pig model in the face of a PCV2 challenge was determined Of the three groups that received varying levels of vORF2 antigen, Group 1 (16 μg of vORF2) had the highest level of protection. Group 1 outperformed Groups 2 and 3 with respect to ADWG, mean % lung lesions, and IHC. Groups 1 and 2 (8 μg of vORF2 antigen) performed equally with respect to overall incidence of clinical symptoms, Group 3 (4 μg of vORF2 antigen) had the lowest mortality rate, and all three groups performed equally with respect to nasal shedding. Overall, vORF vaccines did not perform as well as rORF vaccines.

In yet another aspect of the present invention, the efficacy of a maximum dose of a 2 ml/2 dose Conventional Killed PCV2 vaccine in the CDCD pig model in the face of a PCV2 challenge was determined Of the seven vaccines evaluated in this study, the killed whole cell PCV2 vaccine performed the worst. Piglets receiving two doses of killed whole cell PCV2 vaccine had the lowest ADWG, the second highest rate of abnormal behavior (58.3%), the second highest overall incidence of clinical symptoms (58.3%), the highest mortality rate (16.7%), the second highest incidence of nasal shedding (41.7%), highest mean % lung lesions (9.88±29.2%), a high incidence of lung lesions noted (75%) and a moderate IHC incidence rate in tissues (41.7%). However, it was still effective at invoking an immune response.

In still another aspect of the present invention, nasal shedding of PCV2 was assessed as an efficacy parameter and the previous PCV2 efficacy parameters from previous studies were reconfirmed. Results from this study indicate that nasal shedding of PCV2 occurs following intra nasal challenge and that PCV2 vaccines reduce nasal shedding of PCV2 post-challenge. Furthermore, results from this study and reports in the literature indicate that IHC should continue to be evaluated in future PCV2 vaccine trials as well.

Some additional conclusions arising from this study are that lymphadenopathy is one of the hallmarks of PMWS. Another one of the hallmarks of PMWS is lymphoid depletion and multinucleated/giant histiocytes. Additionally, no adverse events or injection site reactions were noted for any of the 7 PCV2 vaccines and all 7 PCV2 vaccines appeared to be safe when administered to young pigs.

Example 5

This example tests the efficacy of eight PCV2 candidate vaccines and reconfirms PCV2 challenge parameters from earlier challenge studies following exposure to a virulent strain of PCV2. One hundred and fifty (150) cesarean derived colostrum deprived (CDCD) piglets, 6-16 days of age, were blocked by weight and randomly divided into 10 groups of equal size. Table 16 sets forth the General Study Design for this Example.

TABLE 16

General Study Design

| Group | No. Of Pigs | Treatment | Day of Treatment | KLH/ICFA on Day 22 and Day 28 | Challenge with Virulent PCV2 on Day 25 | PRRSV MLV on Day 46 | Necropsy on Day 50 |
|---|---|---|---|---|---|---|---|
| 1 | 15 | PVC2 Vaccine 1 16 µg rORF2-IMS 1314 | 0 & 14 | + | + | + | + |
| 2 | 15 | PVC2 Vaccine 2 16 µg vORF2-Carbopol | 0 & 14 | + | + | + | + |
| 3 | 15 | PCV2 Vaccine 3 16 µg rORF2-Carbopol | 0 & 14 | + | + | + | + |
| 4 | 15 | PCV2 Vaccine 2 16 µg vORF2-Carbopol | 0 | + | + | + | + |
| 5 | 15 | PVC2 Vaccine 3 4 µg rORF2-Carbopol | 0 & 14 | + | + | + | + |
| 6 | 15 | PVC2 Vaccine 3 1 µg rORF2-Carbopol | 0 & 14 | + | + | + | + |
| 7 | 15 | PVC2 Vaccine 3 0.25 µg rORF2-Carbopol | 0 & 14 | + | + | + | + |
| 8 | 15 | PVC2 Vaccine 4 >8.0 log KV-Carbopol | 0 & 14 | + | + | + | + |
| 9 | 15 | Challenge Controls | N/A | + | + | + | + |
| 10 | 15 | None-Strict Negative Control Group | N/A | + | − | + | + | vORF2 = isolated viral ORF2;
rORF2 = recombinant baculovirus expressed ORF2;
KV or killed whole cell virus = PCV2 virus grown in suitable cell culture The vaccine formulations given to each group were as follows. PCV2 Vaccine No. 1, administered at 1×2 ml dose to Group 1, was a high dose (16 µg/2 ml dose) of inactivated recombinant ORF2 antigen adjuvanted with IMS 1314 (16 µg rORF2—IMS1314). PCV2 Vaccine No. 2, administered at 1×2 ml dose to Group 2, was a high dose (16 µg/2 ml dose) of a partially purified VIDO R–1 generated PCV2 ORF2 antigen adjuvanted with Carbopol (16 µg vORF2—Carbopol). PCV2 Vaccine No. 3, administered at 1×2 ml dose to Group 3, was a high dose (16 µg/2 ml dose) of inactivated recombinant ORF2 antigen adjuvanted with Carbopol (16 µg rORF2—Carbopol). PCV2 Vaccine No. 4, administered at 1×1 ml dose to Group 4, was a high dose (16 µg/1 ml dose) of a partially purified VIDO R–1 generated PCV2 ORF2 antigen adjuvanted with Carbopol (16 µg vORF2—Carbopol). Vaccine No. 5, administered at 1×2 ml dose to Group 5, was a 4 µg/2 ml dose of an inactivated recombinant ORF2 antigen adjuvanted with Carbopol (4 µg rORF2—Carbopol). PCV2 Vaccine No. 6, administered at 1×2 ml dose to Group 6, was a 1 µg/2 ml dose of an inactivated recombinant ORF2 antigen adjuvanted with Carbopol (1 µg rORF2—Carbopol). PCV2 Vaccine No. 7, administered at 1×2 ml dose to Group 7, was a low dose (0.25 µg/2 ml dose) of inactivated recombinant ORF2 antigen adjuvanted with Carbopol (0.25 µg rORF2—Carbopol). PCV2 Vaccine No. 8, administered at 1×2 ml dose to Group 8, was a high dose (pre-inactivation titer >8.0 log/2 ml dose) Inactivated Conventional Killed VIDO R–1 generated PCV2 Struve antigen adjuvanted with Carbopol (>8.0 log KV—Carbopol). On Day 0, Groups 1-8 were treated with their assigned vaccines. Groups 1-3 and 5-8 received boosters of their respective vaccines again on Day 14. The effectiveness of a single dose of 16 µg of vORF2—Carbopol was tested on Group 4 which did not receive a booster on Day 14. Piglets were observed for adverse events and injection site reactions following both vaccinations. On Day 21 the piglets were moved to a second study site where Groups 1-9 were group housed in one building and Group 10 was housed in a separate building. All pigs received keyhole limpet hemocyanin emulsified with incomplete Freund's adjuvant (KLH/ICFA) on Days 22 and 28. On Day 25, Groups 1-9 were challenged with approximately 4 logs of virulent PCV2 virus. By Day 46, very few deaths had occurred in the challenge control group. In an attempt to immunostimulate the pigs and increase the virulence of the PCV2 challenge material, all Groups were treated with INGELVAC® PRRSV MLV (Porcine Reproductive and Respiratory Vaccine, Modified Live Virus) on Day 46. Pre- and post-challenge blood samples were collected for PCV2 serology. Post-challenge, body weight data for determination of average daily weight gain (ADWG) and observations of clinical signs were collected. On Day 50, all surviving pigs were necropsied, gross lesions were recorded, lungs were scored for pathology, and selected tissues were preserved in formalin for examination by Immunohistochemistry (IHC) for detection of PCV2 antigen at a later date.

Materials and Methods

This was a partially-blind vaccination-challenge feasibility study conducted in CDCD pigs, 6 to 16 days of age on Day 0. To be included in the study, PCV2 IFA titers of sows were ≤1:1000. Additionally, the serologic status of sows were from a known PRRS-negative herd. Sixteen (16) sows were tested for PCV2 serological status and all sixteen (16) had a PCV2 titer of ≤1000 and were transferred to the first study site. One hundred fifty (150) piglets were delivered by cesarean section surgeries and were available for this study on Day −3. On Day −3, 150 CDCD pigs at the first study site were weighed, identified with ear tags, blocked by weight and randomly assigned to 1 of 10 groups, as set forth above in table 16. Blood samples were collected from all pigs. If any test animal meeting the inclusion criteria was enrolled in the study and was later excluded for any reason, the Investigator and Monitor consulted in order to determine the use of data collected from the animal in the final analysis. The date of which enrolled piglets were excluded and the reason for exclusion was documented. No sows meeting the inclusion criteria, selected for the study and transported to the first study site were excluded. No piglets were excluded from the study, and no test animals were removed from the study prior to termination. Table 17 describes the time frames for the key activities of this Example.

TABLE 17

Study Activities

| Study Day | Actual Dates | Study Activity |
| --- | --- | --- |
| −3 | Apr. 4, 2003 | Weighed pigs; health exam; randomized to groups; collected blood samples |
| −3, 0-21 | Apr. 4, 2003 Apr. 7, 2003 to May 27, 2003 | Observed for overall health and for adverse events post-vaccination |
| 0 | Apr. 7, 2003 | Administered respective IVPs to Groups 1-8 |
| 0-7 | Apr. 7, 2003 to Apr. 14, 2003 | Observed pigs for injection site reactions |
| 14 | Apr. 21, 2003 | Boostered Groups 1-3, 5-8 with respective IVPs; blood sampled all pigs |
| 14-21 | Apr. 21, 2003 to Apr. 28, 2003 | Observed pigs for injection reactions |
| 19-21 | Apr. 26, 2003 to Apr. 28, 2003 | Treated all pigs with antibiotics |
| 21 | Apr. 28, 2003 | Pigs transported from Struve Labs, Inc. to Veterinary Resources, Inc.(VRI) |
| 22-50 | Apr. 28, 2003 to May 27, 2003 | Observed pigs for clinical signs post-challenge |
| 22 | Apr. 29, 2003 | Treated Groups 1-10 with KLH/ICFA |
| 25 | May 2, 2003 | Collected blood samples from all pigs; weighed all pigs; challenged Groups 1-9 with PCV2 challenge material |
| 28 | May 5, 2003 | Treated Groups 1-10 with KLH/ICFA |

TABLE 17-continued

Study Activities

| Study Day | Actual Dates | Study Activity |
| --- | --- | --- |
| 32 | May 9, 2003 | Collected blood samples from all pigs |
| 46 | May 23, 2003 | Administered INGELVAC ® PRRS MLV to all groups |
| 50 | May 27, 2003 | Collected blood samples, weighed and necropsied all pigs; gross lesions were recorded; lungs were evaluated for lesions; fresh and formalin fixed tissue samples were saved; In-life phase of the study was completed |

Following completion of the in-life phase of the study, formalin fixed tissues were examined by Immunohistochemistry (IHC) for detection of PCV2 antigen by a pathologist, blood samples were evaluated for PCV2 serology, and average daily weight gain (ADWG) was determined from Day 25 to Day 50.

Animals were housed at the first study site in individual cages in seven rooms from birth to approximately 11 days of age (approximately Day 0 of the study). Each room was identical in layout and consisted of stacked individual stainless steel cages with heated and filtered air supplied separately to each isolation unit. Each room had separate heat and ventilation, thereby preventing cross-contamination of air between rooms. Animals were housed in two different buildings at the second study site. Group 10 (The Strict negative control group) was housed separately in a converted nursery building and Groups 1-9 were housed in a converted farrowing building. Each group was housed in a separate pen (14-15 pigs per pen) and each pen provided approximately 2.3 square feet per pig. Groups 2, 4 and 8 were penned in three adjacent pens on one side of the alleyway and Groups 1, 3, 5, 6, 7, and 9 were penned in six adjacent pens on the other side of the alleyway. The Group separation was due to concern by the Study Monitor that vaccines administered to Groups 2, 4, and 8 had not been fully inactivated. Each pen was on an elevated deck with plastic slatted floors. A pit below the pens served as a holding tank for excrement and waste. Each building had its own separate heating and ventilation systems, with little likelihood of cross-contamination of air between buildings.

At the first study site, piglets were fed a specially formulated milk ration from birth to approximately 3 weeks of age. All piglets were consuming solid, special mixed ration by Day 21 (approximately 4½ weeks of age). At the second study site, all piglets were fed a custom non-medicated commercial mix ration appropriate for their age and weight, ad libitum. Water at both study sites was also available ad libitum.

All test pigs were treated with 1.0 mL of NAXCEL®, IM, in alternating hams on Days 19, 20, and 21. In addition, Pig No. 11 (Group 1) was treated with 0.5 mL of NAXCEL® IM on Day 10, Pig No. 13 (Group 10) was treated with 1 mL of Penicillin and 1 mL of PREDEF® 2x on Day 10, Pig No. 4 (Group 9) was treated with 1.0 mL of NAXCEL® IM on Day 11, and Pigs 1 (Group 1), 4 and 11 were each treated with 1.0 mL of NAXCEL® on Day 14 for various health reasons.

While at both study sites, pigs were under veterinary care Animal health examinations were conducted on Day −3 and were recorded on the Health Examination Record Form. All animals were in good health and nutritional status before vaccination as determined by observation on Day 0. All test animals were observed to be in good health and nutritional status prior to challenge. Carcasses and tissues were disposed of by rendering. Final disposition of study animals was recorded on the Animal Disposition Record.

On Days 0 and 14, pigs assigned to Groups 1-3 and 5-8 received 2.0 mL of assigned PCV2 Vaccines 1-4, respectively, IM in the right and left neck region, respectively, using a sterile 3.0 mL Luer-lock syringe and a sterile 20 g×½" needle. Pigs assigned to Group 4 received 1.0 mL of PCV2 Vaccine No. 2, IM in the right neck region using a sterile 3.0 mL Luer-lock syringe and a sterile 20 g×½" needle on Day 0 only.

On Day 22 all test pigs received 2.0 mL of KLH/ICFA IM in the left neck region using a sterile 3.0 mL Luer-lock syringe and a sterile 20 g×1" needle. On Day 28 all test pigs received 2.0 mL of KLH/ICFA in the right ham region using a sterile 3.0 mL Luer-lock syringe and a sterile 20 g×1" needle.

On Day 25, pigs assigned to Groups 1-9 received 1.0 mL of PCV2 ISUVDL challenge material (3.98 $\log_{10}$ $TCID_{50}$/mL) IM in the right neck region using a sterile 3.0 mL Luer-lock syringe and a sterile 20 g×1" needle. An additional 1.0 mL of the same material was administered IN to each pig (0.5 mL per nostril) using a sterile 3.0 mL Luer-lock syringe and nasal canula.

On Day 46, all test pigs received 2.0 mL INGELVAC® PRRS MLV, IM, in the right neck region using a sterile 3.0 mL Luer0lock syringe and a sterile 20 g×1" needle. The PRRSV MLV was administered in an attempt to increase virulence of the PCV2 challenge material.

Test pigs were observed daily for overall health and adverse events on Day −3 and from Day 0 to Day 21. Each of the pigs were scored for normal or abnormal behavior, respiration, or cough. Observations were recorded on the Clinical Observation Record. All test pigs were observed from Day 0 to Day 7, and Group 7 was further observed from Day 14 to 21, for injection site reactions. Average daily weight gain was determined by weighing each pig on a calibrated scale on Days −3, 25 and 50, or on the day that a pig was found dead after challenge. Body weights were recorded on the Body Weight Form. Day −3 body weights were utilized to block pigs prior to randomization. Day 25 and Day 50 weight data was utilized to determine the average daily weight gain (ADWG) for each pig during these time points. For pigs that died after challenge and before Day 50, the ADWG was adjusted to represent the ADWG from Day 25 to the day of death.

In order to determine PCV2 serology, venous whole blood was collected from each piglet from the orbital venous sinus on Days −3 and 14. For each piglet, blood was collected from the orbital venous sinus by inserting a sterile capillary tube into the medial canthus of one of the eyes and draining approximately 3.0 mL of whole blood into a 4.0 mL Serum Separator Tube (SST). On Days 25, 32, and 50, venous whole blood from each pig was collected from the anterior vena cava using a sterile 20 g×1½" Vacutainer® needle (Becton Dickinson and Company, Franklin Lakes, N.J.), a Vaccutainer® needle holder and a 13 mL SST. Blood collections at each time point were recorded on the Sample Collection Record. Blood in each SST was allowed to clot, each SST was then spun down and the serum harvested. Harvested serum was transferred to a sterile snap tube and stored at −70±10° C. until tested at a later date. Serum samples were tested for the presence of PCV2 antibodies by BIVI-R&D personnel.

Pigs were observed once daily from Day 22 to Day 50 for clinical symptoms and scored for normal or abnormal behavior, respiration or cough. Clinical observations were recorded on the Clinical Observation Record.

Pigs Nos. 46 (Group 1) and 98 (Groups 9) died at the first study site. Both of these deaths were categorized as bleeding deaths and necropsies were not conducted on these two pigs. At the second study site, pigs that died after challenge and prior to Day 50, and pigs euthanized on Day 50, were necropsied. Any gross lesions were noted and the percentages of lung lobes with lesions were recorded on the Necropsy Report Form.

From each of the pigs necropsied at the second study site, a tissue sample of tonsil, lung, heart, and mesenteric lymph node was placed into a single container with buffered 10% formalin; while another tissue sample from the same aforementioned organs was placed into a Whirl-Pak® (M-Tech Diagnostics Ltd., Thelwall, UK) and each Whirl-Pak® was placed on ice. Each container was properly labeled. Sample collections were recorded on the Necropsy Report Form. Afterwards, formalin-fixed tissue samples and a Diagnostic Request Form were submitted for IHC testing. IHC testing was conducted in accordance with standard laboratory procedures for receiving samples, sample and slide preparation, and staining techniques. Fresh tissues in Whirl-Paks® were shipped with ice packs to the Study Monitor for storage (−70°±10° C.) and possible future use.

Formalin-fixed tissues were examined by a pathologist for detection of PCV2 by IHC and scored using the following scoring system: 0=None; 1=Scant positive staining, few sites; 2=Moderate positive staining, multiple sites; and 3=Abundant positive staining, diffuse throughout the tissue. For analytical purposes, a score of 0 was considered "negative," and a score of greater than 0 was considered "positive."

Results

Results for this example are given below. It is noted that Pigs No. 46 and 98 died on days 14 and 25 respectively. These deaths were categorized as bleeding deaths. Pig No. 11 (Group 1) was panting with rapid respiration on Day 15. Otherwise, all pigs were normal for behavior, respiration and cough during this observation period and no systemic adverse events were noted with any groups. No injection site reactions were noted following vaccination on Day 0. Following vaccination on Day 14, seven (7) out of fourteen (14) Group 1 pigs (50.0%) had swelling with a score of "2" on Day 15. Four (4) out of fourteen (14) Group 1 (28.6%) still had a swelling of "2" on Day 16. None of the other groups experienced injection site reactions following either vaccination.

Average daily weight gain (ADWG) results are presented below in Table 18. Pig Nos. 46 and 98 that died from bleeding were excluded from group results. Group 4, which received one dose of 16 µg vORF2—Carbopol, had the highest ADWG (1.16±0.26 lbs/day), followed by Groups 1, 2, 3, 5, 6, and 10 which had ADWGs that ranged from 1.07±0.23 lbs/day to 1.11±0.26 lbs/day. Group 9 had the lowest ADWG (0.88±0.29 lbs/day), followed by Groups 8 and 7, which had ADWGs of 0.93±0.33 lbs/day and 0.99±0.44 lbs/day, respectively.

TABLE 18

Summary of Group Average Daily Weight Gains (ADWG)

| Group | Treatment | N | ADWG - lbs/day (Day 25 to Day 50) or adjusted for pigs dead before Day 50 |
|---|---|---|---|
| 1 | rORF2 - 16 µg - IMS 1314 2 doses | 14 | 1.08 ± 0.30 lbs/day |
| 2 | vORF2 - 16 µg - Carbopol 2 doses | 15 | 1.11 ± 0.16 lbs/day |
| 3 | rORF2 - 16 µg - Carbopol 2 doses | 15 | 1.07 ± 0.21 lbs/day |
| 4 | vORF2 - 16 µg - Carbopol 1 dose | 15 | 1.16 ± 0.26 lbs/day |
| 5 | rORF2 - 4 µg - Carbopol 1 dose | 15 | 1.07 ± 0.26 lbs/day |
| 6 | rORF2 - 1 µg - Carbopol 2 doses | 15 | 1.11 ± 0.26 lbs/day |

TABLE 18-continued

Summary of Group Average Daily Weight Gains (ADWG)

| Group | Treatment | N | ADWG - lbs/day (Day 25 to Day 50) or adjusted for pigs dead before Day 50 |
|---|---|---|---|
| 7 | rORF2 - 0.25 µg - Carbopol 2 doses | 15 | 0.99 ± 0.44 lbs/day |
| 8 | KV > 8.0 µg - Carbopol 2 doses | 15 | 0.93 ± 0.33 lbs/day |
| 9 | Challenge Controls | 14 | 0.88 ± 0.29 lbs/day |
| 10 | Strict Negative Controls | 15 | 1.07 ± 0.23 lbs/day | vORF2 = isolated viral ORF2;
rORF2 = recombinant baculovirus expressed ORF2;
KV or killed whole cell virus = PCV2 virus grown in suitable cell culture PVC2 serology results are presented below in Table 19. All ten (10) groups were seronegative for PCV2 on Day −3. On Day 14, PCV2 titers remained low for all ten (10) groups (range of 50-113). On Day 25, Group 8, which received the whole cell killed virus vaccine, had the highest PCV2 titer (4617), followed by Group 2, which received 16 µg vORF2—Carbopol, Group 4, which received as single dose of 16 µg vORF2—Carbopol, and Group 3, which received 16 µg rORF2—Carbopol, which had titers of 2507, 1920 and 1503 respectively. On Day 32 (one week post challenge), titers for Groups 1-6 and Group 8 ranged from 2360 to 7619; while Groups 7 (0.25 µg rORF2—Carbopol), 9 (Challenge Control), and 10 (Strict negative control) had titers of 382, 129 and 78 respectively. On Day 50 (day of necropsy), all ten (10) groups demonstrated high PCV2 titers (≥1257).

On Days 25, 32, and 50, Group 3, which received two doses of 16 µg rORF2—Carbopol, had higher antibody titers than Group 1, which received two doses of 16 µg rORF2—IMS 1314. On Days 25, 32 and 50, Group 2, which received two doses of 16 µg vORF2, had higher titers than Group 4, which received only one does of the same vaccine. Groups 3, 5, 6, 7, which received decreasing levels of rORF2—Carbopol, of 16, 4, 1, and 0.25 µg respectively, demonstrated correspondingly decreasing antibody titers on Days 25 and 32.

TABLE 19

Summary of Group PCV2 IFA Titers

| Group | Treatment | Day -3 | Day 14** | Day 25*** | Day 32 | Day 50**** |
|---|---|---|---|---|---|---|
| 1 | rORF2-16 µg-IMS 1314 2 doses | 50 | 64 | 646 | 3326 | 4314 |
| 2 | vORF2-16 µg-Carbopol 2 doses | 50 | 110 | 2507 | 5627 | 4005 |
| 3 | rORF2-16 µg-Carbopol 2 doses | 50 | 80 | 1503 | 5120 | 6720 |
| 4 | vORF2-16 µg-Carbopol 1 dose | 50 | 113 | 1920 | 3720 | 1257 |
| 5 | rORF2-4 µg-Carbopol 1 dose | 50 | 61 | 1867 | 3933 | 4533 |
| 6 | rORF2-Carbopol 2 doses | 50 | 70 | 490 | 2360 | 5740 |
| 7 | rORF2-0.25 µg-Carbopol 2 doses | 50 | 73 | 63 | 382 | 5819 |
| 8 | KV > 8.0 log-Carbopol 2 doses | 50 | 97 | 4617 | 7619 | 10817 |
| 9 | Challenge Controls | 50 | 53 | 50 | 129 | 4288 |
| 10 | Strict Negative Controls | 50 | 50 | 50 | 78 | 11205 | vORF2 = isolated viral ORF2;
rORF2 = recombinant baculovirus expressed ORF2;
KV or killed whole cell virus = PCV2 virus grown in suitable cell culture
*For calculation purposes, a ≤100 IFA titer was designated as a titer of "50"; a ≥6400 IFA titer was designated as a titer of "12,800".
**Day of Challenge
***Day of Necropsy The results from the post-challenge clinical observations are presented below. Table 20 includes observations for Abnormal Behavior, Abnormal Respiration, Cough and Diarrhea. Table 21 includes the results from the Summary of Group Overall Incidence of Clinical Symptoms and Table 22 includes results from the Summary of Group Mortality Rates Post-challenge. The incidence of abnormal behavior, respiration and cough post-challenge were low in pigs receiving 16 µg rORF2—IMS 1314 (Group 1), 16 µg rORF2—Carbopol (Group 3), 1 µg rORF2—Carbopol (Group 6), 0.25 µg rORF2—Carbopol (Group 7), and in pigs in the Challenge Control Group (Group 9). The incidence of abnormal behavior, respiration, and cough post-challenge was zero in pigs receiving 16 µg vORF2—Carbopol (Group 2), a single dose of 16 µg vORF2—Carbopol (Group 4), 4 µg rORF2—Carbopol (Group 5), >8 log KV-Carbopol (Group 8), and in pigs in the strict negative control group (Group 10).

The overall incidence of clinical symptoms varied between groups. Pigs receiving 16 µg vORF2—Carbopol (Group 2), a single dose of 16 µg vORF2—Carbopol (Group 4), and pigs in the Strict negative control group (Group 10) had incidence rates of 0%; pigs receiving 16 µg rORF2—Carbopol (Group 3), and 1 µg rORF2—Carbopol (Group 6) had incidence rates of 6.7%; pigs receiving 16 µg rORF2—

IMS 1314 (Group 1) had an overall incidence rate of 7.1%; pigs receiving 4 µg rORF2—Carbopol (Group 5), 0.25 µg rORF2—Carbopol (Group 7), and >8 log KV vaccine had incidence rates of 13.3%; and pigs in the Challenge Control Group (Group 9) had an incidence rate of 14.3%.

Overall mortality rates between groups varied as well. Group 8, which received 2 doses of KV vaccine had the highest mortality rate of 20.0%; followed by Group 9, the challenge control group, and Group 7, which received 0.25 µg rORF2—Carbopol and had mortality rates of 14.3% and 13.3% respectively. Group 4, which received one dose of 16 µg vORF2—Carbopol had a 6.7% mortality rate. All of the other Groups, 1, 2, 3, 5, 6, and 10, had a 0% mortality rate.

TABLE 20

Summary of Group Observations for Abnormal Behavior, Abnormal Respiration, and Cough Post-Challenge

| Group | Treatment | N | Abnormal Behavior[1] | Abnormal Behavior[2] | Cough[3] |
|---|---|---|---|---|---|
| 1 | rORF2 - 16 µg - IMS 1314 2 doses | 14 | 0/14 (0%) | 0/14 (0%) | 1/14 (7.1%) |
| 2 | vORF2 - 16 µg - Carbopol 2 doses | 15 | 0/15 (0%) | 0/15 (0%) | 0/15 (0%) |
| 3 | rORF2 - 16 µg - Carbopol 2 doses | 15 | 0/15 (0%) | 0/15 (0%) | 1/15 (6.7%) |
| 4 | vORF2 - 16 µg - Carbopol 1 dose | 15 | 0/15 (0%) | 0/15 (0%) | 0/15 (0%) |
| 5 | rORF2 - 4 µg - Carbopol 1 dose | 15 | 1/15 (6.7%) | 1/15 (6.7%) | 0/15 (0%) |
| 6 | rORF2 - 1 µg - Carbopol 2 doses | 15 | 0/15 (0%) | 0/15 (0%) | 1/15 (6.7%) |
| 7 | rORF2 - 0.25 µg - Carbopol 2 doses | 15 | 0/15 (0%) | 1/15 (6.7%) | 1/15 (06.7%) |
| 8 | KV > 8.0 log - Carbopol 2 doses | 15 | 1/15 (6.7%) | 1/15 (6.7%) | 0/15 (0%) |
| 9 | Challenge Controls | 14 | 1/14 (7.1%) | 1/14 (7.1%) | 2/14 (14.3%) |
| 10 | Strict Negative Controls | 15 | 0/15 (0%) | 0/15 (0%) | 0/15 (0%) |

[1]Total number of pigs in each group that demonstrated any abnormal behavior for at least one day
[2]Total number of pigs in each group that demonstrated any abnormal respiration for at least one day
[3]Total number of pigs in each group that demonstrated a cough for at least one day

TABLE 21

Summary of Group Overall Incidence of Clinical Symptoms Post-Challenge

| Group | Treatment | N | Incidence of pigs with Clinical Symptoms[1] | Incidence Rate |
|---|---|---|---|---|
| 1 | rORF2 - 16 µg - IMS 1314 2 doses | 14 | 1 | 7.1% |
| 2 | vORF2 - 16 µg - Carbopol 2 doses | 15 | 0 | 0.0% |
| 3 | rORF2 - 16 µg - Carbopol 2 doses | 15 | 1 | 6.7% |
| 4 | vORF2 - 16 µg - Carbopol 1 dose | 15 | 0 | 0.0% |
| 5 | rORF2 - 4 µg - Carbopol 1 dose | 15 | 2 | 13.3% |
| 6 | rORF2 - 1 µg - Carbopol 2 doses | 15 | 1 | 6.7% |
| 7 | rORF2 - 0.25 µg - Carbopol 2 doses | 15 | 2 | 13.3% |
| 8 | KV > 8.0 log - Carbopol 2 doses | 15 | 2 | 13.3% |
| 9 | Challenge Controls | 14 | 2 | 14.3% |
| 10 | Strict Negative Controls | 15 | 0 | 0.0% | vORF2 = isolated viral ORF2;
rORF2 = recombinant baculovirus expressed ORF2;
KV or killed whole cell virus = PCV2 virus grown in suitable cell culture
[1]Total number of pigs in each group that demonstrated any clinical symptom for at least one day

TABLE 22

Summary of Group Mortality Rates Post-Challenge

| Group | Treatment | N | Dead Post-challenge | Mortality Rate |
|---|---|---|---|---|
| 1 | rORF2 - 16 µg - IMS 1314 2 doses | 14 | 0 | 0.0% |
| 2 | vORF2 - 16 µg - Carbopol 2 doses | 15 | 0 | 0.0% |
| 3 | rORF2 - 16 µg - Carbopol 2 doses | 15 | 0 | 0.0% |
| 4 | vORF2 - 16 µg - Carbopol 1 dose | 15 | 1 | 6.7% |
| 5 | rORF2 - 4 µg - Carbopol 1 dose | 15 | 0 | 0.0% |
| 6 | rORF2 - 1 µg - Carbopol 2 doses | 15 | 0 | 0.0% |
| 7 | rORF2 - 0.25 µg - Carbopol 2 doses | 15 | 2 | 13.3% |
| 8 | KV > 8.0 log - Carbopol 2 doses | 15 | 3 | 20.0% |
| 9 | Challenge Controls | 14 | 2 | 14.3% |
| 10 | Strict Negative Controls | 15 | 0 | 0.0% | vORF2 = isolated viral ORF2;
rORF2 = recombinant baculovirus expressed ORF2;
KV or killed whole cell virus = PCV2 virus grown in suitable cell culture The Summary of Group Mean Percentage Lung Lesions and Tentative Diagnosis is given below in Table 23. Group 9, the challenge control group, had the highest percentage lung lesions with a mean of 10.81±23.27%, followed by Group 7, which received 0.25 µg rORF2—Carbopol and had a mean of 6.57±24.74%, Group 5, which received 4 µg rORF2—Carbopol and had a mean of 2.88±8.88%, and Group 8, which received the KV vaccine and had a mean of 2.01±4.98%. The remaining six (6) groups had lower mean percentage lung lesions that ranged from 0.11±0.38% to 0.90±0.15%.

Tentative diagnosis of pneumonia varied among the groups. Group 3, which received two doses of 16 µg rORF2—Carbopol, had the lowest tentative diagnosis of pneumonia, with 13.3%. Group 9, the challenge control group, had 50% of the group tentatively diagnosed with pneumonia, followed by Group 10, the strict negative control group and Group 2, which received two doses of 16 µg vORF2—Carbopol, with 46.7% and 40% respectively, tentatively diagnosed with pneumonia.

Groups 1, 2, 3, 5, 9, and 10 had 0% of the group tentatively diagnosed as PCV2 infected; while Group 8, which received two doses if KV vaccine, had the highest group rate of tentative diagnosis of PCV2 infection, with 20%. Group 7, which received two doses of 0.25 µg rORF2—Carbopol, and Group 4, which received one dose of 16 µg vORF2—Carbopol had tentative group diagnoses of PCV2 infection in 13.3% and 6.7% of each group, respectively.

Gastric ulcers were only diagnosed in one pig in Group 7 (6.7%); while the other 9 groups remained free of gastric ulcers.

TABLE 23

Summary of Group Mean % Lung Lesion and Tentative Diagnosis

| Group | Treatment | N | No. Of pigs that shed for at least one day | Incidence Rate |
|---|---|---|---|---|
| 1 | rORF2 - 16 µg - IMS 1314 2 doses | 15 | 0 | 0% |
| 2 | vORF2 - 16 µg - Carbopol 2 doses | 15 | 1 | 6.7% |
| 3 | rORF2 - 16 µg - Carbopol 2 doses | 15 | 3 | 20.0% |
| 4 | vORF2 - 16 µg - Carbopol 1 dose | 15 | 2 | 13.3% |
| 5 | rORF2 - 4 µg - Carbopol 1 dose | 15 | 3 | 20.0% |
| 6 | rORF2 - 1 µg - Carbopol 2 doses | 15 | 6 | 40.0% |
| 7 | rORF2 - 0.25 µg - Carbopol 2 doses | 15 | 7 | 46.7% |
| 8 | KV > 8.0 log - Carbopol 2 doses | 15 | 12 | 80% |
| 9 | Challenge Controls | 14 | 14 | 100.0% |
| 10 | Strict Negative Controls | 15

One of the hallmarks of late stage PCV2 infection and subsequent PMWS development is growth retardation in weaned pigs, and in severe cases, weight loss is noted. Average daily weight gain of groups is a quantitative method of demonstrating growth retardation or weight loss. In this example, there was not a large difference in ADWG between groups. Group 8 had the lowest ADWG of 0.88±0.29 lbs/day, while Group 4 had the highest ADWG of 1.16±0.26 lb/day. Within the context of this study there was not a sufficient difference between groups to base future vaccine efficacy on ADWG.

In addition to weight loss—dyspnea, leghargy, pallor of the skin and sometimes icterus are clinical symptoms associated with PMWS. In this example, abnormal behavior and abnormal respiration and cough were noted infrequently for each group. As evidenced in this study, this challenge model and challenge strain do not result in overwhelming clinical symptoms and this is not a strong parameter on which to base vaccine efficacy.

Overall, mortality rates were not high in this example and the lack of a high mortality rate in the challenge control group limits this parameter on which to base vaccine efficacy. Prior to Day 46, Groups 4 and 7 each had one out of fifteen pigs die, Group 9 had two out of fourteen pigs die and Group 8 had three out of fifteen pigs die. Due to the fact that Group 9, the challenge control group was not demonstrating PCV2 clinical symptoms and only two deaths had occurred in this group by Day 46, Porcine Respiratory and Reproductive Syndrome Virus (PRRSV) MLV vaccine was administered to all pigs on Day 46. Earlier studies had utilized INGELVAC® PRRS MLV as an immunostimulant to exasperate PCV2-associated PMWS disease and mortality rates were higher in these earlier studies. Two deaths occurred shortly after administering the PRRS vaccine on Day 46—Group 4 had one death on Day 46 and Group 7 had one death on Day 47—which were probably not associated with the administration of the PRRS vaccine. By Day 50, Group 8, which received two doses of killed vaccine, had the highest mortality rate (20%), followed by Group 9 (challenge control) and Group 7 (0.25 µg rORF2—Carbopol), with mortality rates of 14.3% and 13.3% respectively. Overall, administration of the PRRS vaccine to the challenge model late in the post-challenge observation phase of this example did not significantly increase mortality rates.

Gross lesions in pigs with PMWS secondary to PCV2 infection typically consist of generalized lymphadenopathy in combination with one or more of the following: (1) interstitial pneumonia with interlobular edema, (2) cutaneous pallor or icterus, (3) mottled atrophic livers, (4) gastric ulcers, (5) nephritis and (6) reproductive disorders, e.g. abortion, stillbirths, mummies, etc. At necropsy (Day 50), icterus, hepatitis, and nephritis were not noted in any groups. A gastric ulcer was noted in one Group 7 pig, but lymphadenopathy was not specifically examined for. Based on the presence of lesions that were consistent with PCV2 infection, three groups had at least one pig tentatively diagnosed with PCV2 (PMWS). Group 8, which received two doses of killed vaccine, had 20% tentatively diagnosed with PCV2, while Group 7 and Group 4 had 13.3% and 6.7%, respectively, tentatively diagnosed with PCV2. The mean % lung lesion scores varied between groups at necropsy. Groups 1, 2, 3, 4, 6 and 10 had low % lung lesion scores that ranged from 0.11±0.38% to 0.90±0.15%. As expected, Group 9, the challenge control group, had the highest mean % lung lesion score (10.81±23.27%). In four groups, the mean % lung lesion scores were elevated due to one to three pigs in each of these groups having very high lung lesion scores. The lung lesions were red/purple and consolidated. Typically, lung lesions associated with PMWS are described as tan, non-collapsible, and with interlobular edema. The lung lesions noted in this study were either not associated with PCV2 infection or a second pulmonary infectious agent may have been present. Within the context of this study, the % lung lesion scores probably do no reflect a true measure of the amount of lung infection due to PCV2. Likewise, tentative diagnosis of pneumonia may have been over-utilized as well. Any pigs with lung lesions, some as small as 0.10% were listed with a tentative diagnosis of pneumonia. In this example, there was no sufficient difference between groups with respect to gross lesions and % lung lesions on which to base vaccine efficacy.

IHC results showed the largest differences between groups. Group 1 (16 µg rORF2—IMS 1314) had the lowest positive IHC results for PCV2 antigen (0%); while Groups 9 and 10 had the highest positive IHC results with incidence rates of 100% and 93.3% respectively. Groups 3, 5, 6 and 7, which received 16, 4, 1 or 0.25 µg of rORF2 antigen, respectively, adjuvanted with Carbopol, had IHC positive rates of 20%, 20%, 40% and 46.7%, respectively. Group 2, which received two doses of 16 µg vORF2 adjuvanted with Carbopol had an IHC positive rate of 6.7%, while Group 4 which received only one dose of the same vaccine, had an IHC positive rate of 13.3%. Due to the objective nature of this test and the fact that IHC results correlated with expected results, IHC testing is probably one of the best parameters on which to base vaccine efficacy.

Thus in one aspect of the present invention, the Minimum Protective Dosage (MPD) of PCV2 rORF2 antigen adjuvanted with Carbopol in the CDCD pig model in the face of a PCV2 challenge is determined Groups 3, 5, 6 and 7 each received two doses of rORF2 antigen adjuvanted with Carbopol, but the level of rORF2 antigen varied for each group. Groups 3, 5, 6 and 7 each received 16, 4, 1 or 0.25 µg of rORF2 antigen respectively. In general, decreasing the level of rORF2 antigen decreased PCV2 antibody titers, and increased the mortality rate, mean % lung lesions, and the incidence of IHC positive tissues. Of the four groups receiving varying levels of rORF2—Carbopol, Groups 3 and 5, which received two doses of 16 or 4 µg of rORF2 antigen, respectively, each had an IHC positive rate of only 20%, and each had similar antibody titers. Overall, based on IHC positive results, the minimum protective dosage of rORF2 antigen administered twice is approximately 4 µg.

In another aspect of the present invention, the antigenicity of recombinant (rORF2) and VIDO R–1 (vORF2) PCV2 antigens were assessed. Group 2 received two doses of 16 µg vORF2 and Group 3 received two doses of 16 µg rORF2. Both vaccines were adjuvanted with Carbopol. Both vaccines were found to be safe and both had 0% mortality rate. Group 2 had a PCV2 antibody titer of 2507 on Day 25, while Group 3 had a PCV2 antibody titer of 1503. Group 3 had a lower mean % lung lesion score than Group 2 (0.11±0.38% vs. 0.90±0.15%), but Group 2 had a lower IHC positive incidence rate that Group 3 (6.7% vs. 20%). Overall, both vaccines had similar antigenicity, but vORF2 was associated with slightly better IHC results.

In yet another aspect of the present invention, the suitability of two different adjuvants (Carbopol and IMS 1314) was determined Groups 1 and 3 both received two doses of vaccine containing 16 µg of rORF2 antigen, but Group 1 received the antigen adjuvanted with IMS 1314 while Group 3 received the antigen adjuvanted with Carbopol. Both groups had essentially the same ADWG, essentially the same incidence of clinical signs post-challenge, the same mortality rate, and essentially the same mean % lung lesions; but Group 1 had an IHC positive rate of 0% while Group 3 had an IHC positive rate of 20%. However, Group 3, which received the vaccine adjuvanted with Carbopol, had higher IFAT PCV2 titers on Days 25, 32, and 50 than Group 1, which received the vaccine adjuvanted with IMS 1314. Overall, although the PCV2 vaccine adjuvanted with IMS 1314 did provide better IHC results, it did not provide overwhelmingly better protection from PCV2 infection and did induce injection site reaction. Whereas the PCV2 vaccine adjuvanted with Carbopol performed nearly as well as the IMS 1314 adjuvanted vaccine, but was not associated with any adverse events.

In still another aspect of the present invention, the feasibility of PCV2 ORF2 as a 1 ml, 1 dose product was determined Groups 2 and 4 both received 16 µg of vORF2 vaccine adjuvanted with Carbopol on Day 0, but Group 2 received a second dose on Day 14. Group 4 had a slightly higher ADWG and a lower mean % lung lesions than Group 2, but Group 2 had higher IFAT PCV2 titers on Day 25, 32 and 50, and a slightly lower incidence rate of IHC positive tissues. All other results for these two groups were similar. Overall, one dose of vORF2 adjuvanted with Carbopol performed similar to two doses of the same vaccine.

We claim:

1. A method for aiding in the prevention or reduction of one or more of clinical symptoms associated with porcine circovirus type 2 (PCV2) infection, wherein the clinical symptoms are selected from the group consisting of PCV2 virus shedding, lymphoid infection caused by PCV2, increased mortality rate, decreased average daily weight gain, overall porcine circovirus load, and any combination thereof in pigs, said method comprising administering a single dose of a recombinantly produced PCV2 ORF2 protein to a pig less than 15 weeks of age.

2. The method of claim 1, wherein said PCV2 ORF2 protein is selected from the group consisting of:

a. a polypeptide comprising a sequence selected from the group consisting of SEQ ID NO: 5, SEQ ID NO: 6, SEQ ID NO: 9, SEQ ID NO: 10, and SEQ ID NO: 11;
   b. any polypeptide that is at least 90% homologous to the polypeptide of a);
   c. a polypeptide that is encoded by a polynucleotide comprising the sequence of SEQ ID NO: 3 or SEQ ID NO: 4; or
   d. any polypeptide that is encoded by a polynucleotide that is at least 90% homologous to the polynucleotide of c).

3. The method of claim 1, wherein said PCV2 ORF2 protein is a baculovirus expressed PCV2 ORF2 protein.

4. The method of claim 1, wherein said PCV2 ORF2 protein is formulated and administered in one (1) mL per dose.

5. The method of claim 1, wherein said administering of the single dose occurs in pigs 3 weeks of age or older.

6. The method of claim 1, wherein said administering of the single dose occurs within about 3 weeks of exposure to a virulent porcine circovirus type 2 antigen.

7. The method of claim 1, wherein said composition further comprises at least one additional component selected from the group consisting of veterinary-acceptable carriers, pharmaceutical-acceptable carriers, adjuvants, cell culture supernatant, and immunomodulatory agents.

8. The method of claim 1, wherein said administering is performed using a method selected from the group consisting of intradermal, intratracheal, intravaginal, intramuscular, intranasal, intravenous, intravascular, intraarterial, intraperitoneal, oral, intrathecal, subcutaneous, intracutaneous, intracardial, intralobal, intramedullar, or intrapulmonar.

9. The method of claim 1, wherein the administering of said PCV2 ORF2 protein does not show adverse events or injection site reactions.

10. A recombinantly produced porcine circovirus type 2 (PCV2) ORF2 protein for use in the preparation of a medicament for aiding in the prevention or reduction of one or more of clinical symptoms associated with PCV2 infection, wherein the clinical symptoms are selected from the group consisting of PCV2 virus shedding, lymphoid infection caused by PCV2, increased mortality rate, decreased average daily weight gain, overall porcine circovirus load, and any combination thereof in pigs, wherein said medicament is administered as a single dose to a pig less than 15 weeks of age.

11. The recombinantly produced porcine circovirus type 2 (PCV2) ORF2 protein for use according to claim 10, wherein said PCV2 ORF2 protein is selected from the group consisting of:
   a. a polypeptide comprising a sequence selected from the group consisting of SEQ ID NO: 5, SEQ ID NO: 6, SEQ ID NO: 9, SEQ ID NO: 10, and SEQ ID NO: 11;
   b. any polypeptide that is at least 90% homologous to the polypeptide of a);
   c. a polypeptide that is encoded by a polynucleotide comprising the sequence of SEQ ID NO: 3 or SEQ ID NO: 4; or
   d. any polypeptide that is encoded by a polynucleotide that is at least 90% homologous to the polynucleotide of c).

12. The recombinantly produced porcine circovirus type 2 (PCV2) ORF2 protein for use according to claim 10, wherein said PCV2 ORF2 protein is baculovirus expressed PCV2 ORF2 protein.

13. The recombinantly produced porcine circovirus type 2 (PCV2) ORF2 protein for use according to claim 10, wherein said PCV2 ORF2 protein is formulated and administered in one (1) mL per dose.

14. The recombinantly produced porcine circovirus type 2 (PCV2) ORF2 protein for use according to claim 10, wherein said administration occurs in pigs not older than 3 weeks of age, preferably not older than 2 weeks of age.

15. The recombinantly produced porcine circovirus type 2 (PCV2) ORF2 protein for use according to claim 10, wherein said administration is within about 3 weeks of age or older and/or within about 3 weeks of exposure to a virulent porcine circovirus type 2 antigen.

16. The recombinantly produced porcine circovirus type 2 (PCV2) ORF2 protein for use according to claim 10, wherein said medicament further comprises at least one additional component selected from the group consisting of veterinary-acceptable carriers, pharmaceutical-acceptable carriers, adjuvants, cell culture supernatant, and immunomodulatory agents.

17. The recombinantly produced porcine circovirus type 2 (PCV2) ORF2 protein for use according to claim 10, wherein said administration is intradermal, intratracheal, intravaginal, intramuscular, intranasal, intravenous, intravascular, intraarterial, intraperitoneal, oral, intrathecal, subcutaneous, intracutaneous, intracardial, intralobal, intramedullar, or intrapulmonar.

18. The recombinantly produced porcine circovirus type 2 (PCV2) ORF2 protein for use according to claim 10, wherein the administration of said PCV2 ORF2 protein does not show adverse events or injection site reactions.

19. The method of claim 1, wherein said one or more clinical symptoms associated with PCV2 infection is PCV2 virus shedding.

20. The method of claim 1, wherein said one or more clinical symptoms associated with PCV2 infection is lymphoid infection caused by PCV2.

21. The method of claim 1, wherein said one or more clinical symptoms associated with PCV2 infection is increased mortality rate.

22. The method of claim 1, wherein said one or more clinical symptoms associated with PCV2 infection is decreased average daily weight gain.

23. The method of claim 1, wherein said one or more clinical symptoms associated with PCV2 infection is the overall porcine circovirus load as determined by PCV2 viremia.

24. The recombinantly produced porcine circovirus type 2 (PCV2) ORF2 protein of claim 10, wherein said one or more clinical symptoms associated with PCV2 infection is PCV2 virus shedding.

25. The recombinantly produced porcine circovirus type 2 (PCV2) ORF2 protein of claim 10, wherein said one or more clinical symptoms associated with PCV2 infection is lymphoid infection caused by PCV2.

26. The recombinantly produced porcine circovirus type 2 (PCV2) ORF2 protein of claim 10, wherein said one or more clinical symptoms associated with PCV2 infection is increased mortality rate.

27. The recombinantly produced porcine circovirus type 2 (PCV2) ORF2 protein of claim 10, wherein said one or more clinical symptoms associated with PCV2 infection is decreased average daily weight gain.

28. The recombinantly produced porcine circovirus type 2 (PCV2) ORF2 protein of claim 10, wherein said one or more clinical symptoms associated with PCV2 infection is the overall porcine circovirus load as determined by PCV2 viremia.

29. The method according to claim 7, wherein said adjuvant can include aluminum hydroxide and aluminum phosphate, saponins, water-in-oil emulsions, oil-in-water emulsion, water-in-oil-water emulsion, or wherein the adjuvant is a compound chosen from the polymers of acrylic or methacrylic acid and the copolymers of maleic anhydride and alkenyl derivative.

30. The method according to claim 29, wherein said adjuvant is included at a concentration of 100 µg to 10 mg per dose.

31. The method according to claim 16, wherein said adjuvant can include aluminum hydroxide and aluminum phosphate, saponins, water-in-oil emulsions, oil-in-water emulsion, water-in-oil-water emulsion, or wherein the adjuvant is a compound chosen from the polymers of acrylic or methacrylic acid and the copolymers of maleic anhydride and alkenyl derivative.

32. The method according to claim 31, wherein said adjuvant is included at a concentration of 100 µg to 10 mg per dose.

33. A method for the vaccination of pigs against PCV2 infection comprising the step of administering a single dose of an immunogenic composition comprising a PCV2 ORF2 protein and a pharmaceutical-acceptable carrier to a pig less than 15 weeks of age, and wherein the single dose induces an immune response against PCV2 in the pig.

34. The method of claim 33, wherein the method reduces one or more clinical symptoms of PCV2 infection in pigs, wherein the clinical symptoms are selected from the group consisting of PCV2 virus shedding, lymphoid infection caused by PCV2, increased mortality rate, decreased average daily weight gain, overall porcine circovirus load, and any combination thereof.

35. The method of claim 33, wherein the PCV2 ORF2 protein is recombinantly produced.

36. The method of claim 33, wherein said PCV2 ORF2 protein comprises a protein selected from the group consisting of:
  a. a polypeptide comprising a sequence selected from the group consisting of SEQ ID NO: 5, SEQ ID NO: 6, SEQ ID NO: 9, SEQ ID NO: 10, and SEQ ID NO: 11;
  b. any polypeptide that is at least 90% homologous to the polypeptide of a);
  c. a polypeptide that is encoded by a polynucleotide comprising the sequence of SEQ ID NO: 3 or SEQ ID NO: 4; or
  d. any polypeptide that is encoded by a polynucleotide that is at least 90% homologous to the polynucleotide of c).

37. The method of claim 33, wherein said PCV2 ORF2 protein is a recombinant baculovirus expressed PCV2 ORF2 protein.

38. The method of claim 33, wherein said PCV2 ORF2 protein is formulated and administered in one (1) mL per dose.

39. The method of claim 33, wherein said administering of the single dose occurs in pigs 3 weeks of age or older.

40. The method of claim 33, wherein said administering of the single dose occurs within about 3 weeks of exposure to a virulent porcine circovirus type 2 antigen.

41. The method of claim 33, wherein said immunogenic composition further comprises at least one additional component selected from the group consisting of veterinary-acceptable carriers, pharmaceutical-acceptable carriers, adjuvants, cell culture supernatant, and immunomodulatory agents.

42. The method of claim 33, wherein said administering is performed using a method selected from the group consisting of intradermal, intratracheal, intravaginal, intramuscular, intranasal, intravenous, intravascular, intraarterial, intraperitoneal, oral, intrathecal, subcutaneous, intracutaneous, intracardial, intralobal, intramedullar, or intrapulmonar.

43. The method of claim 33, wherein the administering of said PCV2 ORF2 protein does not show adverse events or injection site reactions.

44. The method of claim 34, wherein said one or more clinical symptoms associated with PCV2 infection is PCV2 virus shedding.

45. The method of claim 34, wherein said one or more clinical symptoms associated with PCV2 infection is lymphoid infection caused by PCV2.

46. The method of claim 34, wherein said one or more clinical symptoms associated with PCV2 infection is increased mortality rate.

47. The method of claim 34, wherein said one or more clinical symptoms associated with PCV2 infection is decreased average daily weight gain.

48. The method of claim 34, wherein said one or more clinical symptoms associated with PCV2 infection is the overall porcine circovirus load as determined by PCV2 viremia.

49. The method according to claim 41, wherein said adjuvant is selected from the group consisting of aluminum hydroxide, aluminum phosphate, saponins, water-in-oil emulsions, oil-in-water emulsion, water-in-oil-water emulsion, polymers of acrylic or methacrylic acid, copolymers of maleic anhydride and alkenyl derivative, and any combination thereof.

50. The method according to claim 49, wherein said adjuvant is included at a concentration of 100 µg to 10 mg per dose.

* * * * *

SEQUENCE LISTING

```
<160> NUMBER OF SEQ ID NOS: 11

<210> SEQ ID NO 1
<211> LENGTH: 8
<212> TYPE: DNA
<213> ORGANISM: Artificial Sequence
<220> FEATURE:
<223> OTHER INFORMATION: This is a modified Kozak's sequence

<400> SEQUENCE: 1 ccgccatg                                                              8

<210> SEQ ID NO 2
<211> LENGTH: 6
<212> TYPE: DNA
<213> ORGANISM: Artificial Sequence
<220> FEATURE:
<223> OTHER INFORMATION: This is a recombinant Eco R1 sequence

<400> SEQUENCE: 2 gaattc                                                                6

<210> SEQ ID NO 3
<211> LENGTH: 713
<212> TYPE: DNA
<213> ORGANISM: Porcine circovirus

<400> SEQUENCE: 3
cagctatgac gtatccaagg aggcgttacc gcagaagaag acaccgcccc cgcagccatc    60
ttggccagat cctccgccgc cgcccctggc tcgtccaccc ccgccaccgc taccgttgga   120
gaaggaaaaa tggcatcttc aacacccgcc tctcccgcac cttcggatat actgtggaga   180
aggaaaaatg gcatcttcaa cacccgcctc tcccgcacct tcggatatac tgtgacgact   240
ttgttccccc gggaggggg accaacaaaa tctctatacc ctttgaatac tacagaataa   300
gaaaggttaa ggttgaattc tggccctgct ccccatcac ccagggtgat aggggagtgg   360
gctccactgc tgttattcta gatgataact ttgtaacaaa ggccacagcc ctaacctatg   420
acccatatgt aaactactcc tccgccata caatccccca accttctcc taccactccc    480 gttacttcac acccaaacct gttcttgact ccactattga ttacttccaa ccaaataaca   540
aaaggaatca gctttggctg aggctacaaa cctctagaaa tgtggaccac gtaggcctcg   600
gcactgcgtt cgaaaacagt aaatacgacc aggactacaa tatccgtgta accatgtatg   660
tacaattcag agaatttaat cttaaagacc ccccacttaa accctaaatg aat           713

<210> SEQ ID NO 4
<211> LENGTH: 713
<212> TYPE: DNA
```

<213> ORGANISM: Porcine circovirus

<400> SEQUENCE: 4

```
ccgccatgac gtatccaagg aggcgttacc gcagaagaag acaccgcccc cgcagccatc    60
ttggccagat cctccgccgc cgcccctggc tcgtccaccc ccgccaccgc taccgttgga   120
gaaggaaaaa tggcatcttc aacacccgcc tctcccgcac cttcggatat actgtcaagg   180
ctaccacagt cacaacgccc tcctgggcgg tggacatgat gagatttaat attgacgact   240
ttgttccccc gggagggggg accaacaaaa tctctatacc ctttgaatac tacagaataa   300
gaaaggttaa ggttgaattc tggccctgct cccccatcac ccagggtgat aggggagtgg   360
gctccactgc tgttattcta gatgataact ttgtaacaaa ggccacagcc ctaacctatg   420
acccatatgt aaactactcc tcccgccata caatccccca accttctcc taccactccc    480
gttacttcac acccaaacct gttcttgact ccactattga ttacttccaa ccaaataaca   540
aaaggaatca gctttggctg aggctacaaa cctctagaaa tgtggaccac gtaggcctcg   600
gcactgcgtt cgaaaacagt aaatacgacc aggactacaa tatccgtgta accatgtatg   660
tacaattcag agaatttaat cttaaagacc ccccacttga accctaagaa ttc           713
```

<210> SEQ ID NO 5
<211> LENGTH: 233
<212> TYPE: PRT
<213> ORGANISM: Porcine circovirus

<400> SEQUENCE: 5

```
Met Thr Tyr Pro Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
```

-continued

```
225                 230

<210> SEQ ID NO 6
<211> LENGTH: 233
<212> TYPE: PRT
<213> ORGANISM: Porcine circovirus

<400> SEQUENCE: 6

Met Thr Tyr Pro Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230

<210> SEQ ID NO 7
<211> LENGTH: 756
<212> TYPE: DNA
<213> ORGANISM: Artificial Sequence
<220> FEATURE:
<223> OTHER INFORMATION: This sequence is from porcine circovirus type
      2, open reading frame 2, together with a portion from the pGEM
      T-easy vector.

<400> SEQUENCE: 7
gcggccgcgg gaattcgatc cgccatgacg tatccaagga ggcgttaccg cagaagaaga      60
caccgccccc gcagccatct tggccagatc ctccgccgcc gcccctggct cgtccacccc     120
cgccaccgct accgttggag aaggaaaaat ggcatcttca acacccgcct ctcccgcacc     180
ttcggatata ctgtcaaggc taccacagtc acaacgcccc ctgggcggt ggacatgatg      240 agatttaata ttgacgactt tgttcccccg ggagggggga ccaacaaaat ctctataccc     300
tttgaatact acagaataag aaaggttaag gttgaattct ggccctgctc ccccatcacc     360
```

-continued

```
cagggtgata ggggagtggg ctccactgct gttattctag atgataactt tgtaacaaag    420
gccacagccc taacctatga cccatatgta aactactcct cccgccatac aatcccccaa    480
cccttctcct accactcccg ttacttcaca cccaaacctg ttcttgactc cactattgat    540
tacttccaac caaataacaa aaggaatcag ctttggctga ggctacaaac ctctagaaat    600
gtggaccacg taggcctcgg cactgcgttc gaaaacagta aatacgacca ggactacaat    660
atccgtgtaa ccatgtatgt acaattcaga gaatttaatc ttaaagaccc ccccacttgaa    720 ccctaagaat tctatcacta gtgaattcgc ggccgc                               756
```

```
<210> SEQ ID NO 8
<211> LENGTH: 10387
<212> TYPE: DNA
<213> ORGANISM: Artificial Sequence
<220> FEATURE:
<223> OTHER INFORMATION: This is the porcine circovirus type 2, ORF2
      construct, which includes baculovirus and pGEM T-easy coding
      sequences.

<400> SEQUENCE: 8
```

```
aagctttact cgtaaagcga gttgaaggat catatttagt tgcgtttatg agataagatt     60
gaaagcacgt gtaaaatgtt tcccgcgcgt tggcacaact atttacaatg cggccaagtt    120
ataaaagatt ctaatctgat atgttttaaa acacctttgc ggcccgagtt gtttgcgtac    180
gtgactagcg aagaagatgt gtggaccgca gaacagatag taaaacaaaa ccctagtatt    240
ggagcaataa tcgatttaac caacacgtct aaatattatg atggtgtgca tttttttgcgg    300 gcgggcctgt tatacaaaaa aattcaagta cctggccaga ctttgccgcc tgaaagcata    360
gttcaagaat ttattgacac ggtaaaagaa tttacagaaa agtgtcccgg catgttggtg    420
ggcgtgcact gcacacacgg tattaatcgc accggttaca tggtgtgcag atatttaatg    480
cacaccctgg gtattgcgcc gcaggaagcc atagatagat tcgaaaaagc cagaggtcac    540
aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg gatattctcc accacaatgt tggcaacgtt gatgttacgt ttatgctttt    780
ggttttccac gtacgtcttt tggccggtaa tagccgtaaa cgtagtgccg tcgcgcgtca    840
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
cttctccaaa tttaaattct ccaattttaa cgcgagccat tttgatacac gtgtgtcgat   1620
```

```
tttgcaacaa ctattgtttt ttaacgcaaa ctaaacttat tgtggtaagc aataattaaa   1680
tatggggaa catgcgccgc tacaacactc gtcgttatga acgcagacgg cgccggtctc    1740
ggcgcaagcg gctaaaacgt gttgcgcgtt caacgcggca acatcgcaa aagccaatag    1800
tacagttttg atttgcatat taacggcgat tttttaaatt atcttattta ataaatagtt   1860
atgacgccta caactccccg cccgcgttga ctcgctgcac ctcgagcagt tcgttgacgc   1920
cttcctccgt gtggccgaac acgtcgagcg ggtggtcgat gaccagcggc gtgccgcacg   1980
cgacgcacaa gtatctgtac accgaatgat cgtcgggcga aggcacgtcg gcctccaagt   2040
ggcaatattg gcaaattcga aaatatatac agttgggttg tttgcgcata tctatcgtgg   2100
cgttgggcat gtacgtccga acgttgattt gcatgcaagc cgaaattaaa tcattgcgat   2160
tagtgcgatt aaaacgttgt acatcctcgc ttttaatcat gccgtcgatt aaatcgcgca   2220
atcgagtcaa gtgatcaaag tgtggaataa tgttttcttt gtattcccga gtcaagcgca   2280
gcgcgtattt taacaaacta gccatcttgt aagttagttt catttaatgc aactttatcc   2340
aataatatat tatgtatcgc acgtcaagaa ttaacaatgc gcccgttgtc gcatctcaac   2400
acgactatga tagagatcaa ataaagcgcg aattaaatag cttgcgacgc aacgtgcacg   2460
atctgtgcac gcgttccggc acgagctttg attgtaataa gtttttacga agcgatgaca   2520
tgaccccgt agtgacaacg atcacgccca aaagaactgc cgactacaaa attaccgagt     2580
atgtcggtga cgttaaaact attaagccat ccaatcgacc gttagtcgaa tcaggaccgc    2640
tggtgcgaga agccgcgaag tatggcgaat gcatcgtata acgtgtggag tccgctcatt    2700
agagcgtcat gtttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880
aattttaaaa aacgcagcaa gagaaacatt tgtatgaaag aatgcgtaga aggaaagaaa   2940
aatgtcgtcg acatgctgaa caacaagatt aatatgcctc cgtgtataaa aaaaatattg   3000
aacgatttga agaaaacaa tgtaccgcgc ggcggtatgt acaggaagag gtttatacta     3060
aactgttaca ttgcaaacgt ggtttcgtgt gccaagtgtg aaaaccgatg tttaatcaag   3120
gctctgacgc atttctacaa ccacgactcc aagtgtgtgg gtgaagtcat gcatctttta   3180
atcaaatccc aagatgtgta taaaccacca aactgccaaa aatgaaaac tgtcgacaag    3240
ctctgtccgt tgctggcaa ctgcaagggt ctcaatccta tttgtaatta ttgaataata    3300
aaacaattat aaatgctaaa tttgtttttt attaacgata caaaccaaac gcaacaagaa   3360
catttgtagt attatctata attgaaaacg cgtagttata atcgctgagg taatatttaa   3420
aatcattttc aaatgattca cagttaattt gcgacaatat aatttatttt tcacataaac   3480
tagacgcctt gtcgtcttct tcttcgtatt ccttctcttt ttcattttc tcctcataaa    3540
aattaacata gttattatcg tatccatata tgtatctatc gtatagagta aatttttgt    3600
tgtcataaat atatatgtct tttttaatgg ggtgtatagt accgctgcgc atagtttttc   3660
tgtaatttac aacagtgcta ttttctggta gttcttcgga gtgtgttgct ttaattatta   3720
aatttatata atcaatgaat ttgggatcgt cggttttgta caatatgttg ccggcatagt   3780
acgcagcttc ttctagttca attacaccat ttttagcag caccggatta acataacttt    3840
ccaaaatgtt gtacgaaccg ttaaacaaaa acagttcacc tccttttct atactattgt    3900
ctgcgagcag ttgtttgttg ttaaaaataa cagccattgt aatgagacgc acaaactaat   3960
```

```
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atcagatctg    4140
cagcggccgc gggaattcga tccgccatga cgtatccaag gaggcgttac cgcagaagaa    4200
gacaccgccc ccgcagccat cttggccaga tcctccgccg ccgcccctgg ctcgtccacc    4260
cccgccaccg ctaccgttgg agaaggaaaa atggcatctt caacacccgc tctcccgca    4320 ccttcggata tactgtcaag gctaccacag tcacaacgcc ctcctgggcg gtggacatga    4380
tgagatttaa tattgacgac tttgttcccc cgggagggg gaccaacaaa atctctatac    4440
cctttgaata ctacagaata agaaaggtta aggttgaatt ctggccctgc tcccccatca    4500
cccagggtga tagggagtg ggctccactg ctgttattct agatgataac tttgtaacaa    4560
aggccacagc cctaacctat gacccatatg taaactactc ctcccgccat acaatccccc    4620
aacccttctc ctaccactcc cgttacttca cacccaaacc tgttcttgac tccactattg    4680
attacttcca accaaataac aaaaggaatc agctttggct gaggctacaa acctctagaa    4740
atgtggacca cgtaggcctc ggcactgcgt tcgaaaacag taaatacgac caggactaca    4800
atatccgtgt aaccatgtat gtacaattca gagaatttaa tcttaaagac cccccacttg    4860
aaccctaaga attctatcac tagtgaattc gcggccgccg ccgctccag aattctagaa    4920 ggtacccggg atccttttcct gggacccggc aagaaccaaa aactcactct cttcaaggaa    4980
atccgtaatg ttaaacccga cacgatgaag cttgtcgttg gatggaaagg aaaagagttc    5040
tacagggaaa cttggacccg cttcatggaa gacagcttcc ccattgttaa cgaccaagaa    5100
gtgatggatg ttttccttgt tgtcaacatg cgtcccacta gacccaaccg ttgttacaaa    5160
ttcctggccc aacacgctct gcgttgcgac cccgactatg tacctcatga cgtgattagg    5220
atcgtcgagc cttcatgggt gggcagcaac aacgagtacc gcatcagcct ggctaagaag    5280
ggcggcggct gcccaataat gaaccttcac tctgagtaca ccaactcgtt cgaacagttc    5340
atcgatcgtg tcatctggga gaacttctac aagcccatcg tttacatcgg taccgactct    5400
gctgaagagg aggaaattct ccttgaagtt tccctggtgt tcaaagtaaa ggagtttgca    5460
ccagacgcac ctctgttcac tggtccggcg tattaaaaca cgatacattg ttattagtac    5520
atttattaag cgctagattc tgtgcgttgt tgatttacag acaattgttg tacgtatttt    5580
aataattcat taaatttata atctttaggg tggtatgtta gagcgaaaat caaatgattt    5640
tcagcgtctt tatatctgaa tttaaatatt aaatcctcaa tagatttgta aaataggttt    5700
cgattagttt caaacaaggg ttgttttttcc gaaccgatgg ctggactatc taatggattt    5760
tcgctcaacg ccacaaaact tgccaaatct tgtagcagca atctagcttt gtcgatattc    5820
gtttgtgttt tgttttgtaa taaaggttcg acgtcgttca aaatattatg cgcttttgta    5880
tttctttcat cactgtcgtt agtgtacaat tgactgacg taaacacgtt aaataaagct    5940
tggacatatt taacatcggg cgtgttagct ttattaggcc gattatcgtc gtcgtcccaa    6000
ccctcgtcgt tagaagttgc ttccgaagac gattttgcca tagccacacg acgcctatta    6060
attgtgtcgg ctaacacgtc cgcgatcaaa tttgtagttg agcttttgg aattatttct    6120 gattgcgggc gttttgggc gggtttcaat ctaactgtgc ccgattttaa ttcagacaac    6180
acgttagaaa gcgatggtgc aggcggtggt aacatttcag acggcaaatc tactaatggc    6240
ggcggtggtg gagctgatga taaatctacc atcggtggag cgcaggcgg gctggcggc    6300 ggaggcggag gcggaggtgg tggcggtgat gcagacggcg gtttaggctc aaatgtctct    6360
```

```
ttaggcaaca cagtcggcac ctcaactatt gtactggttt cgggcgccgt ttttggtttg   6420
accggtctga gacgagtgcg atttttttcg tttctaatag cttccaacaa ttgttgtctg   6480
tcgtctaaag gtgcagcggg ttgaggttcc gtcggcattg gtggagcggg cggcaattca   6540
gacatcgatg gtggtggtgg tggtggaggc gctggaatgt taggcacggg agaaggtggt   6600
ggcggcggtg ccgccggtat aatttgttct ggtttagttt gttcgcgcac gattgtgggc   6660
accggcgcag gcgccgctgg ctgcacaacg gaaggtcgtc tgcttcgagg cagcgcttgg   6720
ggtggtggca attcaatatt ataattggaa tacaaatcgt aaaaatctgc tataagcatt   6780
gtaatttcgc tatcgtttac cgtgccgata tttaacaacc gctcaatgta agcaattgta   6840
ttgtaaagag attgtctcaa gctcgccgca cgccgataac aagccttttc attttacta   6900 cagcattgta gtggcgagac acttcgctgt cgtcgacgta catgtatgct tgttgtcaa   6960 aaacgtcgtt ggcaagcttt aaaatattta aagaacatc tctgttcagc accactgtgt   7020
tgtcgtaaat gttgttttg ataatttgcg cttccgcagt atcgacacgt tcaaaaatt   7080 gatgcgcatc aatttttgttg ttcctattat tgaataaata agattgtaca gattcatatc   7140
tacgattcgt catggccacc acaaatgcta cgctgcaaac gctggtacaa ttttacgaaa   7200
actgcaaaaa cgtcaaaact cggtataaaa taatcaacgg gcgctttggc aaaatatcta   7260
ttttatcgca caagcccact agcaaattgt atttgcagaa acaatttcg gcgcacaatt   7320 ttaacgctga cgaaataaaa gttcaccagt taatgagcga ccacccaaat tttataaaaa   7380
tctattttaa tcacggttcc atcaacaacc aagtgatcgt gatggactac attgactgtc   7440
ccgatttatt tgaaacacta caaattaaag gcgagctttc gtaccaactt gttagcaata   7500
ttattagaca gctgtgtgaa gcgctcaacg atttgcacaa gcacaatttc atacacaacg   7560
acataaaact cgaaaatgtc ttatatttcg aagcacttga tcgcgtgtat gtttgcgatt   7620
acggattgtg caaacacgaa aactcactta gcgtgcacga cggcacgttg gagtatttta   7680
gtccggaaaa aattcgacac acaactatgc acgtttcgtt tgactggtac gcggcgtgtt   7740
aacatacaag ttgctaacgt aatcatggtc atagctgttt cctgtgtgaa attgttatcc   7800
gctcacaatt ccacacaaca tacgagccgg aagcataaag tgtaaagcct ggggtgccta   7860
atgagtgagc taactcacat taattgcgtt gcgctcactg cccgctttcc agtcgggaaa   7920
cctgtcgtgc cagctgcatt aatgaatcgg ccaacgcgcg gggagaggcg gtttgcgtat   7980
tgggcgctct tccgcttcct cgctcactga ctcgctgcgc tcggtcgttc ggctgcggcg   8040
agcggtatca gctcactcaa aggcggtaat acgttatcc acagaatcag gggataacgc   8100
aggaaagaac atgtgagcaa aaggccagca aaaggccagg aaccgtaaaa aggccgcgtt   8160
gctggcgttt ttccataggc tccgcccccc tgacgagcat cacaaaaatc gacgctcaag   8220
tcagaggtgg cgaaacccga caggactata agataccag gcgtttcccc ctggaagctc   8280
cctcgtgcgc tctcctgttc cgaccctgcc gcttaccgga tacctgtccg cctttctccc   8340
ttcgggaagc gtggcgcttt ctcatagctc acgctgtagg tatctcagtt cggtgtaggt   8400
cgttcgctcc aagctgggct gtgtgcacga accccccgtt cagcccgacc gctgcgcctt   8460
atccggtaac tatcgtcttg agtccaaccc ggtaagacac gacttatcgc cactggcagc   8520
agccactggt aacaggatta gcagagcgag gtatgtaggc ggtgctacag agttcttgaa   8580
gtggtggcct aactacggct acactagaag gacagtattt ggtatctgcg ctctgctgaa   8640
gccagttacc ttcggaaaaa gagttggtag ctcttgatcc ggcaaacaaa ccaccgctgg   8700
```

| tagcggtggt tttttgtttt gcaagcagca gattacgcgc agaaaaaaag gatctcaaga | 8760 |
| agatcctttg atcttttcta cggggtctga cgctcagtgg aacgaaaact cacgttaagg | 8820 |
| gattttggtc atgagattat caaaaaggat cttcacctag atccttttaa attaaaaatg | 8880 |
| aagttttaaa tcaatctaaa gtatatatga gtaaacttgg tctgacagtt accaatgctt | 8940 |
| aatcagtgag gcacctatct cagcgatctg tctatttcgt tcatccatag ttgcctgact | 9000 |
| ccccgtcgtg tagataacta cgatacggga gggcttacca tctggcccca gtgctgcaat | 9060 |
| gataccgcga gacccacgct caccggctcc agatttatca gcaataaacc agccagccgg | 9120 |
| aagggccgag cgcagaagtg gtcctgcaac tttatccgcc tccatccagt ctattaattg | 9180 |
| ttgccgggaa gctagagtaa gtagttcgcc agttaatagt ttgcgcaacg ttgttgccat | 9240 |
| tgctacaggc atcgtggtgt cacgctcgtc gtttggtatg gcttcattca gctccggttc | 9300 |
| ccaacgatca aggcgagtta catgatcccc catgttgtgc aaaaaagcgg ttagctcctt | 9360 |
| cggtcctccg atcgttgtca gaagtaagtt ggccgcagtg ttatcactca tggttatggc | 9420 |
| agcactgcat aattctctta ctgtcatgcc atccgtaaga tgcttttctg tgactggtga | 9480 |
| gtactcaacc aagtcattct gagaatagtg tatgcggcga ccgagttgct cttgcccggc | 9540 |
| gtcaatacgg gataataccg cgccacatag cagaacttta aaagtgctca tcattggaaa | 9600 |
| acgttcttcg gggcgaaaac tctcaaggat cttaccgctg ttgagatcca gttcgatgta | 9660 |
| acccactcgt gcacccaact gatcttcagc atcttttact ttcaccagcg tttctgggtg | 9720 |
| agcaaaaaca ggaaggcaaa atgccgcaaa aaagggaata agggcgacac ggaaatgttg | 9780 |
| aatactcata ctcttccttt ttcaatatta ttgaagcatt tatcagggtt attgtctcat | 9840 |
| gagcggatac atatttgaat gtatttagaa aaataaacaa ataggggttc cgcgcacatt | 9900 |
| tccccgaaaa gtgccacctg acgtctaaga accattatt atcatgacat aacctataa | 9960 |
| aaataggcgt atcacgaggc cctttcgtct cgcgcgtttc ggtgatgacg gtgaaaacct | 10020 |
| ctgacacatg cagctcccgg agacggtcac agcttgtctg taagcggatg ccgggagcag | 10080 |
| acaagcccgt cagggcgcgt cagcgggtgt tggcgggtgt cggggctggc ttaactatgc | 10140 |
| ggcatcagag cagattgtac tgagagtgca ccatatgcgg tgtgaaatac cgcacagatg | 10200 |
| cgtaaggaga aaataccgca tcaggcgcca ttcgccattc aggctgcgca actgttggga | 10260 |
| agggcgatcg gtgcgggcct cttcgctatt acgccagctg gcgaaagggg gatgtgctgc | 10320 |
| aaggcgatta agttgggtaa cgccagggtt ttcccagtca cgacgttgta aaacgacggc | 10380 |
| cagtgcc | 10387 |

```
<210> SEQ ID NO 9
<211> LENGTH: 20
<212> TYPE: PRT
<213> ORGANISM: Porcine circovirus

<400> SEQUENCE: 9

Ser Tyr Pro Arg Arg Tyr Arg Arg Arg His His Pro Pro Ser
1               5                   10                  15

His Leu Gly Gln
            20

<210> SEQ ID NO 10
<211> LENGTH: 19
<212> TYPE: PRT
<213> ORGANISM: Porcine circovirus

<400> SEQUENCE: 10
```

-continued

```
Pro Arg His His Tyr Arg Pro Arg Arg Lys Asn Gly Ile Phe Asn Thr
1               5                   10                  15

Thr Leu Ser

<210> SEQ ID NO 11
<211> LENGTH: 233
<212> TYPE: PRT
<213> ORGANISM: Artificial Sequence
<220> FEATURE:
<223> OTHER INFORMATION: This is an amino acid sequence for porcine
      circovirus type 2, open reading frame 2.

<400> SEQUENCE: 11

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Arg Thr
        50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Lys Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```